United States Patent
Ayala et al.

(10) Patent No.: US 8,512,389 B2
(45) Date of Patent: Aug. 20, 2013

(54) SYSTEM AND METHOD FOR INTRODUCING MULTIPLE MEDICAL DEVICES

(75) Inventors: Juan Carlos Ayala, Santiago (CL); Stephen E. Deal, Charlotte, NC (US); Charles Agnew, West Lafayette, IN (US); Gregory J. Skerven, Kernersville, NC (US)

(73) Assignee: Cook Medical Technologies, LLC, Bloomington, IN (US)

( * ) Notice: Subject to any disclaimer, the term of this patent is extended or adjusted under 35 U.S.C. 154(b) by 344 days.

(21) Appl. No.: 12/973,207

(22) Filed: Dec. 20, 2010

(65) Prior Publication Data
US 2011/0087234 A1   Apr. 14, 2011

Related U.S. Application Data

(63) Continuation of application No. 10/902,438, filed on Jul. 29, 2004, now Pat. No. 7,967,830.

(60) Provisional application No. 60/491,408, filed on Jul. 31, 2003, provisional application No. 60/563,968, filed on Apr. 21, 2004, provisional application No. 60/570,656, filed on May 13, 2004.

(51) Int. Cl.
*A61F 2/06* (2013.01)
*A61M 25/09* (2006.01)

(52) U.S. Cl.
USPC ............... 623/1.11; 606/108; 604/103.04; 604/164.05

(58) Field of Classification Search
USPC .................. 606/1, 108, 191–200; 600/585; 604/103.04, 161, 164.05, 11–18, 59–64; 623/1.11, 1.12; 30/90.4
See application file for complete search history.

(56) References Cited

U.S. PATENT DOCUMENTS

| | | | |
|---|---|---|---|
| 3,769,981 | A | 11/1973 | McWhorter |
| 4,748,982 | A | 6/1988 | Horzewski et al. |
| 4,762,129 | A | 8/1988 | Bonzel |
| 4,824,435 | A | 4/1989 | Geisy et al. |
| 4,913,141 | A | 4/1990 | Hillstead |

(Continued)

FOREIGN PATENT DOCUMENTS

| | | |
|---|---|---|
| EP | 0 397 357 A | 11/1990 |
| EP | 0 732 087 A | 9/1996 |

(Continued)

OTHER PUBLICATIONS

Wilson-Cook Medical Inc., "Swenson Wire Guided Papillotomes/Sphincterotomes," 2 pp., 1986.

(Continued)

*Primary Examiner* — Kathleen Holwerda
(74) *Attorney, Agent, or Firm* — Brinks Hofer Gilson & Lione

(57) ABSTRACT

A method and apparatus for introducing a first elongate medical device and short wire guide that are coupled together into a work site and remotely disconnecting them within the work site such that a secondary device comprising a catheter member can be introduced over the wire guide to the work site, and/or a second wire guide can be introduced to the work site via a passageway of the primary access device. A separating member may be provided to remotely separate the wire guide from the elongate medical device.

7 Claims, 35 Drawing Sheets

(56) References Cited

U.S. PATENT DOCUMENTS

| | | |
|---|---|---|
| 4,943,278 A | 7/1990 | Euteneuer et al. |
| 4,983,167 A | 1/1991 | Sahota |
| 4,988,356 A | 1/1991 | Crittenden et al. |
| 5,061,273 A | 10/1991 | Yock |
| 5,135,535 A | 8/1992 | Kramer |
| 5,154,725 A | 10/1992 | Leopold |
| 5,156,594 A | 10/1992 | Keith |
| 5,195,978 A | 3/1993 | Schiffer |
| 5,205,822 A | 4/1993 | Johnson et al. |
| 5,217,482 A | 6/1993 | Keith |
| 5,232,445 A | 8/1993 | Bonzel |
| 5,300,085 A | 4/1994 | Yock |
| 5,308,318 A | 5/1994 | Plassche, Jr. |
| 5,324,269 A | 6/1994 | Miraki |
| 5,334,147 A | 8/1994 | Johnson |
| 5,336,184 A | 8/1994 | Teirstein |
| 5,346,505 A | 9/1994 | Leopold |
| 5,350,395 A | 9/1994 | Yock |
| 5,364,376 A | 11/1994 | Horzewski et al. |
| 5,370,616 A | 12/1994 | Keith et al. |
| 5,389,087 A | 2/1995 | Miraki |
| 5,395,334 A | 3/1995 | Keith et al. |
| 5,425,711 A | 6/1995 | Ressemann et al. |
| 5,437,290 A | 8/1995 | Bolger et al. |
| 5,451,233 A | 9/1995 | Yock |
| 5,458,613 A | 10/1995 | Gharibadeh et al. |
| 5,496,346 A | 3/1996 | Horzewski et al. |
| 5,507,768 A | 4/1996 | Lau et al. |
| 5,507,807 A | 4/1996 | Shippert |
| 5,514,092 A | 5/1996 | Forman et al. |
| 5,522,818 A | 6/1996 | Keith et al. |
| 5,531,700 A | 7/1996 | Moore et al. |
| 5,536,248 A | 7/1996 | Weaver et al. |
| 5,567,203 A | 10/1996 | Euteneuer et al. |
| 5,569,215 A | 10/1996 | Crocker |
| 5,569,295 A * | 10/1996 | Lam .................. 606/198 |
| 5,599,299 A | 2/1997 | Weaver et al. |
| 5,599,300 A | 2/1997 | Weaver et al. |
| 5,626,600 A | 5/1997 | Horzewski et al. |
| 5,658,251 A | 8/1997 | Ressemann et al. |
| 5,667,493 A | 9/1997 | Janacek |
| 5,690,644 A | 11/1997 | Yurek et al. |
| 5,702,364 A | 12/1997 | Euteneuer et al. |
| 5,702,439 A | 12/1997 | Keith et al. |
| 5,720,724 A | 2/1998 | Ressemann et al. |
| 5,728,066 A | 3/1998 | Daneshvar |
| 5,728,067 A | 3/1998 | Enger |
| 5,749,888 A | 5/1998 | Yock |
| 5,779,731 A | 7/1998 | Leavitt |
| 5,782,855 A | 7/1998 | Lau et al. |
| 5,797,952 A | 8/1998 | Klein |
| 5,860,938 A | 1/1999 | Lafontaine et al. |
| 5,882,336 A | 3/1999 | Janacek |
| 5,921,952 A | 7/1999 | Desmond, III et al. |
| 5,921,971 A | 7/1999 | Agro et al. |
| 5,980,486 A | 11/1999 | Enger |
| 6,007,517 A | 12/1999 | Anderson |
| 6,007,522 A | 12/1999 | Agro et al. |
| 6,036,715 A | 3/2000 | Yock |
| 6,050,949 A | 4/2000 | White et al. |
| 6,066,114 A | 5/2000 | Goodin et al. |
| 6,071,273 A | 6/2000 | Euteneuer et al. |
| 6,071,285 A | 6/2000 | Lashinski et al. |
| 6,077,295 A | 6/2000 | Limon et al. |
| 6,078,832 A | 6/2000 | Lenker et al. |
| 6,095,990 A | 8/2000 | Parodi |
| 6,113,607 A | 9/2000 | Lau et al. |
| 6,129,708 A | 10/2000 | Enger |
| 6,152,910 A | 11/2000 | Agro et al. |
| 6,165,197 A | 12/2000 | Yock |
| 6,248,100 B1 | 6/2001 | De Tolede et al. |
| 6,264,624 B1 | 7/2001 | Desmond, III et al. |
| 6,273,899 B1 | 8/2001 | Kramer |
| 6,277,093 B1 | 8/2001 | Lee |
| 6,287,291 B1 | 9/2001 | Bigus et al. |
| 6,312,404 B1 | 11/2001 | Agro et al. |
| 6,364,841 B1 | 4/2002 | White et al. |
| 6,380,457 B1 | 4/2002 | Yurek et al. |
| 6,398,799 B2 | 6/2002 | Kramer |
| 6,447,540 B1 | 9/2002 | Fontaine |
| 6,475,187 B1 | 11/2002 | Gerberding |
| 6,488,694 B1 | 12/2002 | Lau et al. |
| 6,520,951 B1 | 2/2003 | Carrillo, Jr. et al. |
| 6,527,789 B1 | 3/2003 | Lau et al. |
| 6,562,064 B1 | 5/2003 | Debeer |
| 6,575,993 B1 | 6/2003 | Yock |
| 6,576,006 B2 | 6/2003 | Limon et al. |
| 6,582,459 B1 | 6/2003 | Lau et al. |
| 6,592,549 B2 | 7/2003 | Gerdts et al. |
| 6,827,731 B2 | 12/2004 | Armstrong et al. |
| 7,264,001 B2 | 9/2007 | Boutillette et al. |
| 2002/0099405 A1 | 7/2002 | Yurek et al. |
| 2002/0103525 A1 | 8/2002 | Cummings |
| 2002/0143251 A1 | 10/2002 | Richardson et al. |
| 2003/0018376 A1 | 1/2003 | Solar et al. |
| 2003/0040737 A1 | 2/2003 | Merril et al. |
| 2004/0143286 A1 * | 7/2004 | Johnson et al. ............ 606/194 |
| 2005/0059990 A1 | 3/2005 | Ayala et al. |

FOREIGN PATENT DOCUMENTS

| | | |
|---|---|---|
| EP | 0 948 372 | 3/1998 |
| EP | 1 348 461 A | 10/2003 |
| WO | WO 94/22379 | 10/1994 |
| WO | WO 98/10820 | 3/1998 |
| WO | WO 02/47549 A | 6/2002 |
| WO | WO 03/030783 A | 4/2003 |

OTHER PUBLICATIONS

Wilson-Cook Medical, "Papillotome Pt-20-St. Mary's," 2 pp. Apr. 13, 1987 (partially redacted).

Swenson, Bruce MD, Trinity Medical Center, "Swenson Wire Guided Papillotomes/Sphincterotomes," 2 pp. 1988 (partially redacted).

Wilson-Cook Medical, "Biliary Motility Catheter Guided," 1 pp., Mar. 2, 1988 (partially redacted).

Sherman, Stuart, MD., et al., "Wire-Guided Sphincterotomy," *The American Journal of Gastroenterology*, vol. 89, No. 12, 1994, pp. 2125-2129.

* cited by examiner

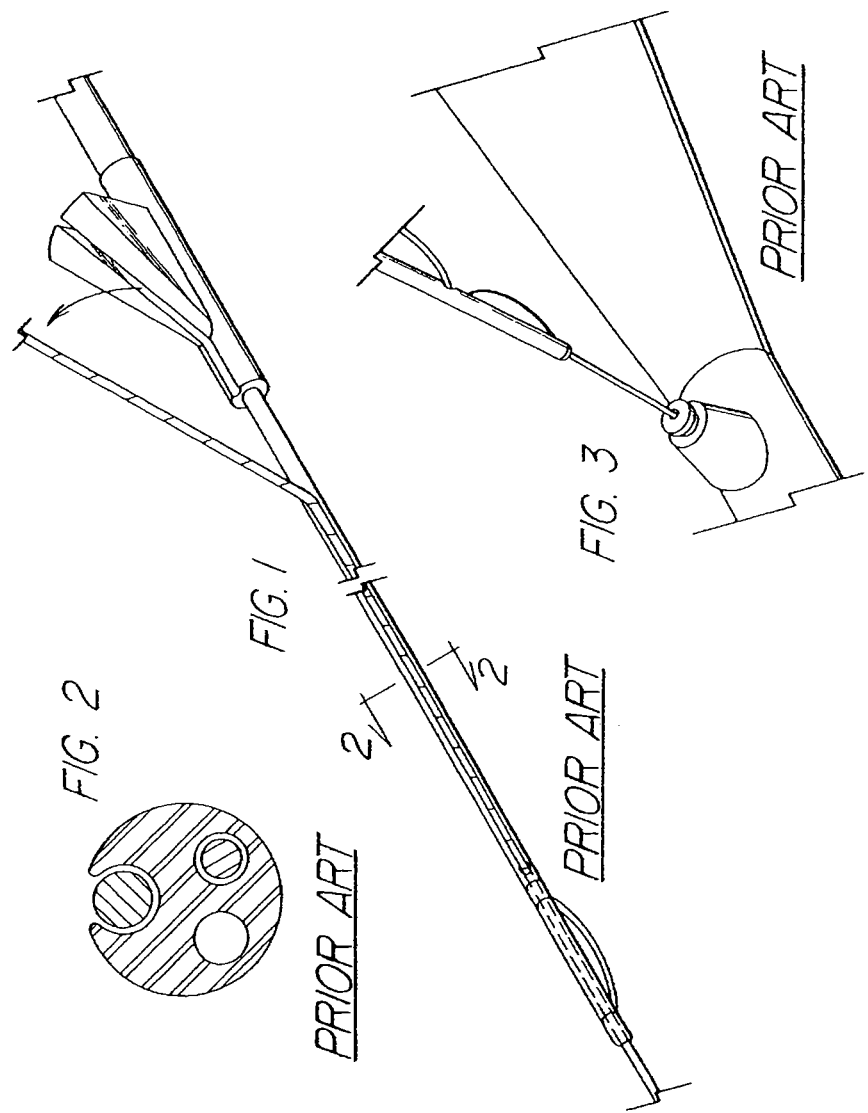

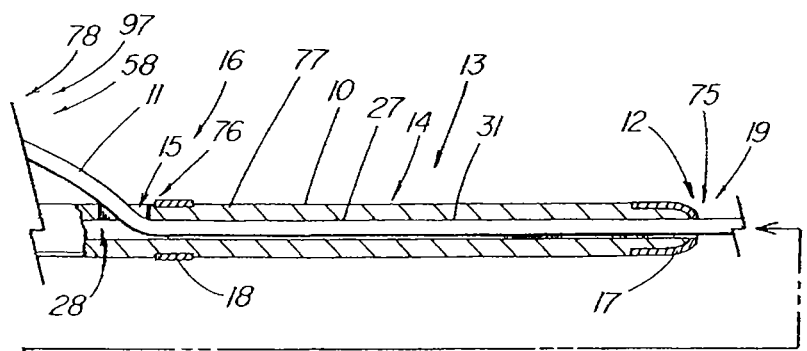
FIG. 5
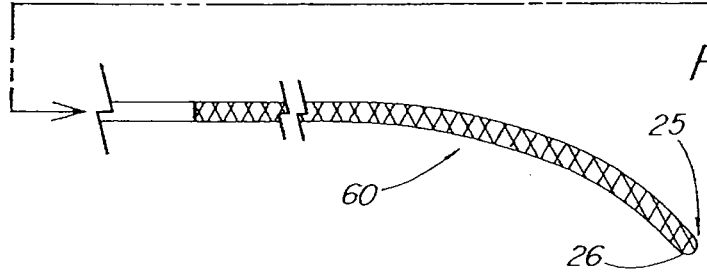
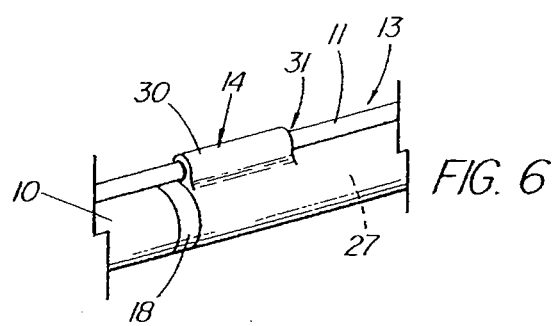
FIG. 6
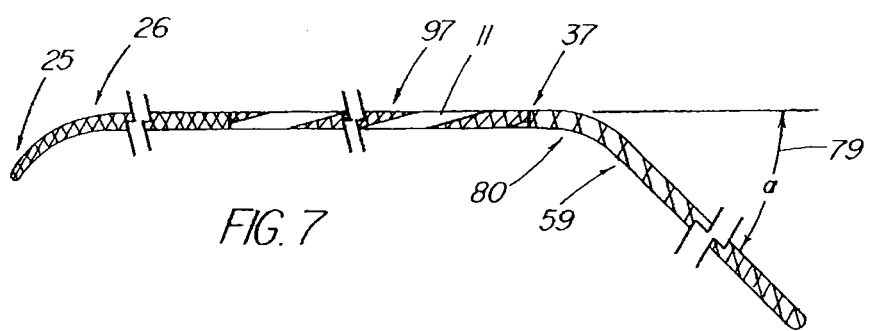
FIG. 7

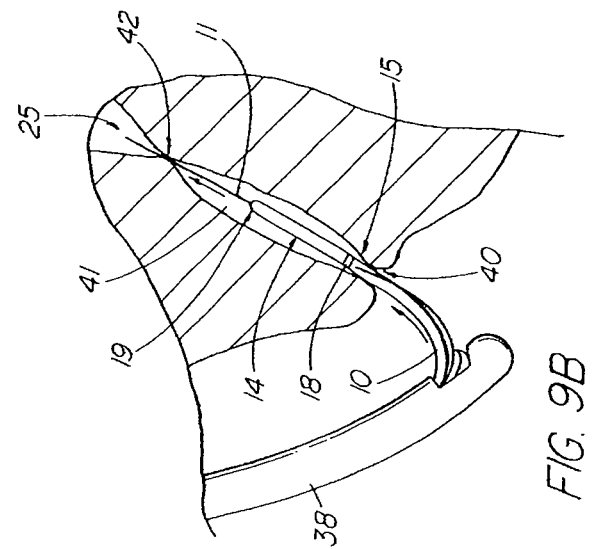
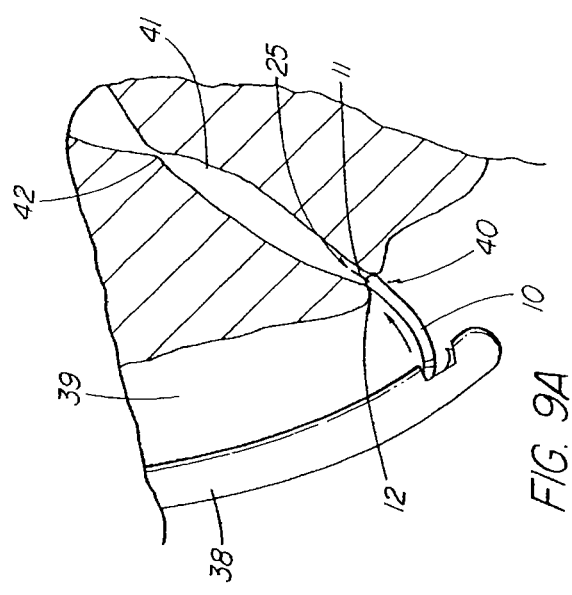

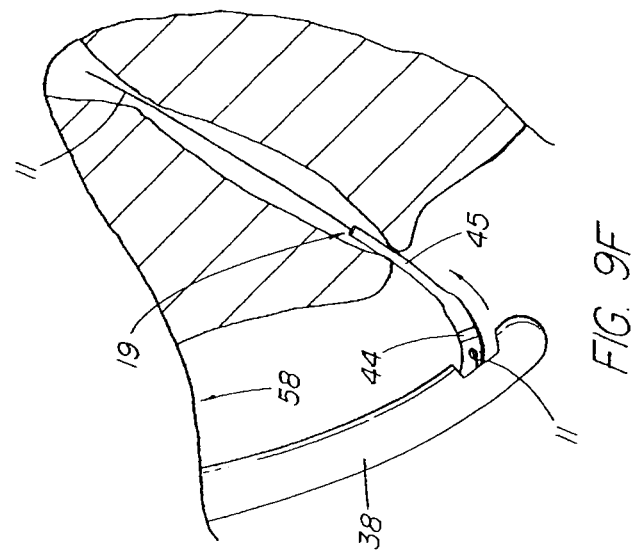
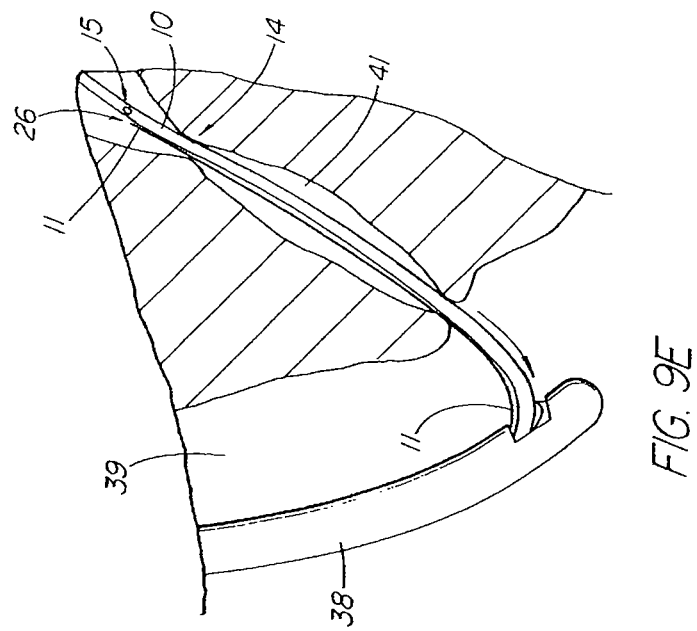
FIG. 9F
FIG. 9E

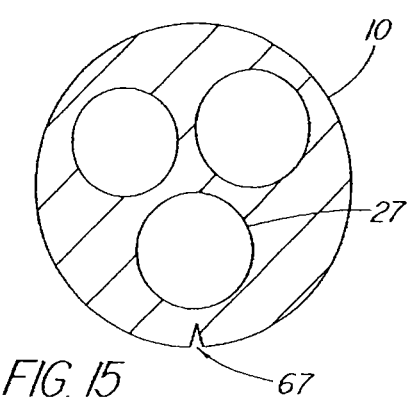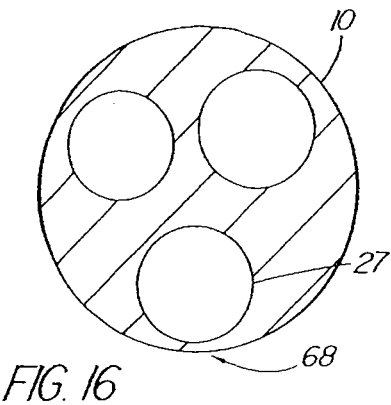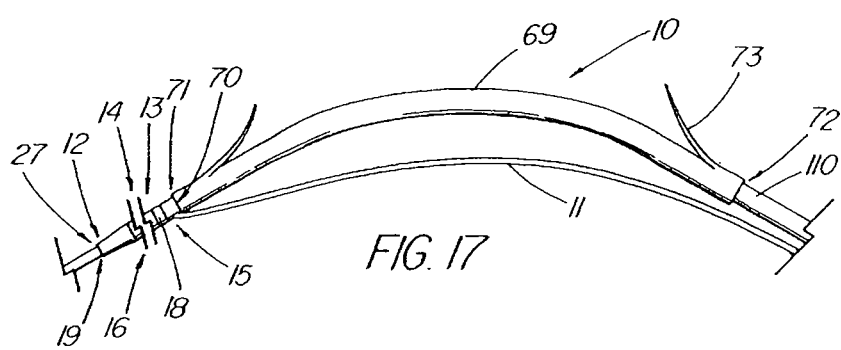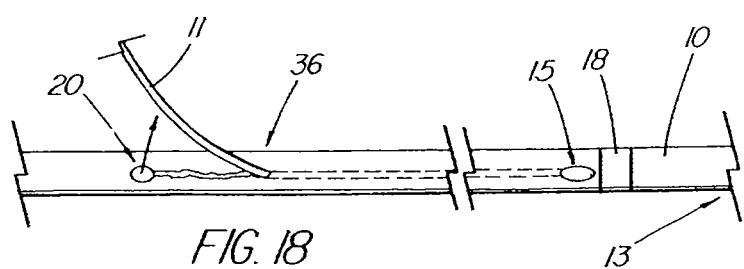

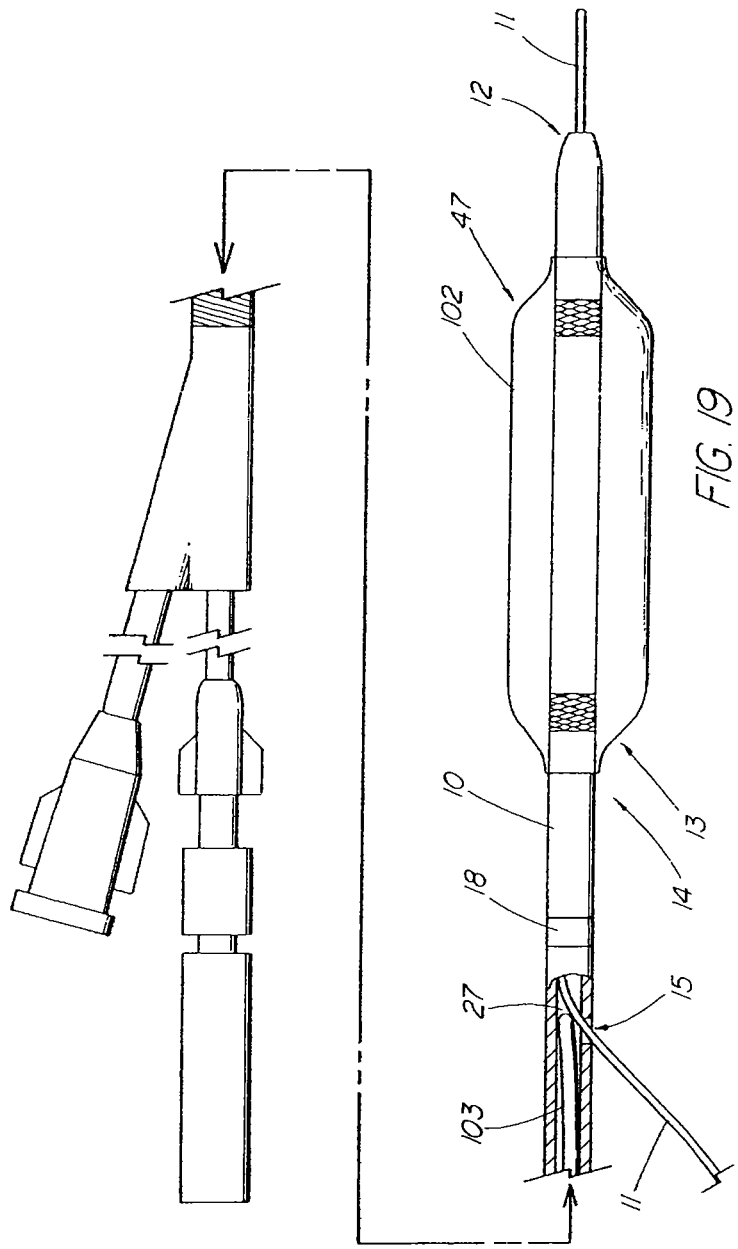

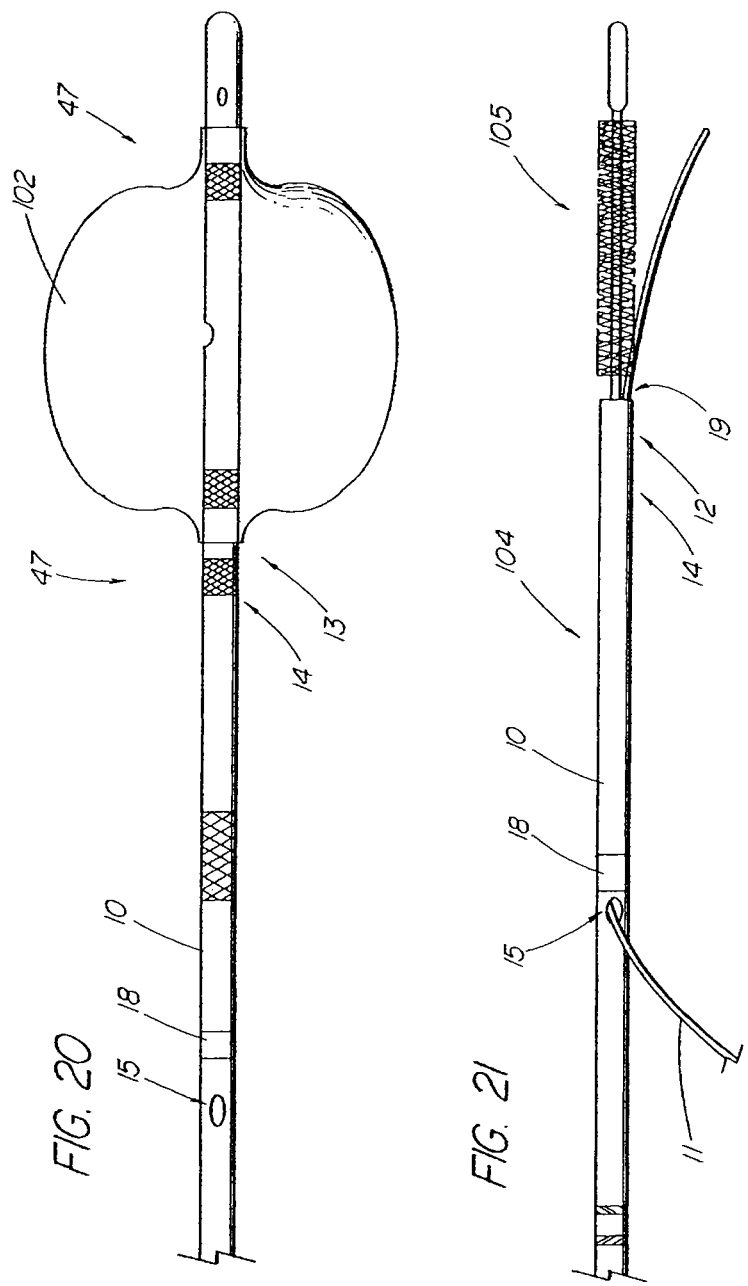

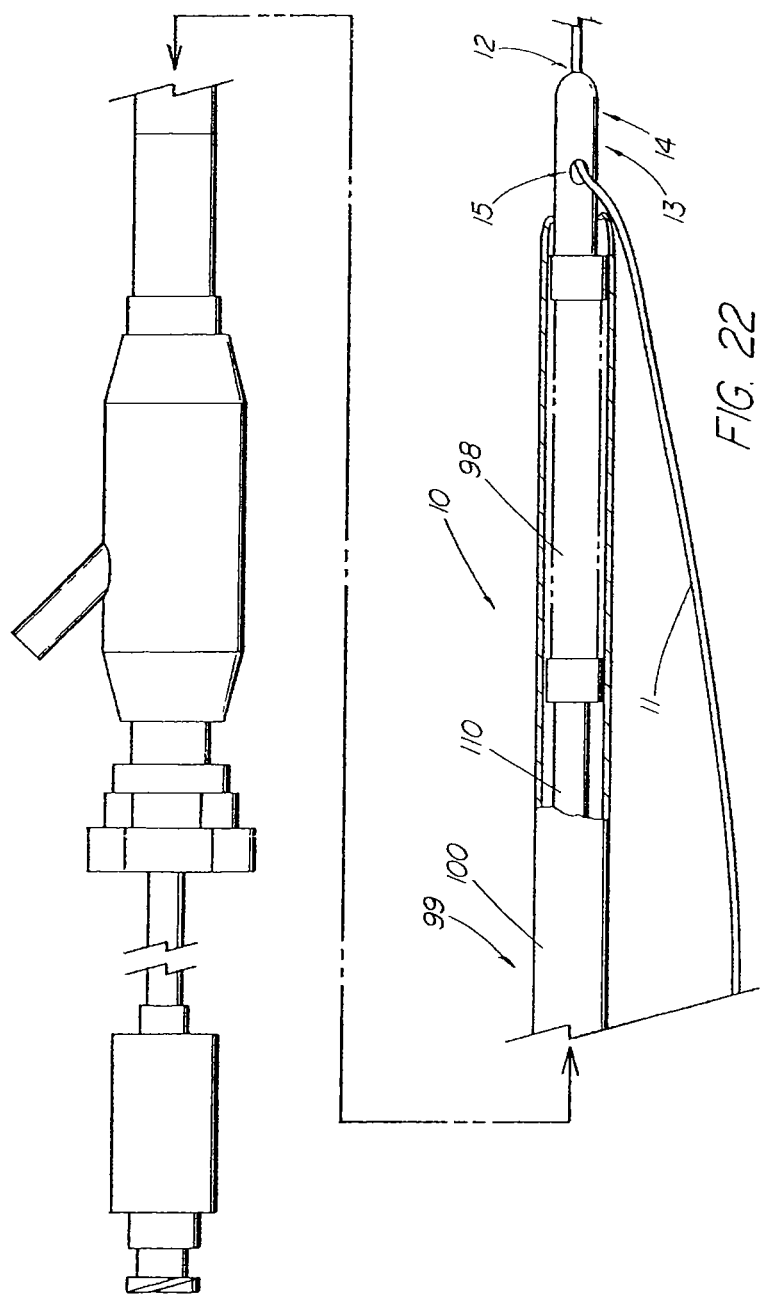

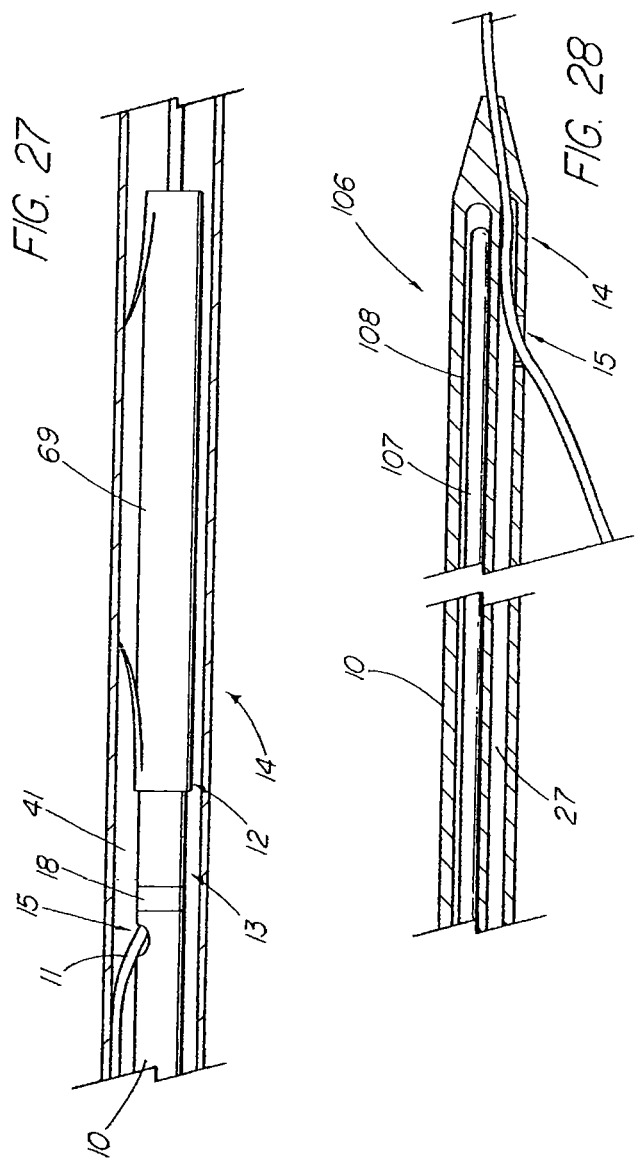

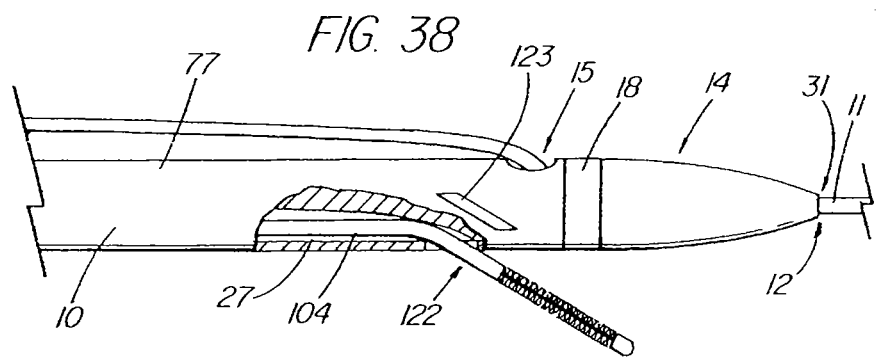
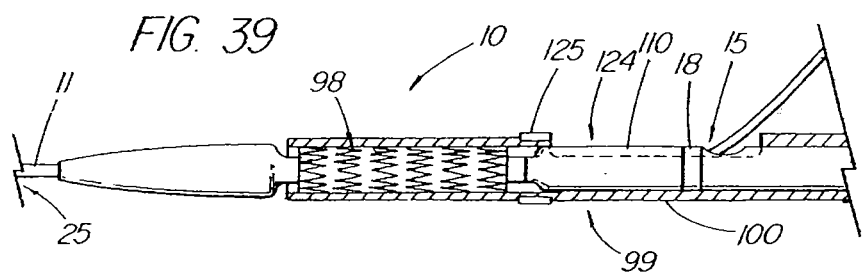
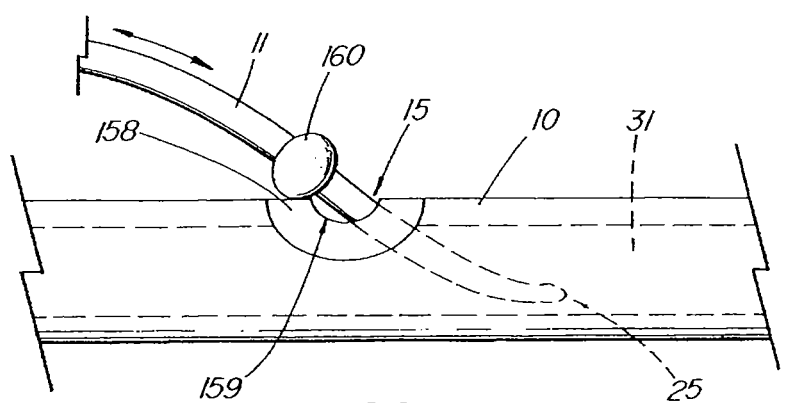

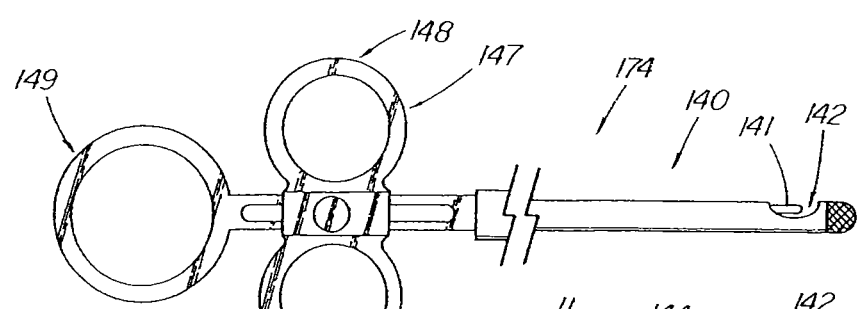
FIG. 48
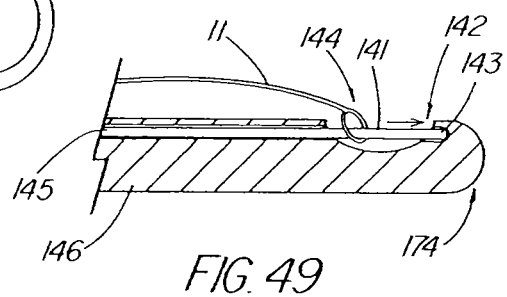
FIG. 49
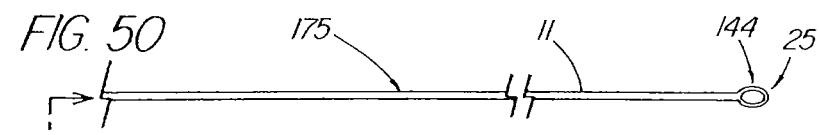
FIG. 50
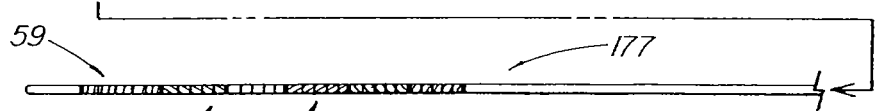
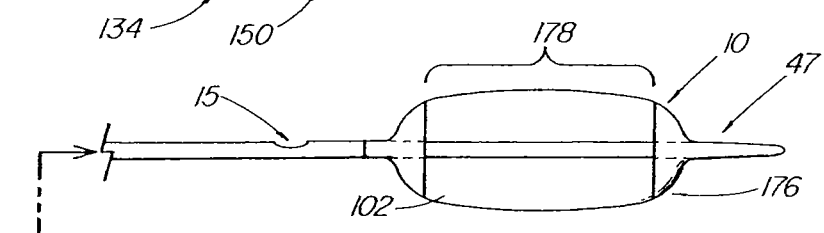
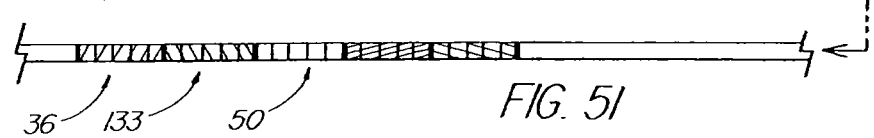
FIG. 51

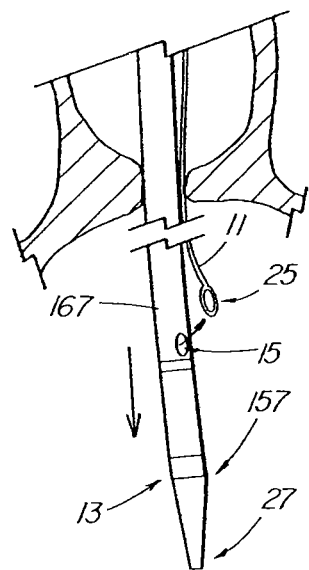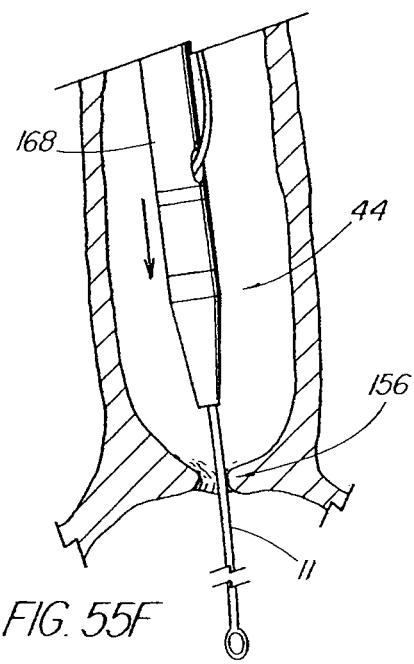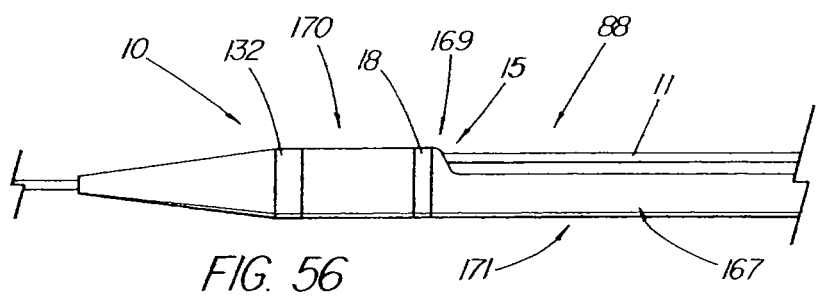

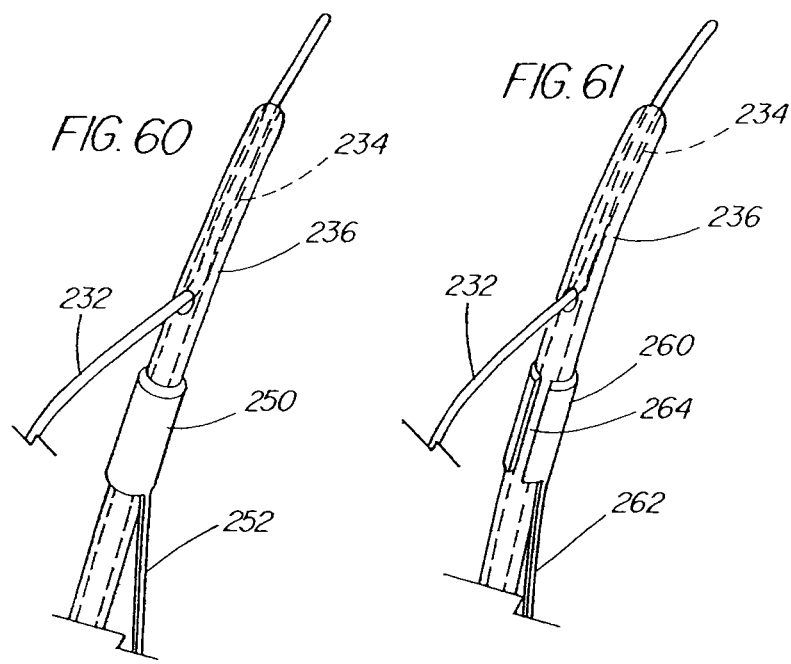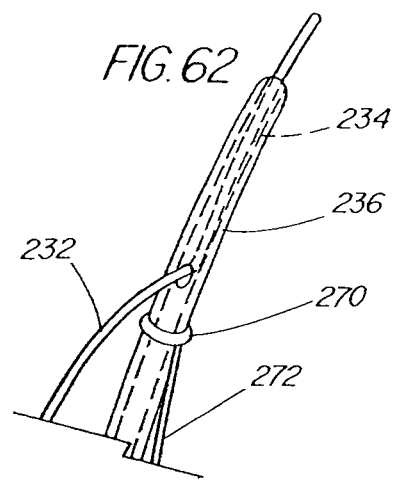

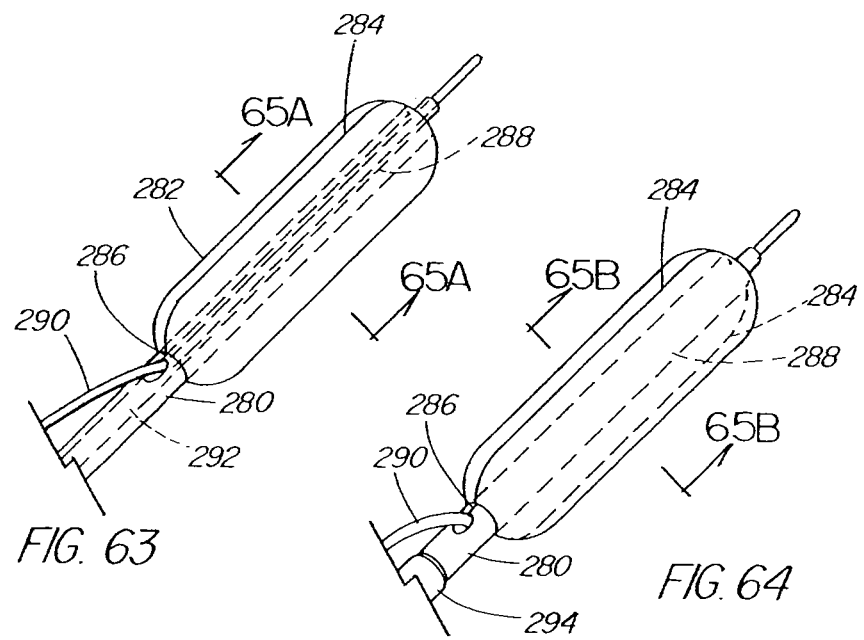
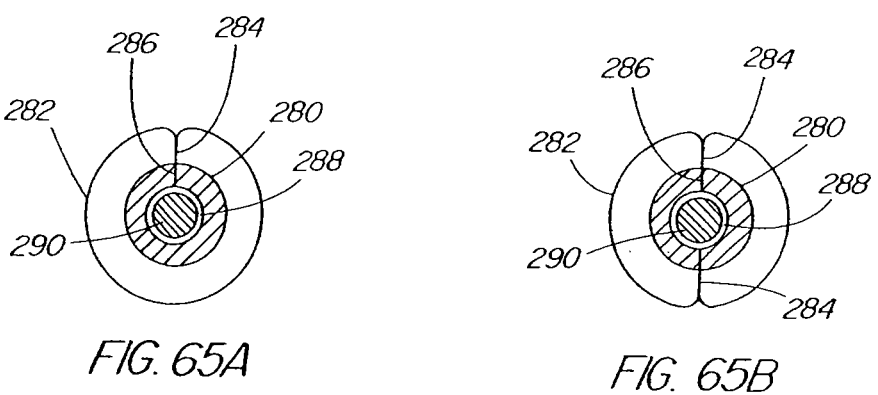

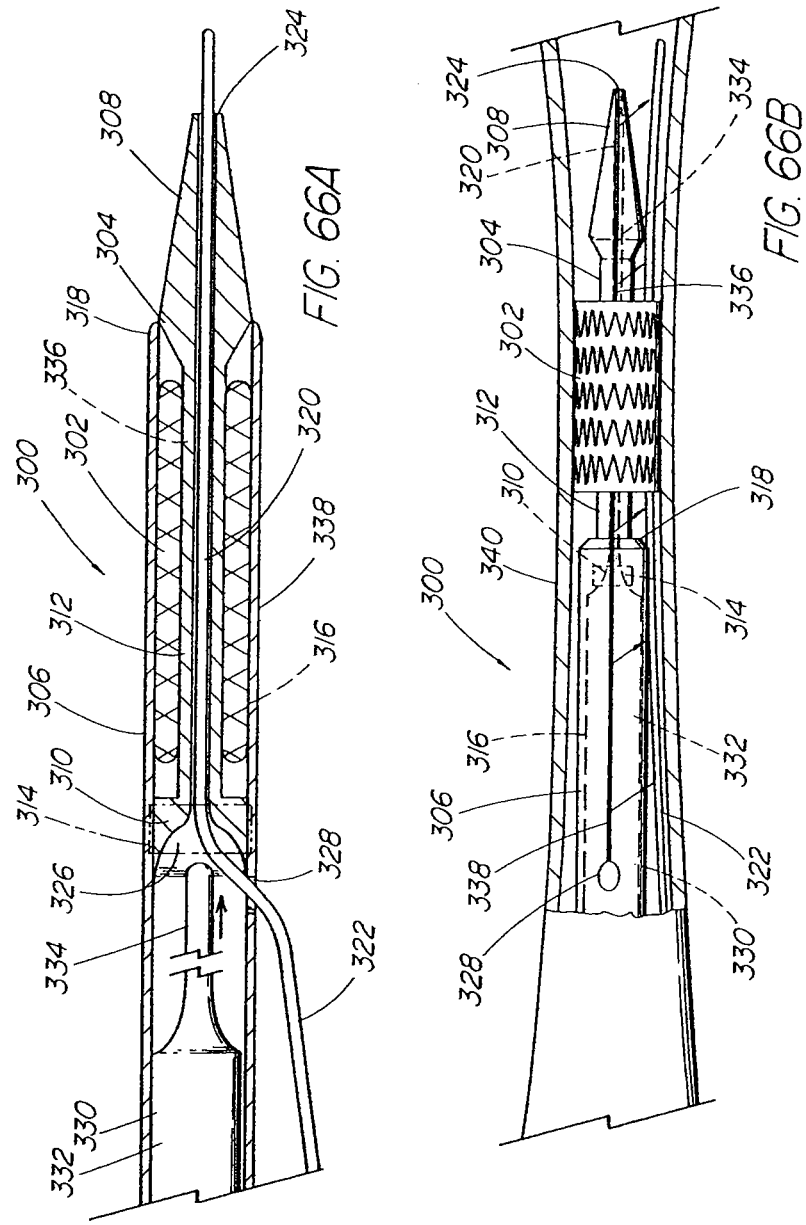

SYSTEM AND METHOD FOR INTRODUCING MULTIPLE MEDICAL DEVICES

CROSS-REFERENCE TO RELATED APPLICATIONS

This application is a continuation application of U.S. Non-provisional application Ser. No. 10/902,438, filed on Jul. 29, 2004, issued as U.S. Pat. No. 7,967,830 on Jun. 28, 2011, which claimed priority from U.S. Provisional application Ser. No. 60/491,408, filed Jul. 31, 2003, Ser. No. 60/563,968, filed Apr. 21, 2004, and Ser. No. 60/570,656, filed May 13, 2004, the entirety of which are each fully incorporated by reference herein.

TECHNICAL FIELD

This invention relates to medical devices, more particularly catheters and the like that are introduced into the patient over a wire guide.

BACKGROUND OF THE INVENTION

Minimally invasive medicine, the practice of gaining access into a blood vessel, duct, or organ using a wire guide to facilitate the subsequent introduction or placement of catheters and other medical devices, has been evolving since the Seldinger technique was first popularized during the late 1950s and 1960s. A significant advance was gaining the ability to exchange medical devices over a single indwelling wire guide without requiring displacement of the wire in the process and loss of access to the site. This 'over the wire' (OTW) exchange technique requires an extra long guide wire so that control over the wire could be maintained at all times during the procedure. To accomplish this, the portion of the wire extending out of the patient must be at least as long as the device itself so that a proximal portion of the wire could be secured at all times maintain longitudinal positioning, typically by an assistant standing well behind the physician. For example, endoscopic catheters that are used to access the biliary system are typically 200 cm or more in length, requiring a wire guide of more than 400 cm (e.g., 480 cm) to be long enough to remain in the duct during the exchange. To remove the catheter over the wire, the physician and an assistant must carefully make a series of well-coordinated, one to one movements between the exchange wire and device. The assistant pushes the wire the same amount as the physician pulls back on the catheter until the device is completely outside of the patient and the physician gains control over the wire at the port of the scope. The assistant then pulls the device off of the wire such that a second device can be fed back over the wire and into the patient to perform a second operation, requiring the same push-pull technique in reverse. This procedure requires a well-trained assistant, who actually is responsible for the advancement of the wire, instead of the physician. In biliary ERCP, this lack of wire guide control can be a disadvantage when cannulating the ampullary orifice because the techniques used are typically highly dependent on good verbal communication between the physician and assistant, and the experience of the latter.

Although the 'long wire' or OTW technique still remains a commonly used method of exchanging devices in the biliary system, a technique was developed which allowed for a much shorter wire guide and more physician control over the wire. Variously known as the 'rapid exchange,' 'monorail,' or 'short-wire' technique, it differs from the OTW technique in that instead of the device being introduced over the length of the wire guide, the wire guide is coupled for only a portion of the length of the catheter device. The device is fed over the wire guide, which then exits the passageway or a coupling portion of the catheter at a point between the catheter's distal end and the proximal portion via a port or channel formed in the side of the catheter, typically located within the distal portion of the device. This allows the physician to have control of the proximal or external portion of the wire at all times as it exits the patient or scope and reduces the need for coordinating device movements with an assistant. When the coupled portion exits the patient (or endoscope in the case of gastroenterological or other endoscopic procedures), the physician performs a short exchange (instead of the traditional long-wire exchange, which in biliary procedures, requires the assistant to stand well out of the sterile field in order to assist with the exchange). With certain other devices, the catheter is split or torn away to uncouple it from the wire as the catheter exits the patient. To introduce the device, the coupled portion of the catheter is advanced over the proximal end of the wire guide, while the physician is careful to maintain the wire in position so that its distal end is maintained within the work site and access is not lost.

Rapid exchange or short wire techniques have proven particularly desirable in coronary and vascular medicine whereby it is common for a sequence of procedures using multiple catheter-based devices to be performed over a single wire, such as stent placement following angioplasty. Another example of where short wire exchange techniques are often used is in endoscopic procedures performed in the pacreatobiliary system. Typically, an ERCP (endoscopic retrograde cholangiopancreatography) procedure is performed by introducing a catheter device from a duodenoscope through the ampullary orifice (Papilla of Vater) and into the biliary tree, which includes the bile duct, pancreatic duct, and hepatic ducts of the liver. The cannulation device, which typically comprises a sphincterotome/papillotome or ECRP catheter, is introduced into the biliary tree to perform a first operation, which could be diagnostic in nature, such as injecting contrast media, or for therapeutic purposes, such as enlarging the ampullary orifice. When a second medical operation is required, such as to remove a stone, open a stricture, sample tissue, etc., a second or peripheral device, e.g., balloon, basket, snare, biopsy brush, dilator, stent delivery catheter, etc., can be introduced over the original wire guide to perform a secondary therapeutic procedure.

While OTW techniques have permitted the exchange of devices, the development of short wire techniques has found acceptance by physicians who prefer to maintain greater control of the wire guide at the scope. Well-known examples of this rapid exchange technology are the devices comprising the MICROVASIVE RX BILIARY SYSTEM™ (Boston Scientific Corporation, Natwick, Mass.) in which the catheter portion of the devices include an internal lumen extending between a distal opening and a proximal side opening spaced 5-30 cm therefrom, depending on the device, thereby requiring an exchange of that length as the device is being removed over the 260 cm JAGWIRE® Guidewire guide developed for that system. An example of a sphincterotome of this system (AUTOTOME™ Cannulating Sphincterotome) is depicted in FIG. 1. Extending proximally from the proximal side opening, the lumen forms a 'C-channel' (shown in FIG. 2) that holds the wire guide within the catheter as the catheter portion is introduced into the scope, but allows the wire to be laterally pulled out of the channel to gain access of the wire at the biopsy port of the scope as the catheter is being removed from the scope (FIG. 3), so that a second catheter type device (e.g., balloon, basket, stent delivery catheter, etc.) can be subsequently fed over the proximal end of the wire. As the distal portion of the first device is exiting the scope, a short exchange is required (coordinated push-pull movements between the physician and assistant) that is similar in practice to that used in an OTW procedure, until the physician gains control of the wire and the assistant can pull off the first device without risking loss of access. The proximal end of the wire guide is typically secured to the scope during much of the procedure to prevent loss of access, but it must be disengaged from the scope to allow the exchange and removal of the catheter.

While the Microvasive system has offered modest time savings, more physician control of the wire, and placed less reliance on the skill of the assistant to help perform the exchange, a short exchange procedure is still required in which care must be taken to prevent loss of wire guide access to the duct, particularly since the wire guide cannot be secured to the scope during removal of the catheter. Because the wire guide resides in the channel of the catheter and the coupled devices are constrained together in the accessory channel, uncoupling must take place as the distal portion of the catheter exits the proximal end of the scope. The process is further slowed by the frictional resistance between the wire and catheter, which remains a problem in subsequent exchanges as devices are fed or removed over the wire residing in the catheter lumen or C-channel.

Having a C-channel extending along the catheter can result in certain clinical disadvantages. For example, the split in the catheter provides an entry point for blood and bile, a known source of viruses and bacteria, to enter the catheter lumen and migrate to the proximal end of the device where they typically leak out onto the floor and clothing of those involved in the procedure. The channel also represents a point of potential air leakage, which can compromise the ability to maintain adequate insufflation within the duodenum during the procedure. Another disadvantage of a C-channel is that it degrades the integrity of the catheter, which can be problematic in a cannulating device (such as a deflecting Sphincterotome) when attempting to push through or 'lift' the papilla to straighten the entry pathway into the duct, or when pushing through a stricture.

The current rapid exchange or short wire system also fails to address some of the shortcomings found in the traditional OTW method. For example, recannulation of the papilla is required when placing multiple plastic drainage stents side by side since the delivery system must be removed to disconnect the wire. Furthermore, existing devices do not offer the ability to place a second wire guide after the first one, such as to place stents in multiple ducts, since the catheter, which could otherwise serve as a conduit, must be removed from the patient and work site before it would have a free lumen for a second wire. Another disadvantage of current systems for exchanging biliary devices is the incompatibility between the two systems. Long wire devices lack the side access port for use with a short exchange wire and the MICROVASIVE RX BILIARY SYSTEM™ devices with C-channels are poorly configured for long wire exchange since once the C-channel has been breached during the first exchange, it is difficult to introduce a long wire through the proximal wire guide access port (which includes the open channel) and keep it from slipping from the channel as it is being introduced. Further, the C-channel is typically not compatible with smaller-diameter wire guides (less than 0.035") for the same reason. Incompatibility between systems means that physicians cannot take advantage of all of the choices available when selecting the best device and treatment for a particular patient.

What is needed is an improved short-wire system and technique for efficiently and reliably exchanging devices within a work site which is compatible with long wire exchange method and which addresses the other deficiencies described above.

SUMMARY OF THE INVENTION

The foregoing problems are solved and a technical advance is achieved in an illustrative system and method for introducing and exchanging multiple elongate medical devices, e.g., tubular members such as catheters and the like, over an indwelling guiding member, such as a wire guide, within a patient by remotely uncoupling the first device (primary access device) from the guiding member within the work site (defined as a lumen, duct, organ, vessel, other bodily passage or cavity, or the pathway leading thereto in which wire guide/guiding member access is maintained throughout a particular procedure or series of procedures), thereby facilitating the removal of the device and simplifying introduction of a secondary access device over the indwelling wire without an exchange of devices taking place outside of the patient. While the primary focus of this application is the exchange of devices within the pancreatobiliary system or elsewhere in the gastrointestinal tract, the system and method of remote uncoupling of devices within a work site can be adapted for any part of the body to perform any suitable procedure where the exchange of devices takes place over an indwelling guiding member. Examples include, but are not limited to the introduction and placement of balloons, stents, grafts, occluders, filters, distal protection devices, catheters for ablation, phototherapy, brachytherapy etc., prosthetic valves, or other instrumentation or devices into the vascular system, including the coronary arteries, peripheral arterial system (e.g., carotid or renal arteries), or venous system (e.g., the deep veins of the legs). Other exemplary sites include the genito-urinary system (e.g., bladder, ureters, kidneys, fallopian tubes, etc.), and the bronchial system. Additionally, the present system and method can be used for exchanging devices within body cavities, e.g., the peritoneum, pleural space, pseudocysts, or true cystic structures, via percutaneous placement and exchange through a needle, trocar, or sheath.

The basic system of devices for remote uncoupling comprises a guiding member, typically a wire guide. It should be understood that hereafter, the term 'wire guide' is used in the specification in a generic sense to include any device (e.g., small-diameter catheter, laser fiber, string, plastic beading, stylet, needle etc.) configured to perform the same function, although such a device technically may not be considered a wire guide (or 'guidewire') as the term is most commonly used in the medical arts. Remote uncoupling permits a shorter guiding member/wire guide to be used than for other short wire methods (e.g., rapid exchange), and thus hereafter, the methods described in this specification are referred to collectively as the 'ultra-short wire' technique, or depending on the work site, 'intraductal exchange' (IDE), 'intravascular exchange' (IVE), etc. The reason that the wire guide can be of a shorter length than traditional rapid exchange wire guides is that there is no exchange outside the patient. In fact, remote uncoupling allows for the exchange wire guide to be shorter than the devices being introduced since the devices are not removed over the wire. For example, the wire guide of the present inventive system of biliary devices (for use in a 145 cm channel duodenoscope) is typically 185 cm (minimum functional length of about 180 cm), as opposed to the 260 cm wire guide typically used for the Microvasive 'rapid exchange' procedures in which a 5 to 30 cm external exchange must be performed each time, depending on the device used. The shorter wire is easier to manipulate by a single operator and helps prevent it from contacting non-sterile surfaces, such as the floor, patient bed, instrument table, imaging unit, etc. The 185 cm length still permits most external changes to be performed, if necessary. To accommodate a longer wire for exchanging a device otherwise not compatible with the system, an optional coupling mechanism on the proximal end of the wire can be included to engage a wire guide extender portion to lengthen the wire (e.g., to 260 or 480 cm) and permit a traditional exchange to take place.

Coupled to the guiding member/wire guide is a first elongate medical device (the primary access device), typically a tubular member or catheter device, which includes a coupling region, such as a passageway or lumen, external channel, outer ring, or other interface area, located about the distal portion and which is configured to receive a portion of the wire guide such that both devices can comprise a releasably coupled pair while operating within a work site. The coupling region may be an integral part of the elongate medical device or may located about a separate element disposed therewith (e.g., an elongate engagement member), which for purposes of this application is considered part of the elongate medical device. A separate elongate engagement member can provide a primary or secondary means of releasably securing the wire guide and catheter device until they are to be repositioned or uncoupled. The elongate engagement member, typically but not necessarily disposed within the passageway of the tubular member, can further comprise the coupling region as well. Preferably, the primary access devices used with this system have a closed or self-sealing passageway extending to the proximal (external) portion of the device (instead of an open or split channel) such that the system can be readily converted to introduce a long wire if a long wire-compatible device is selected. Further, the devices of this invention are configured for traditional short wire exchange back over the wire, if so desired, or when remote uncoupling becomes problematic (e.g., due to unexpected anatomical constraints).

In a first aspect of the invention, the system further includes an alignment indicator system, such as a system of indicia (e.g., radiopaque markers, external markings, endoscopic markings, etc.) located about the wire guide and/or first elongate medical device that can be utilized by the operator in locating the position of the distal end or distal portion of the wire guide relative to the proximal end of the coupling region, such as at a side access port or aperture (e.g., scive) through which the wire exits. The alignment indication system advantageously allows the physician to control when the two devices are coupled or uncoupled within the work site and helps provide confirmation that uncoupling has occurred. Without the ability to receive such confirmation, it would be extremely difficult for the physician to attempt, with any confidence, the uncoupling of the catheter from the wire guide (e.g., under fluoroscopic guidance) without knowing when uncoupling has occurred or is about to occur. Depending on the location or work site within the body and the device being delivered, an attempt to 'blindly' uncouple devices can lead to loss of wire guide access, especially if the device is prematurely withdrawn with the wire guide still engaged. Furthermore, the amount of relative movement between the device and the wire guide required to ensure that uncoupling had occurred would generally be much greater than if indicia were utilized, thus increasing risks such as the wire guide being withdrawn too far and access lost or encountering situations where there is insufficient space within the work site left for uncoupling to take place. Typical rapid exchange devices are not configured with the necessary radiographic or other appropriate indicia since the exchange procedure is intended to take place outside of the patient. The external exchange is a slower process and dictates removal of the first catheter before another catheter or wire guide can be advanced to the work site over an existing device (which always must be a wire guide or guiding device in traditional rapid exchange).

A first series of embodiments of the system of indicia includes radiographic or ultrasonically reflective markings located about one or more of the devices which are used by the operator under an appropriate external guidance system (fluoroscopy, MRI, CT scan, x-ray, ultrasound, etc.) to determine the state of alignment and engagement between the primary or secondary access device and guiding device. A first example comprises radiopaque or high-density bands, markings, etc., located on the distal portions of the wire guide and first elongate medical device. In particular, the distal tip of the wire guide includes a radiopaque portion that typically comprises at least the length of the coupling region of the first elongate medical device, which itself includes a radiopaque marker, such as a band comprising iridium, platinum, or other suitable material, located about the proximal end of the coupling region (e.g., at, or just distal to the side access port), thus allowing the operator to know when the distal tip of the wire is nearing or has exited the point of the catheter at which the devices become uncoupled or separate within the work site. Additionally, other radiopaque markers may be present that are generally not used to assist in remote uncoupling, such as at the distal end of the catheter or indicia used for stent or balloon placement.

A second series of embodiments of the system indicia comprises directly viewable indicia located about the proximal portions of the wire guide and the tubular member to which it is coupled during the procedure. In one example, the wire guide comprises a visually distinctive alignment point, such as a single mark (e.g., colored band) or a transition point between different colored and/or patterned regions of the wire guide outer coating, which when aligned with a specified first marking on the proximal portion of the elongate medical device, indicates that the distal ends of the wire guide and tubular member are in alignment with respect to one another. The catheter further includes a second mark that represents the disengagement point, that when aligned with the designated alignment marking of the wire guide, is indicative that the two devices are about to or have uncoupled or disengaged with the distal tip of the wire guide having exited the coupling region. Preferably, the first (distal) and second (proximal) markings on the proximal portion of the catheter are located within a region that remains external of the patient or scope during a procedure and are spaced apart by the same distance as the length of the coupling region. For very short coupling regions (e.g., rings), a single mark on the catheter may be preferable to indicate disengagement, if proximal indicia are to be used.

A third series of embodiments of the system of indicia include markings that are configured to be viewable by a fiberoptic endoscope or videoendoscope (e.g., duodenoscope, gastroscope, bronchoscope, ureteroscope, etc.). In devices configured for accessing the pancreatobiliary system, the indicia comprise a marking located on both the wire guide and elongate medical device disposed within an intermediate portion of each, which is typically located distal to the viewing lens or video chip of the scope, but proximal to the ampullary orifice during a typical procedure, such that they can be aligned by using the video monitor (or viewing port) to ascertain that uncoupling within the duct has occurred. The device may include other endoscopic indicia useful during the remote uncoupling procedure. For example, a biliary catheter may include a depth marking at a designated distance from the catheter tip (e.g., 10 cm) which when buried within the papilla, indicates that IDE can be performed safely within the duct without risking loss of wire guide access. Furthermore, the distal portion of the wire guide can be distinctive in appearance (e.g., black) as a visual cue to warn the physician if the tip is in danger of pulling completely out of the duct, which would require recannulation of the papilla. The second and third system of indicia do not require external imaging, thus the physician can advantageously limit the time that the patient is exposed to fluoroscopy. For example, fluoroscopy can be used only at selected, critical times during the procedure with at least one of the other types or indicia being used elsewhere for alignment guidance.

In addition to the use of visual indicia to confirm whether the wire guide and first elongate medical device (and subsequent devices) are engaged or uncoupled, the present invention includes other types of alignment indication systems, such as a tactile system that includes one or more protuberances and/or indentations along one or more of the devices or the endoscope accessory channel port to allow the physician to 'feel' or sense the point where disengagement has occurred or is imminent due to the discrete point(s) of increased resistance between the device as they move relative to one another. Magnets can be a part of a tactile system as well. Other embodiments of the alignment indicator system include sensor-based systems in which a sensor located within the system, such as along the catheter or endoscope channel/port, detects a calibrated location elsewhere in the system (e.g., the wire guide or catheter) and emits or provides a signal or cue (e.g., electrical signal) that is relayed to the operator in the form of an audio or visual alert that warns the operator that the devices have or are about to become uncoupled. The alignment system can comprise a single system or means for alignment, or any combination of visual and non-visual indicators.

In a second aspect of the invention, a method is provided for uncoupling the first elongate medical device from the wire guide while both are still dwelling within the work site (i.e., the basic ultra-short wire technique). Both devices are introduced into the work site, using a standard introduction method and introducer member such as an endoscope, introducer sheath, etc., with the wire guide engaged through the coupling region of the medical device being introduced. In one embodiment for use in the pancreatobiliary system, the coupling region comprises a passageway within the distal portion of the catheter, such as the distal 6 cm thereof, with the wire guide exiting at that point through a side access port (e.g., scive) such that the wire guide coextends along the outside of the proximal portion of the catheter as both reside side by side along the introduction pathway, which in the biliary embodiment comprises the channel of the duodenoscope. For example, a wire guide or primary access device, such as a sphincterotome, needle knife, ERCP catheter, etc., may be introduced first to cannulate the duct, with the primary access device being subsequently advanced over the wire to perform a first medical operation that is diagnostic and/or therapeutic in nature. During this time, the wire guide is preferably secured in place by attaching the proximal portion to the endoscope via a locking device, clip, other means located about wire guide entry port (biopsy port), thus fixing its position longitudinally to assist with maintaining access to the work site. Once the first device has performed its intended operation (inject contrast media, ablate the sphincter, etc.), the operator preferably uses the radiographic, endoscopic, and/or proximal system of indica to provide visual guidance during repositioning of the devices to permit disengagement. One technique (referred to herein as 'device IDE') includes advancing the primary access device over the stationary wire guide until uncoupling has occurred. A second technique (referred to herein as 'wire guide IDE') includes withdrawing the wire guide while maintaining the primary access device in a stationary position until the alignment indicia indicates that uncoupling has occurred. A third technique would involve a combination of the device and wire guide IDE. Also, there typically is a characteristic 'whipping' action of the radiopaque wire guide tip portion upon exit from the passageway that is viewable under fluoroscopy which also provides a visually distinctive indicator of uncoupling.

When the physician, using at least one component of the alignment indicator system, has determined that the tip of the wire guide has disengaged from the coupling region of the primary access device, the first device can be easily removed by merely pulling it back out of the endoscope accessory channel (or introducer sheath in the case of vascular or certain other non-endoscopic applications). Removal is greatly facilitated by the elimination of friction which would have otherwise existed between the wire guide and catheter if the wire resided within the channel or lumen. Although some of the aforementioned MICROVASIVE RX™ biliary devices (e.g., the AUTOTOME™ sphincterotome) include a side port within the distal portion, all of the devices lack the combination of indicia that make a remote or intraductal exchange clinically practical or even possible. Furthermore, those devices that include an open channel extending proximally of the side access port cannot be uncoupled within the duct or work site regardless of the lack of indicia since the proximal portion of the wire guide tends to 'seek' and reenter the channel when both devices are residing within the accessory channel of the scope. Thus, remote disconnection is rendered impossible without some means to releasably disengage the wire from the channel.

After the catheter and wire guide are uncoupled, the proximal end of the wire is available for a third elongate medical device (e.g., a secondary access device or a second device that is the same as the first) to be advanced thereover to the work site. In one example of the method, the proximal end of the indwelling wire is fed through the distal opening and out of the side access port of the secondary device, which is then advanced to the work site. If after the second medical operation using the secondary device, another secondary device is required for another operation, the first secondary device (third medical device) is removed from the wire guide and the patient, and the wire guide is available to provide access for a fourth device in the same manner as the first two.

In a variation of the present method, the primary access device may be left in place at the work site after disengagement with the wire guide to serve as an introduction pathway or conduit for a second wire guide, such as for a procedure where two branches of a duct or vessel are to be cannulated. An example of such a procedure is when a stent must be placed in two different ducts draining separate lobes of the liver. The second wire guide is typically introduced through a proximal wire guide port or hub of the first device, typically disposed about the handle portion, the port communicating with the passageway. This technique typically requires a long-wire exchange of the catheter. A second option is to introduce the wire through a proximal side access port (e.g., a scive) formed through the wall of the tubular member so that full control of the wire is maintained. In this embodiment, the catheter walls are configured to be splittable between the proximal and side access ports, or include an open or self-sealing channel through which the wire guide can be stripped out toward the distal portion of the device such that a long exchange is not required. Removing or stripping the wire guide laterally from the passageway can be done by any well-known means, such as scoring or structurally weakening a wall of the catheter, using a splittable, isotropically oriented catheter wall material (e.g., PTFE), incorporating a sealable or locking seam therealong, or by thinning the wall and/or using a material that allows the wire guide to split the wall and form its own exit pathway when sufficient force is supplied. Alternatively, a wire guide that includes a coupling region, such as an attached sleeve, can be used to couple to a standard wire guide that is already indwelling, or both wires can be coupled together and advanced through the passageway of the elongate tubular member.

After gaining access to the passageway by one of the aforementioned routes, the wire guide is guided under external imaging, such as fluoroscopy, into the desired location. Optionally, if the first device is a sphincterotome or other type of deflectable catheter, the operator can manipulate the shape and orientation of the catheter tip portion to help guide the tip of the second wire guide into the opposite (or side) branch of the duct or vessel. Orientation within the work site can be facilitated with a rotatable handle to direct the tip. Furthermore, it has been demonstrated that certain shorter wire guides, such as the illustrative 185 cm biliary wire guide of the present invention, are sufficiently torqueable such that an operator can simply rotate the wire with his or her fingers to achieve similar results in most instances.

In another aspect of the invention, primary access devices further include an elongate engagement member configured to releasably engage with the wire guide within or about the coupling region (e.g., the distal passageway of the tubular member). Embodiments include using a flexible wire stop (e.g., a nylon stylet) configured to wedge the wire guide within the passageway when in the fully advanced position, and a thread-like member (e.g., suture) that ensnares the wire guide and provides tension to maintain it in a longitudinally secure position relative to the tubular member. When an elongate engagement member is not used during introduction, such as when secondary access devices are being introduced over the already indwelling wire guide, a stiffening stylet may be optionally maintained in the passageway of the tubular member to add rigidity to the device during introduction and/or for advantageously traversing scives in the tubular member, such as the side access port, to prevent kinking thereabout.

In still another aspect of the invention, the system of devices adapted for remote uncoupling or ultra-short wire techniques includes a delivery catheter for plastic tubular drainage stents and a technique for deployment that allows for placing multiple stents side by side within the bile duct using a single cannulation procedure. By placing the side access port on the inner carrying member (over which the stent is mounted) at a point distal to the stent, the wire guide can be uncoupled within the duct and the stent deployed without having to withdraw the entire system, including the wire, in the process. The junction between the inner carrying member and wire guide can be advantageously used to 'catch' the stent when the inner member is pulled back, thus allowing the entire delivery system, including the stent, to be pulled back within the duct. This feature, which is not present in other stent delivery systems, is especially important to address situations when the stent is advanced too far into the duct and needs to be repositioned. After the stent is in the correct position for deployment, the inner carrying member is advanced and/or the wire guide withdrawn to uncouple the two, allowing the inner carrying member to be withdrawn through the stent and from the duct while the wire guide remains behind for a second stent delivery catheter (and additional stents) to be advanced into the duct and placed along side the first stent. Pigtail stents and others that include shaped distal portions for anchoring can be temporarily straightened during delivery by the wire guide which traverses the coupling region.

In still another aspect of the invention, the wire guide can be placed through the mouth by dragging or carrying the wire down using a endoscope and guide wire carrying mechanism that either resides in the channel of the scope and engages the wire guide about the scope tip, or attaches to (or co-extends with) the scope and engages the wire guide alongside. The treatment site, such as the gastroesophageal (GE) junction, is visualized and the distance to the mouth is measured using scale indicia located on the proximal portion of the scope. The wire guide, still coupled to the wire guide carrying mechanism, is then advanced a known distance (e.g., 10 cm) past the treatment site and into the stomach where uncoupling takes place following treatment. The wire guide includes a reference marking (e.g., at 10 cm) which lies at a known reference point relevant to treatment, such as the GE junction. The proximal portion of the wire guide preferably includes scale indicia, such as different colored bands or intervals (e.g., 5 cm) having different numbers or types of markings that reference a particular distance (typically using non-numerical indicia) to the reference mark at the GE junction. With the wire guide in position, the operator advances a primary access device, such as a dilator, PDT balloon, achalasia balloon etc., using corresponding indicia on the proximal portion thereof that align with that of the wire guide to guide placement of the device to the desired treatment site, such as the GE junction. If a secondary access device is required, such as a larger dilator, the first device is advanced into the stomach over the wire and uncoupled so that the wire becomes available for the next device to be fed thereover. Carrying the wire outside of the scope to a treatment site, which may also include the jejunum or other portions of the gastrointestinal tract, advantageously provides a means for placing devices larger than scope accessory channel, while still retaining the benefit of endoscopic navigation within the patient.

In still another aspect of the invention, the method and system of devices adapted for remote uncoupling or ultra-short wire techniques includes a separating member that is utilized to uncouple or separate the exchange wire guide from the first elongate medical device (the primary access device). The separating member comprises an elongate member that is configured to engage the side of the exchange wire guide and force the exchange wire guide out from the coupling region lumen of the first elongate member. In one embodiment, the separating member comprises a separating wire guide that is inserted into and through the lumen of the first elongate member until it engages the portion of the exchange wire guide that is disposed within the lumen of the first elongate member. Further advancement of the separating wire guide forces the exchange wire guide out through the wall of the first elongate member. The coupling region of the first elongate member may include an open channel, a split, a perforation, or a weakened area along the shaft wall to facilitate removal of the exchange wire guide out from the lumen of the first elongate member. In another embodiment, the separating member comprises a separating catheter that is slid along the exterior of the first elongate member until it engages the portion of the exchange wire guide that exits the lumen of the first elongate member. Further advancement of the separating catheter forces the exchange wire guide out through the wall of the first elongate member.

BRIEF DESCRIPTION OF THE DRAWING

Embodiments of the present invention will now be described by way of example with reference to the accompanying drawings, in which:

FIG. 1 depicts a perspective view of a prior art sphincterotome adapted for short-wire exchange;

FIG. 2 depicts a cross-sectional view taken along line 2-2 of FIG. 1;

FIG. 3 depicts the device of FIG. 1 being used with an endoscope;

FIG. 5 depicts a cross-sectional view of the distal portion of the embodiment of FIG. 4 and illustrative wire guide coupled thereto;

FIG. 6 depicts a side view of an embodiment of the present invention wherein the coupling region comprises an external channel;

FIG. 7 depicts a side view of a wire guide in which the proximal portion is oriented at an angle relative to the distal and intermediate portions;

FIGS. 9a-f depict the steps of an example of the present method in which multiple catheter devices are exchanged over a guide wire within the common bile duct;

FIGS. 15-16 depict cross-sectional views of sphincterotome catheters comprising a splittable wire guide passageway;

FIG. 17 depicts a side view of a biliary stent and delivery catheter of the present invention;

FIG. 18 depicts a side view of an embodiment of the present invention comprising a splittable region in the tubular member;

FIG. 19 depicts a side view of a dilation balloon of the present invention;

FIG. 20 depicts a side view of an extraction balloon of the present invention;

FIG. 21 depicts a side view of a biopsy device of the present invention;

FIG. 22 depicts a side view of a self-expanding prosthesis delivery apparatus of the present invention;

FIG. 27 depicts a cross-sectional view of a stent and pusher apparatus of the present invention;

FIG. 28 depicts a cross-sectional view of radioactive seed delivery apparatus of the present invention;

FIG. 38 depicts a partially sectioned view of an introducer member of the present invention;

FIG. 39 depicts a partially sectioned view of a delivery catheter of the present invention;

FIG. 40 depicts a side view of and embodiment of the present invention comprising a tactile alignment indication system;

FIG. 48 depicts a side view of a wire guide carrying mechanism of the present invention;

FIG. 49 depicts a cross-sectional view of the distal portion of embodiment of FIG. 48 engaging a loop tip wire guide;

FIG. 50 depicts a side view of the loop tip wire guide of FIG. 49;

FIG. 51 depicts a side view of a photodynamic therapy balloon of the present invention;

FIG. 55a-f depicts steps of esophageal dilation using the present method;

FIG. 56 depicts a side view of an dilator having a reduced diameter portion proximal to the side access port;

FIG. 60 depicts a side view of an alternative method of separating a wire guide from a catheter utilizing a variation of an external separating member;

FIG. 61 depicts a side view of an alternative method of separating a wire guide from a catheter utilizing another variation of an external separating member;

FIG. 62 depicts a side view of an alternative method of separating a wire guide from a catheter utilizing another variation of an external separating member;

FIG. 63 depicts a side view of an alternative method of separating a wire guide from a balloon catheter utilizing an internal separating member;

FIG. 64 depicts a side view of an alternative method of separating a wire guide from a balloon catheter utilizing an external separating member;

FIGS. 65a-b depict alternative cross-sectional views of the balloon catheters of FIGS. 63-64;

FIGS. 66a-b depict an alternative stent delivery device utilizing an internal separating member to deploy the stent and separate the wire guide from the delivery catheter;

DETAILED DESCRIPTION

Figure 4:
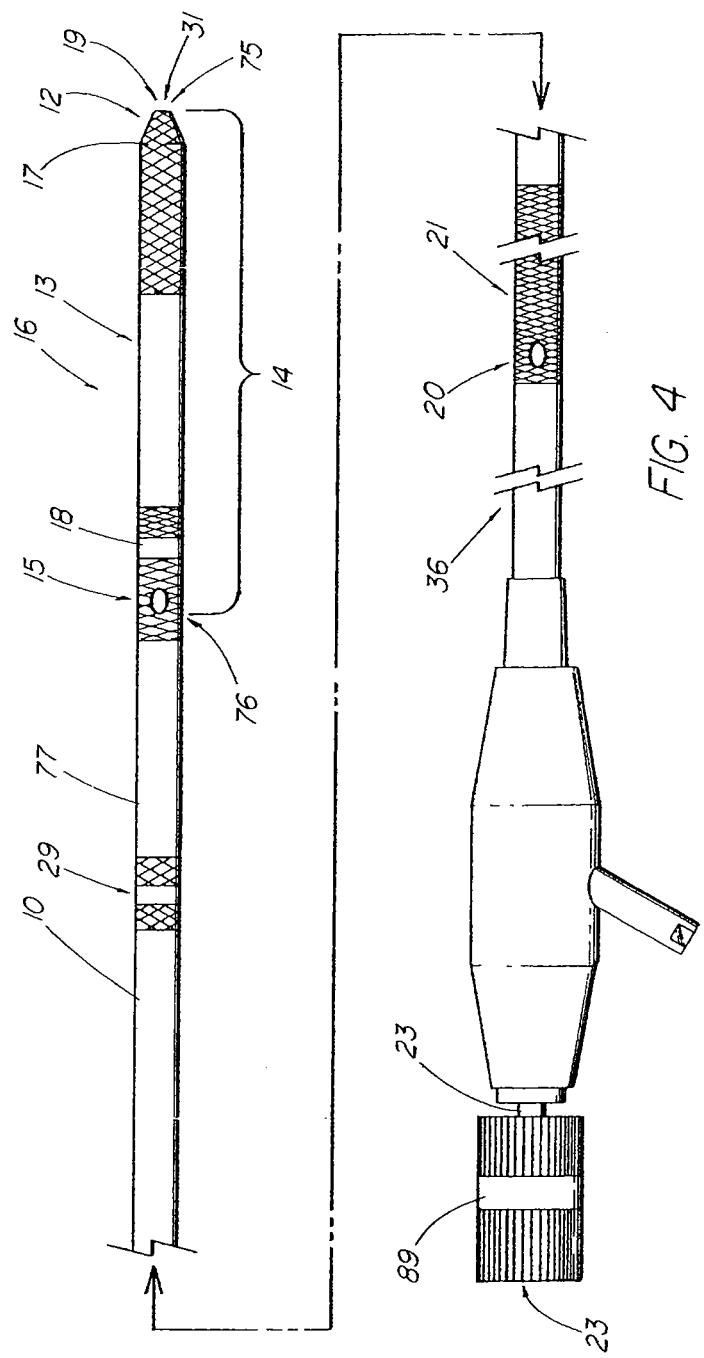
FIG. 4 depicts a side view of an illustrative catheter configured for use in the illustrative system and method.
Figure 57:
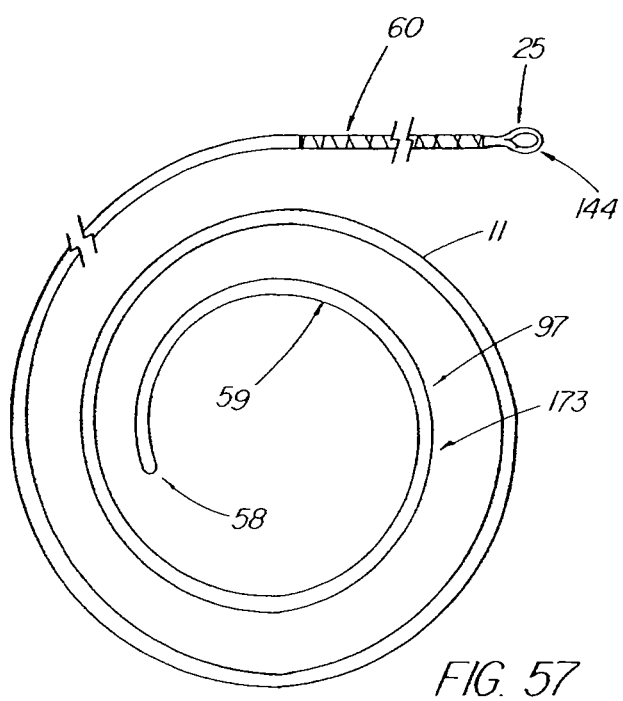
FIG. 57 depicts a wire guide of the present invention that includes a lubricious intermediate portion.

An illustrative system and method for introducing a series of medical devices over a wire guide into a patient by remotely uncoupling the first device from the wire guide inside of the patient without utilizing a long wire or standard short wire exchange procedure is embodied in FIGS. 4-57. A first exemplary embodiment of the system is depicted in FIGS. 4-5, which comprises a first elongate medical device 10, such as the illustrative tubular member 77 or catheter that includes features similar to the GLO-TIP II® E.R.C.P. Catheter (Wilson-Cook Medical, Inc.), the catheter further including a coupling region 14 having a first, distal end 75 (oriented toward the distal end of the device), a second, proximal end 76, and an interconnecting passageway 31 sized and configured to receive a standard-diameter exchange wire guide 11 (e.g., METRO® Wire Guide; Wilson-Cook Medical, Inc.) or other guiding device suitable for coupling to the first elongate medical device 10. The coupling region 14, generally located about the distal portion 13 of the tubular member 77 (first elongate medical device 10), may be coincident with the distal portion of the main passageway 27 (as depicted) or separate therefrom. The distal portions 13,60 of the first elongate medical device 10 and the wire guide 11, to which the former is coupled via the coupling region 14, are generally defined as the portion of each that are disposed within the work site during the medical operation and the subsequent uncoupling of the two devices. For purposes of this disclosure, the work site is defined as the lumen, duct, organ, vessel, other bodily passage/cavity, or the pathway leading thereto, in which wire guide access is maintained to perform a particular medical procedure/operation or series of procedures. For example, in a procedure involving the biliary system, the work site is considered the common bile duct, including the pancreatic duct and the ducts extending into the lobes of the liver.

The coupling region is configured to permit the first elongate medical device 10 to be co-introduced over the wire guide (either sequentially or together) into the work site in a coupled state (e.g., with the wire guide 11 traversing the passageway 27 of the first device 10) such that the proximal portion 59 of the wire guide exits the passageway and is external to the tubular member 77 as the wire guide 11 and tubular member exit the patient or scope. Like traditional forms of short wire or rapid exchange, this gives the physician more control over the wire at that point. In the illustrative coupling region 14 of FIGS. 4-5, the first end 75 thereof comprises a distal opening 19 in the tubular member 77, and the second end 76 comprises a side access port 15 or scive traversing the side wall of the tubular member 77 and located approximately 6 cm from the distal end 12 of the tubular member. The illustrative coupling region 14 is located within the distal portion 13 of the first elongate medical device 10 with the coupling region passageway 31 comprising the distal portion of the main wire guide passageway 27. The range of lengths of the coupling region 14 or the distance of the side access port 15 (or second end 76) from the distal end 12 of the elongate member 10 can vary according to the device and application as long as the disconnect point is sufficiently close to the distal end of the device to allow for remote uncoupling within the work site. It has been determined that 6 cm is an advantageous coupling region length for many biliary devices of the present invention in that it provides a sufficient length to prevent accidental uncoupling, while still allowing for the anatomical constraints of the duct such that, in most instances, there remains sufficient room for the relative movement required for uncoupling.

For biliary applications, the length of coupling region could range from less than 1 cm (e.g., a ring) to at least 15 cm. A more preferred range for most devices would be approximately 3-10 cm with the most preferred range being approximately 5-7 cm. For devices intended for the pancreatic duct, the ideal distance of the side access port 15 to the distal end 12 would be 2-5 cm, given the shorter available distance in which to work. In devices intended for use in body cavities where space is even tighter, the side access port 15 may need to be placed closely adjacent to or at the tip 12 of the device in order for an exchange to be successfully accomplished. On the other hand, procedures in which loss of wire guide access in not particularly of concern, such as in certain vascular procedures and when working in long passageways, such as in the intestinal tract, there may be more options as to where the side access port 15 and coupling region 14 can be located.

The illustrative side access port 15 comprises a semicircular opening (in a cross-sectional view or ovoid shape from a top view) that typically comprises approximately ¼ to ⅓ of the width of the catheter; however, any opening size or shape that permits passage of the wire guide therethrough is possible. It may be advantageous to reinforce the side access port 15 area with one or more wires, sheaths, bands, braiding, or other means which traverse, are bonded to, embedded within, or otherwise reinforce the tubular member at least within the area about the wire guide exit port (side access port) to prevent kinking at that location. The wire guide 11 extends proximally from the distal opening 19 of the first device 10 and exits the passageway 31 and coupling region 14 proximally through the side access port 15, thereby giving the physician access to the proximal end of the wire such that it can be manipulated and locked or otherwise secured during the procedure, if so desired. As noted above, a relatively short distance of the coupling region 14 advantageously allows the coupled devices to be moved relative to each another by a sufficient distance to disengage or uncouple one from the other by advancing the catheter 10 toward the distal tip 25 of the stationary wire guide 11, withdrawing the wire guide until it pulls through the catheter and exits the side access port 15/coupling region 14, or a combination of forward catheter movement and wire guide withdrawal, all preferably in such a manner that the wire guide still remains within the work site (e.g., the duct) to facilitate access by subsequent devices over the indwelling wire.

Insomuch that no external exchange is required with the present invention, it is only necessary to size the length of the wire guide 11 to account for the furthest point the distal portion 60 is to be advanced into the work site (e.g., for uncoupling to take place), the intermediate portion 97 extending from work site, to the outside of the patient or scope, and the proximal portion 59 (FIG. 7) extending therefrom for a length sufficient to be manipulated by the operator, such as to lock the wire guide in place. In the illustrative biliary embodiment, the wire guide 11 is 185 cm in length so as to provide a minimal, but adequate extension of the wire from the scope accessory channel; however, other procedures might necessitate a shorter or longer length. Although the length of the wire guide 11 need only be of sufficient length to manipulate or lock or secure in place, if necessary, the proximal portion 59 preferably should be sized to accommodate a traditional short wire exchange procedure, using the appropriately configured devices, if one is required (such as when remote uncoupling may not be possible or desirable for some reason). The wire guide 11 is preferably sized to slidably and releasably reside within the coupling region with minimal friction, although a mechanism is contemplated as part of the present invention in which the catheter (or coextending ancillary device) releasably engages and locks with the wire at a particular point therealong. The coupling region 14 of FIG. 5 comprises the distal portion of the passageway 27 (passageway 31), with the proximal portion 28 of the passageway providing a continuation of the lumen that extends proximally from the point of the side access port 15. Alternatively, the proximal passageway 28 can be at least partially blocked or restricted (with a moveable flap or a permanent obstruction, such a plastic or metal insert) just proximal to the side access port 15 to serve as a guide or ramp that helps the wire guide being loaded from the distal opening 19 to be able to more readily exit through the side access port, rather than continuing on into the proximal passageway. The blocking means (not shown) may also advantageously restrict fluid or other materials from passing through the passageway retrograde direction. In a related embodiment, the wire guide passageway 27 extends proximally only to the side access port 15, terminating at that point.

While the illustrative coupling region 14 of FIGS. 4-5 represent a preferred embodiment for applications in which having the wire guide 11 extending from the distal opening 19 of the tubular member 77 is particularly advantageous, such as for primary access devices used to cannulate a tight stricture, such as the ampullary orifice, it should be noted that any structural adaptation that allows for temporary coupling of the wire guide to a device being introduced therewith or thereover can comprise an embodiment of the coupling region 14 for purposes of remote uncoupling. For example, FIG. 6 depicts a alternative embodiment of the present invention in which the coupling region 14 comprises an external coupling element or channel 30, rather than a portion of the tubular member passageway 27. The illustrative external channel 30, which includes a passageway 31 extending therethrough, can either be integrally formed with the catheter body, or can be bonded or otherwise attached to the outside thereof. Additionally, the external channel 30 can comprise a short piece of sheath encircling the tubular member 77, a plastic or metal ring, or any structure that can form a passageway 31 capable of forming a coupling region 14 with the wire guide.

Figure 30:
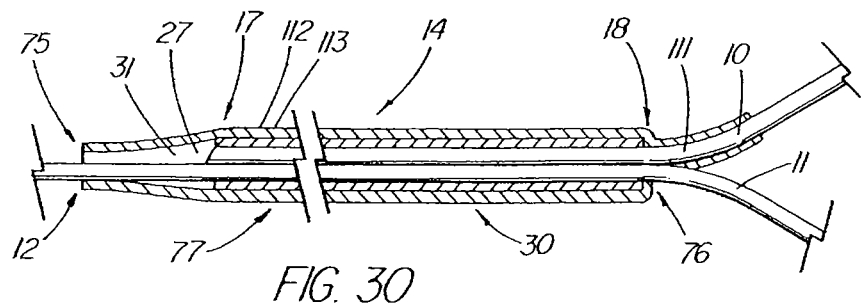
FIG. 30 depicts a partially sectioned view of a wire-guided wire of the present invention.

FIG. 30 depicts an embodiment of an external channel 30 for a device not having an internal passageway. The elongate medical device 10 comprises a wire-guided wire 111 in which the coupling region 14 comprises a outer channel 30 comprising a outer sleeve 112 of shrink wrap material bonded to the wire 111 and a inner sleeve 113 of a radiopaque material bonded to the first sleeve 112 as indicator 17,18 of the first and second ends 75,76 of the coupling region 14. Either a standard wire guide (such as a 0.021" METRO™ wire guide) is fed through the coupling region and the two wires are advanced through an already indwelling tubular member to the work site, or the wire-guide wire 111 is fed over the proximal end of an indwelling standard wire guide (which could also be coupled to a tubular member) and advanced to the work site, where it is uncoupled therein.

Figure 14:
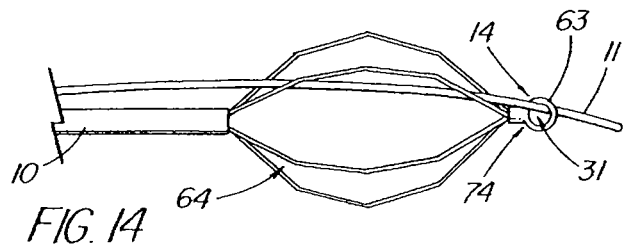
FIG. 14 depicts a side view of a retrieval basket of the present invention that includes a coupling ring to engage the wire guide.

FIG. 14 depicts another alternative embodiment in which the coupling region 14 comprises a coupling ring 63, which in the illustrative embodiment is attached to the distal tip 74 of a retrieval apparatus 64, such as the illustrative wire retrieval basket 64 for capturing biliary stones (a modification of the WEB™ Extraction Basket, Wilson-Cook Medical, Inc.). The illustrative ring 63 is advantageously made to pivot so that it can better accommodate the wire guide 11 which passes therethrough to engage with the first device 10. Coupling rings 63, while not providing as secure of an engagement of the internal passageway, represents an option for certain types of devices lacking a suitable passageway within the shaft portion of the elongate medical device 10 (made of coiled wire in this particular embodiment). The ring 63 requires the least amount of relative movement between devices for uncoupling, which can be advantageous in short work sites or when faced with other anatomical constraints.

Figure 31:
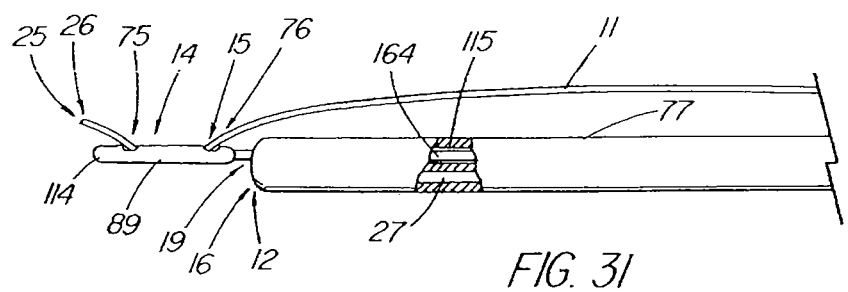
FIGS. 31-32 depict partially sectioned views of embodiment of the present invention in which the coupling region is located on a separate member.

FIGS. 31-36 depict a series of alternative coupling region 14 embodiments. FIG. 31 depicts a tubular member 77 in which the coupling region 14 is located on a separate element, which in the illustrative embodiment, comprises an elongate engagement member 89 comprising a shaft portion 164 slidably disposed in a second passageway 115 and extends from the distal end 12 of the tubular member 77 and engages the wire guide 11 via a cannula portion 115 that includes first and second openings 75,76 through which the wire guide 11 is fed. By locating the elongate engagement member 89 within a second passageway 115, the first passageway 27 remains available for infusing materials or passing a second wire guide therethrough. The embodiment of FIG. 32 also includes a separate elongate engagement member 89 in a second passageway 115 with the elongate engagement member 89 further comprising the coupling region 14. In this illustrative embodiment, the elongate engagement member 89 extends from the side access port 15 and includes a distal ring or loop 45 which ensnares the wire guide and couples the devices together. Optionally, the loop 45 can be made collapsible to pull through the passageway 115 after uncoupling.

Figure 33:
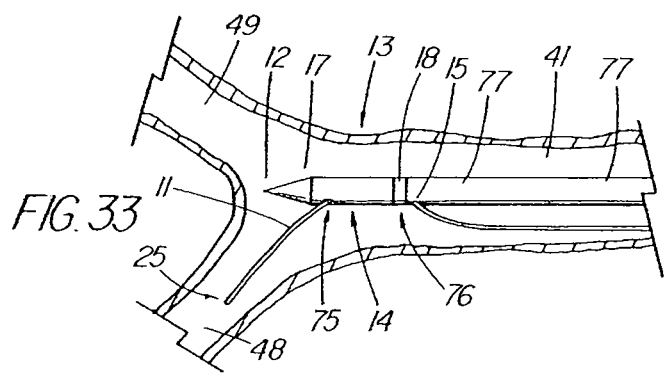
FIG. 33 depicts a side view of an embodiment of the present invention have two distal side access ports.

FIG. 33 depicts a tubular member in which the first end 75 of the coupling region 14 terminates proximal to the distal end 12 of the member, and the second end 76 comprises a side access port 15 located about the distal portion 13 of the tubular member. The wire guide 11 is fed into the coupling region 14 such that the distal end 25 of wire guide 11 is directed at an angle from the tip 12 as it exits the most distal side access port (first end 75). This configuration allows the physician to be able to rotate the tubular member 77 to advantageously direct the tip 25 of the wire guide 11 in an intended direction, such as into a particular branch 48,49 of a bifurcated duct or vessel. The distal end 12 of the tubular member 77 can be closed, or it could include an opening about the tip that could represent a second, alternative first end 75 of the coupling region so that if preferred, the wire guide 11 can also be coupled in the manner similar to FIG. 5.

Figures 34, 35A:
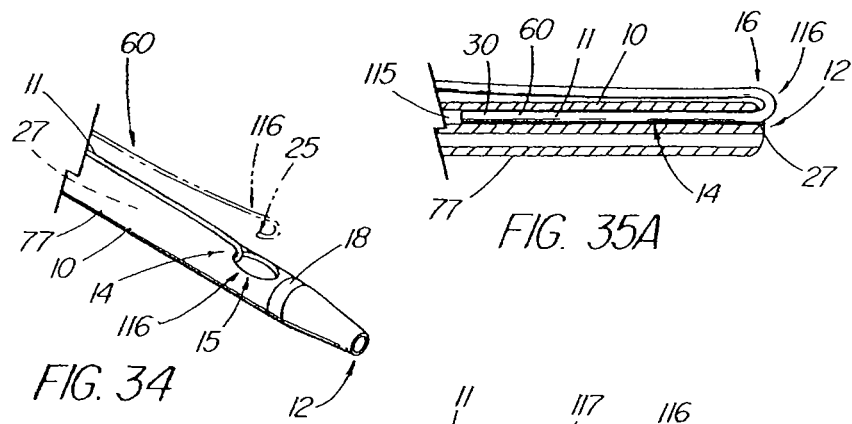
FIG. 34 depicts perspective view of an embodiment of the present invention in which the wire guide hooks into the side access port.
FIGS. 35a-b depicts side views of a hooked wire guide before and after uncoupling.
Figure 35B:
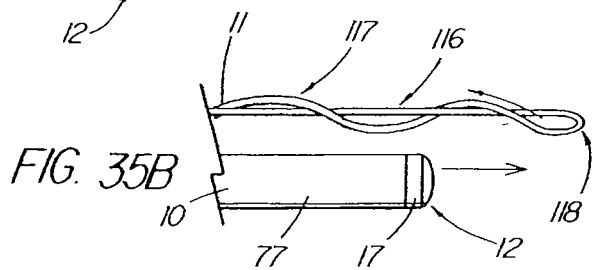

FIGS. 34-35b depict embodiments of the present invention in which the wire guide 11 is adapted to hook into the coupling region 14 in a coupled configuration. In the embodiment of FIG. 34, the wire guide 11 includes a hooked distal portion 116, such as the illustrative 'shepherd's crook' in which the distal end 25 and adjacent distal portion 60 engage the coupling region 14 of the tubular member 77 via the side access port 15, residing within the passageway 27 by an amount sufficient to accomplish a secure engagement. Preferably, the wire guide 11 is sized such that there is a adequate frictional engagement with the passageway 27 in which it resides to help prevent accidental dislodgement. In a related embodiment shown in FIGS. 35a-b, the distal hook portion 116 of the wire guide 11 is configured to be inserted into the distal opening 19 of the tubular member 77, which includes a radiopaque marker band 17 closely proximate thereto. The illustrative distal hook portion 116 comprises nitinol or another superelastic material which allows it to be heat set in a helical configuration 117 that once disengaged from the passageway 31 of the coupling region 14, the hook 116 assumes its predetermined shape and wraps back over itself to create a closed loop end 118. This configuration better permits a second device to be fed back over the wire guide 11 without the hooked portion 116 interfering with its passage thereover. Optionally, the tubular member 77 can include an open longitudinal channel or recess extending proximally from the side access port 15 or distal opening 19 in which the coupled wire guide 11 can at least partially reside while the devices are being advanced together into the work site.

Figures 36, 37:
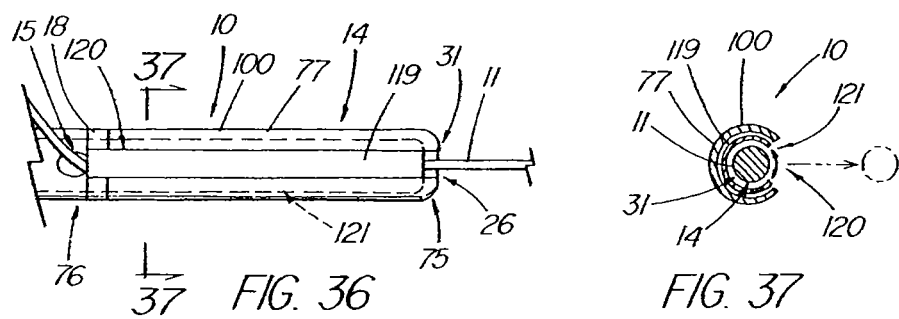
FIG. 36 depicts a side view of an embodiment of the present invention comprising a pair of slotted coaxial members.
FIG. 37 depicts a cross-sectional view of the embodiment of FIG. 36 taken along line 37-37.

Another embodiment of a method of coupling a tubular member 77 to a wire guide 11 is shown in FIGS. 36-37 in which the tubular member comprises a pair of coaxial members 100,119 that each include a slotted opening or channel 120,121 extending the length of the coupling region 14 (distal end 12 to side access port 15) such that when aligned with one another, the wire guide 11 can laterally disengage from the open passageway 31, which is otherwise enclosed by one of the inner 119 and outer 100 sheath members when they are not aligned. Preferably, the proximal portions of the inner and outer members 100,119 (not shown) include proximal makings or structure that allows the physician to determine when rotational alignment has occurred for uncoupling. Alternatively, the slots 120,121 can include radiopaque stripes extending therealong that when superimposed on one another or are otherwise aligned in some manner, indicate radiographically that alignment has occurred such the wire guide can disengage from the passageway 31.

The above coupling region 14 embodiments are merely exemplary of the many options from which a skilled person might select to couple a catheter and wire guide together for introducing them to a work site, the choice being influenced by the nature of the procedure and the devices being used. Other selected examples include, but are not limited to releasable or breakable sutures or wires extending along or through the catheter to capture the wire, compatible, engageable surface structure or elements located on both devices, temporary or dissolvable bonds or adhesives, magnets, or other means of temporarily coupling two medical devices.

Preferably, devices configured for remote uncoupling include an alignment indicator system that allows the clinician to determine the current state of alignment or engagement between a given device and the wire guide or guiding member to which it is temporarily coupled for a particular procedure. In procedures that utilize fluoroscopic guidance of devices within the work site, strategically located radiopaque indicia conveniently provide a means for determining relative alignment and confirmation that uncoupling has occurred. The invention does not require that a particular imagable maker be of a particular type. For example, ultrasonically reflective markers can be used in place of radiopaque bands or other markers. Further, the number and arrangement of the markers is not critical. The alignment indicator system of the present invention may comprise any suitable system in which the first elongate device 10 and wire guide 11 include a predetermined or precalibrated method or means of providing guidance to the physician via external imaging, direct observation (external or endoscopic), tactile sensation, or monitoring of an audible or visual alarm sensor (e.g., activating an indicator light located about the proximal end of the apparatus) to indicate that uncoupling of the two device has occurred within the work site.

Figure 32:
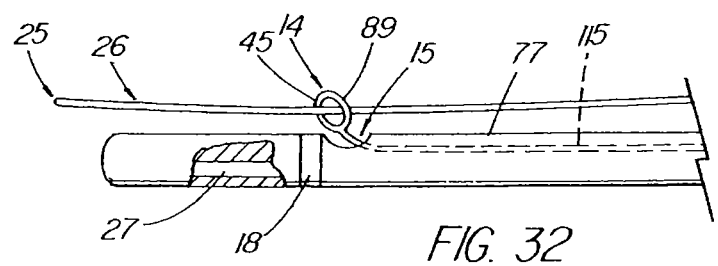

Referring now to FIGS. 4 and 5, the procedure for uncoupling the first device 10 and wire guide 11 within the work site is greatly facilitated by the addition of a first system of indicia 16 located about the distal portions 13,60 of the first device 10 and the wire guide 11, respectively, that comprise a series of radiopaque markers which provide visual guidance under fluoroscopic imaging to the physician or operator as to when the first device is coupled with the wire guide and when the wire guide has passed through and out of the coupling region 14. Since relatively few exchange procedures can be performed under direct visual observation, the distal indicia 16 typically include a series of externally imagable bands, marking, or other indicia comprising a radiopaque (high density) material, such as, iridium, platinum, tungsten, gold, barium, tantalum, etc. The indicia are overlaid upon, bonded to, or incorporated into the device at the desired locations, typically a location useful for relative alignment with other radiopaque indicia or structure. The illustrative first (or distal) system of indicia 16 comprises a series of radiopaque markings on both the first elongate medical device 10 (tubular member 77) and the wire guide 11, including an optional distal imagable marking 17 located about the distal end 12 of the tubular member (or first end 75 of the coupling region), a proximal imagable marking 18 located proximate and distal to the side access port 15, and a distal imagable portion 26 or marker located about the distal end 25 or distal portion 60 of the wire guide 11. The illustrative distal marking 17 of FIG. 4 comprises radiopaque ink having sufficient radiopacity to contrast with the catheter shaft, which in the illustrative embodiment, is also made radiopaque by the addition of barium sulfate or other suitable material into the base polymer. The proximal imagable marking 18 comprises an iridium or platinum band that is glued or otherwise affixed to the catheter surface closely adjacent the distal end of the scive comprising the side access port 15. This band comprises sufficient radiopacity such that it contrasts well with the tubular member to which it is attached, which also may include radiopaque material or pigment. In FIG. 5, the distal radiopaque marker 17 of the tubular member 77 comprises a band similar to band 18 at the proximal end 76 of the coupling region (side access port 15). The illustrative distal radiopaque wire guide portion 26 (FIG. 5) comprises a coilspring comprising platinum, or another radiopaque material such as tungsten or gold. Use of radiopaque filler material or ink is also contemplated as a means for creating a radiopaque wire guide tip portion 26. Placement of a radiopaque marker 18 about the second end 76 of the coupling region 14 advantageously provides a target point at which the physician knows if the radiopaque tip 26 of the wire guide has passed proximal thereto and disengagement has occurred. Although in the illustrative embodiments, the marker 18 is typically located proximal and closely adjacent to the side access port, it may also be placed in any suitable position that is useful for alignment with the wire guide, such as proximal of the port or in alignment therewith, such as depicted in FIG. 6. Alternatively, the marker 18 can comprise a radiopaque stripe or sleeve that extends the length of the coupling region, rather than being limited to the area adjacent the side access port. One such example is depicted in FIG. 31 in which the illustrative metal coupling cannula 114 comprises a highly radiopaque material such as platinum or iridium. In the embodiments of FIGS. 14 and 32, the coupling region 14 comprises a coupling ring 63 which preferably includes enhanced radiopacity to assist the physician in determining when the radiopaque distal portion 26 of the wire guide has passed through and disengaged from the ring.

Figure 8:
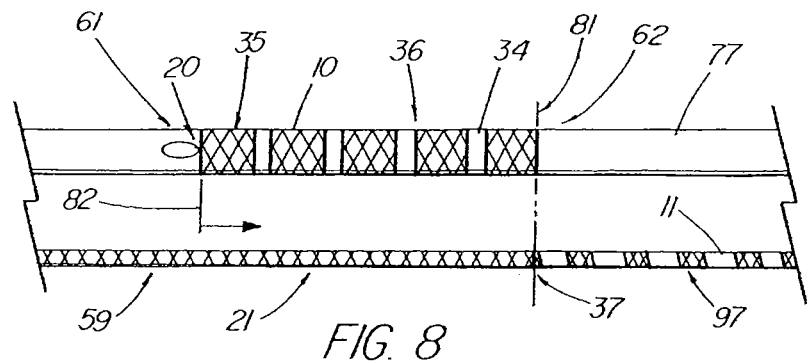
FIG. 8 depicts a side view of an embodiment of proximal system of indicia located on the first elongate medical device and wire guide.

A second system or type of indicia 21 is depicted in FIGS. 4 and 8, and is located on a proximal portion 36 of the first device 10/tubular member 77 that is external to the patient when the distal portion 13 of the device is residing within the work site. During normal operation, the proximal indicia 21 are directly visible by the clinician during the procedure as a primary or secondary means of determining alignment. In the biliary embodiment of FIG. 8, the proximal indicia 21 comprise indicia 35 located about the tubular member 77 and include a series of printed bands that are preferably of a color or pattern contrasting with that of the tubular member 77, and which extend from 160 cm (the first or distal end 62) to the 166 cm mark (second or proximal end 61), as measured from the distal tip of the catheter. The first end 62 (160 cm) represents the point at which alignment with a corresponding proximal alignment mark 37 located on the wire guide, comprises the point of alignment 81 which indicates that uncoupling is imminent with further relative repositioning between the two devices 10,11. Repositioning the proximal alignment mark 37 of the wire guide toward the second end mark 61 results in the two devices reaching the point of detachment 82 at which uncoupling takes place, the colored bands serving as warning that the uncoupling is imminent with further repositioning. In the embodiment of FIG. 4, the proximal indicia 21 comprise a continuous band of contrasting coloration extending from 160 to 166 cm. As noted, the location of the proximal indicia is not particularly critical, but it is preferably configured such that it remains visible to the operator during a typical procedure. The band 35 can include a gradation of colors, (e.g., yellow to orange to red) to indicate the relative proximity to the point of detachment 82. In the illustrative embodiment, the 166 cm mark at the proximal end of the indicia band 35 lies proximate the distal end of an optional proximal side access port 20, which comprises an entry point for a second wire guide into the passageway 27, the technique therefor being discussed below. For non-biliary applications, such as for vascular, pulmonary, or urological procedures, etc., any proximal indicia 21 most likely would be located at a different lengths from the distal tip of the catheter, one appropriately correlated with the distance required to access the work site. The length of the first device indicia 35 (6 cm) preferably corresponds with the length of the coupling region 14 (shown in FIG. 5).

As noted above, the 160-166 cm area of indicia 35 of the proximal indica system 21 advantageously provides a location on the tubular member 77 that will most always be external to the patient and endoscope accessory channel such that it can be viewed by the clinician during the procedure. In the illustrative embodiment, the second alignment point 37 of the wire guide is indicated by a color change between the distal portion 60, which includes helical striping characteristic of the METRO® Wire Guide (Wilson-Cook Medical, Inc.), and the proximal portion 59, which comprises solid coloration, such as a section of shrink wrap or coating of a different color and/or pattern that visually contrasts with the distal portion 60 and/or intermediate portion 97 such that the distal 160 cm of the illustrative wire guide are distinct from and different in appearance from the proximal 25 cm. Alternatively, a contrasting color or ink or suitable material can be applied to the outer surface of the wire guide 11, or a single band can be affixed about the junction 37 between the distal 60 and proximal 59 portions at an appropriate location to establish the point of detachment 82 which occurs by alignment with point 61 of the first device 10. The second alignment point 37 is located on the wire guide 11 such that when it is aligned with the distal end 62 of the proximal indicia 21, the distal end 25 of the wire guide is aligned with the distal end 12 of the first device 10/tubular member 77. Alternatively, the wire guide could include a single, narrow marking at the second alignment point 37, or multiple markings, e.g., corresponding to both the proximal and distal ends 61,62 of the proximal indicia 21. The proximal indicia 21 of the wire guide 11 and catheter 10 comprise any suitable means of providing a visual indicator, such as shrink wrap, ink, bands, surface etching or other treatment, etc.

Figure 26A:
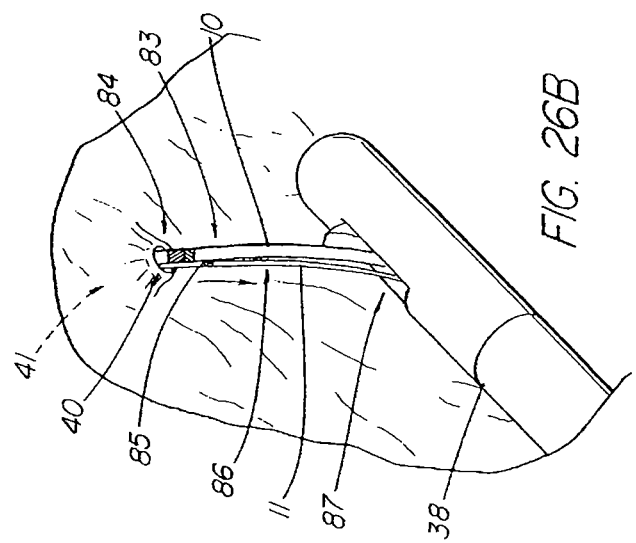
FIGS. 26a-b depict a third system of indicia located on the intermediate, viewable portion of the coupled devices of the present invention.
Figure 26B:
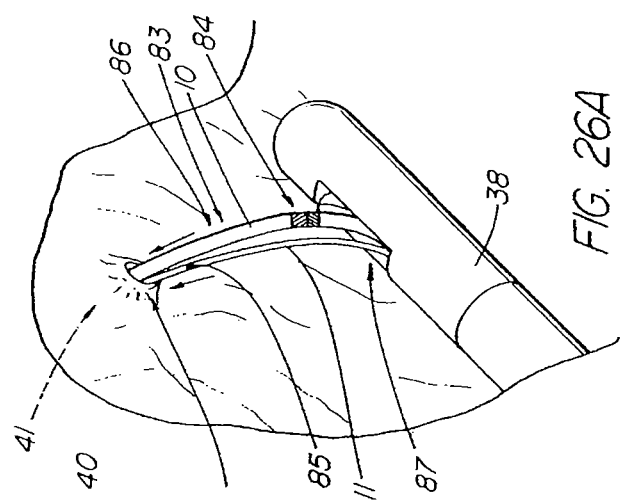

A third type of alignment 83 is depicted in FIGS. 26a and 26b in which the first and second endoscopic alignment indicators 84,85 are located about the intermediate portions of the first elongate medical device 10 (or second catheter, etc.) and wire guide 11, respectively, in a location such that when the distal portions thereof are advanced within the work site 41, the first and second indicators 84,85 are typically disposed within the viewable area 86 between the Papilla of Vater 40 and the distal end 87 of the accessory channel. This allows the operator to monitor the relative alignment of both to determine when uncoupling has occurred within the duct 41 (biliary system). In the illustrative example, the distal ends of the wire guide and first catheter member (not shown) have both traversed the Papilla of Vater 40, and entered the bile duct 41. An optional marking 29 at 10 cm (depicted in FIG. 4 as a pair of printed bands) can be included on the first elongate medical device 10, which is viewable as the device is being introduced into the duct 41. The 10 cm mark 29 can be used for guidance to indicate that the first device 10 has been advanced a minimally 'safe' or sufficient distance into the duct, this occurring once the 10 cm mark 29 has disappeared from view, as shown in FIG. 26a-b. At this point, the endoscopic alignment indicators 84,85 are normally located within the viewable area 86. In FIG. 26a, the first endoscopic alignment indicator 84 of the catheter is located proximal to the corresponding second endoscopic (wire guide) indicator 85, indicating that the wire guide 11 is fully coupled to the first device 10 (i.e., completely traversing the coupling region). In the illustrative method, the operator utilizes the intermediate system of indicia 83 to determine when uncoupling of the devices 10,11 has occurred by advancing the first device 10 relative to the stationary wire guide 11 (which typically is locked down or secured against movement to maintain access within the duct), as shown in FIG. 26b. As the two indicators 84,85 become aligned, the distal end of the wire guide exits the proximal end of the coupling region or side access port (not shown) and uncoupling or disengagement takes place. As a further endoscopic indicator to prevent loss of wire guide access out of the duct during uncoupling, the distal portion 60 (e.g., the distal 6 cm) of the wire guide 11 can comprise a different coloration, such as black, so that it contrasts with the intermediate portion 97 (depicted in FIG. 7). When the physician sees the black portion of the wire guide emerging from the papilla, the wire should be advanced back into the duct to minimize the risk of having to recannulate. If uncoupling has yet to take place and the distal black portion 60 of the wire guide is visible endoscopically, then both the wire guide 11 and tubular member 77 should be advanced further into the duct so that uncoupling can safely take place without risking loss of access.

An example of a non-visual system of alignment is depicted in FIG. 40 in which the wire guide 11 includes a surface irregularity 160, such as the illustrative bead, that is configured such that when it passes through the second end 75 of the coupling region 14, e.g., through the side access port 15, the operator feels or senses the contact between them, thus indicating that uncoupling is imminent with further repositioning. The illustrative side access port 15 is configured to include a flexible skirt 158 that includes an opening 159 sized to allow free passage of the wire guide 11, but causing temporary resistance as the bead 160 passes therethrough. Furthermore, the skirt portion 158 can advantageously act as a seal to help prevent leakage of bile, blood, and air into the passageway of the tubular member. Other possibly surface irregularities include ridges, bumps, teeth, indentations, or a roughened portion that along with an appropriately configured side access port 15 or coupling region 14, provide tactile feedback to the operator and thus, guidance to the state of alignment and engagement between the two devices.

Endoscopic devices used to perform medical procedures within the biliary system are typically divided into what could be called 'primary access devices', which typically comprise the initial device used in the procedure to cannulate the Spincter of Oddi and access the duct, and 'secondary access devices' for which the primary access device is exchanged to perform one or more operations within the work site. Examples of primary access devices of the present invention include sphincterotomes for ablating the sphincter to enlarge the opening to the duct (depicted in FIGS. 10-11), needles knives (not shown), which are also used to cut the sphincter, and ERCP catheters (FIGS. 4-5), which are adapted to infuse contrast media into the duct for radiographic imaging. Sphincterotomes and needles knives may also be configured to perform dual or multiple functions or operations, such as the infusion of contrast media and other agents. Some sphincterotomes include balloon used for sweeping the duct to remove calculi or stones lodged therein. Other devices, such as extraction balloons, may be used as both primary and secondary access devices. In pancreatobiliary procedures, primary access devices are exchanged for secondary access devices that are typically configured to perform a therapeutic function, such as to extract or crush stones, sample tissue, deliver radiation or light therapy, dilate or stent strictures (e.g., tumors), or place stents for drainage. If the secondary access device represents the last device used in a particular procedure, it need not be adapted for remote uncoupling, although it preferably would include at least a distal coupling region so the device can be advanced over a short wire without requiring an extension being added thereto. Generally speaking, virtually any secondary access device (extraction, dilation, or phototherapy balloons, dilator, forceps, brush, stent delivery catheter, brachytherapy catheter, lithotriptor, basket, snare, etc.) that is normally introduced into the biliary system over a wire can be adapted for remote uncoupling by the addition of a suitable coupling region within the distal portion of the device and preferably, but not necessarily, at least one of the three aforementioned systems of indicia to provide positive confirmation of uncoupling and relative alignment of the devices.

Figure 9D:
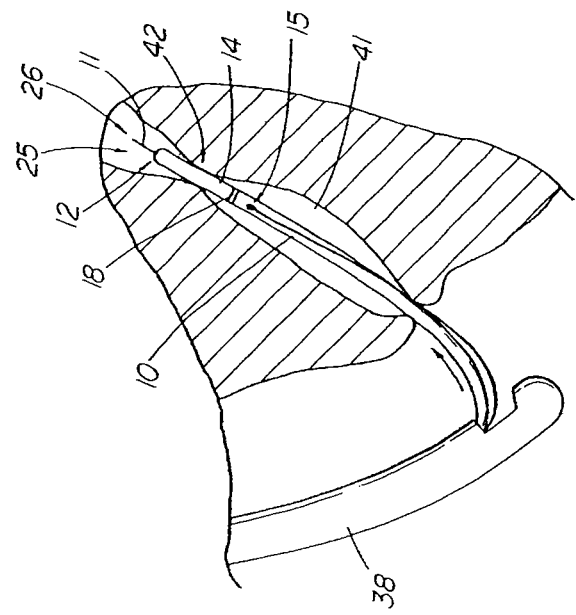
Figure 12:
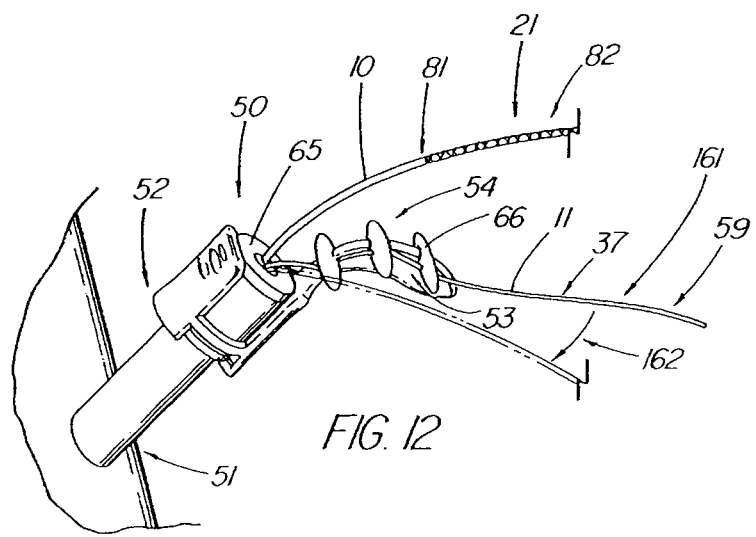
FIG. 12 depicts a perspective view of an illustrative wire guide holding device of the present system and method.

An exemplary method of using a primary access device (first elongate medical device 10), a wire guide 11, and a secondary access device (third elongated medical device 44) of the present invention to access and perform a medical operation in a work site 41 is depicted in FIGS. 9a-f. The initial steps of the illustrative method include a standard endoscopic technique for accessing the biliary duct 41 to perform diagnostic and therapeutic procedures. FIG. 9a shows a duodenoscope 38 that has been introduced via the oral cavity into the duodenum 39 to visualize the Papilla of Vater 40 and Sphincter of Oddi, which lie at the opening to the common bile duct 41 and the pancreatic duct. In the exemplary method, a dilator catheter 88 and wire guide 11 are advanced from the accessory channel of the scope 38 to cannulate a stricture 42 within the work site 41 (duct). It is general physician preference that determines whether the wire guide 11 is advanced past the tip of the primary access device 10 to assist in cannulation or whether the distal end 25 of the wire guide is within the passageway 27 during this part of the procedure. As depicted in FIG. 9b, the dilator catheter 10 (or other secondary access device) is advanced over the wire guide 11 with the proximal portion of the wire guide exiting the side access port 15 and extending through the channel alongside the catheter so that both separately exit the accessory channel of the scope as depicted in FIG. 12. For applications where the size of the scope channel is restricted or other applications where there is limited room to accommodate both devices side by side, the catheter can be modified to allow for the wire guide to lie alongside without increasing the overall diameter. This can be done by forming an open channel (preferably one that would not capture the wire) or creating a flattened longitudinal portion along the length of the catheter (not shown).

Still referring to FIG. 12, the proximal portion 59 of the wire guide 11 is typically, but not necessarily, secured in place once the distal end 25 thereof has been advanced to the desired position within the work site 41. The illustrative wire guide holder 50 represents an improvement over prior art devices in that it is configured to be partially inserted into or over the opening 52 of the access port 51 to the accessory channel and provide a seal, rather than being secured elsewhere on the scope. The holder 50 further includes an optional integrated sealing element 65 having one or more types of seals, including duckbill, membrane with slit (e.g., polystyrene, silicone, or another compliant polymer material), foam seal with small central aperture (e.g., silicon, polyurethane, etc.), or other designs having the ability to seal around the catheter and wire guide to prevent any proximally migrating fluid from exiting the channel. The wire guide 11 is locked in place by interweaving it through a first series of spaces 53 (or channels, grooves, slots, etc) between spaced elements located along one side of a locking portion 66 of the device, such as the illustrative curved 'spine', using an alternating under/over manner as depicted. The illustrative holder includes three slots 53 or spaces on the first side and a second series of three slots 54 or spaces on the opposite side of the locking portion 66 to accommodate a second wire, if one is necessary for the procedure.

Unlike other wire guide exchange procedures where the proximal end of the wire guide is well out of the way of the physician, the short wires typically used in the illustrative remote uncoupling or ultra-short wire techniques usually result in the proximal end of the wire guide being within the physician's working area so that access thereto is readily available for introducing secondary devices to the work site. While the illustrative holder is configured to direct the proximal end portion of the wire guide downward and out of the way of the physician, the proximal end, when unsecured to feed another device over the wire, may deflect back up into the working area around the access port of the scope and can interfere with the physician during the procedure. To help alleviate this problem, FIG. 7 depicts a wire guide 11 in which the proximal end portion 59 thereof is oriented at an angle 79 with respect to the distal and intermediate portions of the wire so that the proximal end 58/proximal end portion 59 is typically oriented down and away from the operator (when rotated as such) and thus, out of the working area surrounding the access port of the endoscope while still allowing the physician to access the proximal end for the advancing the next device. In the illustrative embodiment, which comprises an 185 cm nitinol core wire guide 11 in which approximately 40-45 cm thereof typically is extending proximally out of the scope as the third elongate medical device is being advanced thereover, the bend 80 or point of deflection is preferably located about 20-30 cm from the proximal end, although the useful range may be anywhere from 0-50 cm. The useful angle 79 of deflection depends on physician preference, the configuration of the scope and wire guide holder, and other factors, but is generally about 30-120° for endoscopic procedures with a more preferred range of 45-90° for the illustrative embodiment. To create the bend 80 in a nitinol wire guide 11, the material can either be heat set or mechanically overstressed ('cold working') to achieve the desired angle 79 of deflection and radius of the bend 80 (e.g., small, relatively acute bend or a large, more gradual or rounded bend).

Figure 9C:
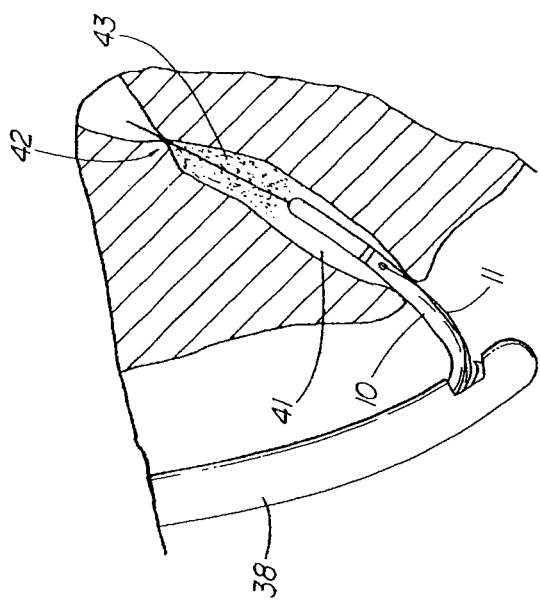

Referring now to FIG. 9c, once the wire guide has been advanced to the desired location within the work site, the catheter is advanced or drawn back over the wire guide to position it for performing the intended operation. In the illustrative method, this involves the injection of contrast media 43 into the duct 41 to visualize the obstruction, which comprises a stricture 42 in this particular instance. Another common alternative approach to diagnosing potential obstructions in the ducts would be to initially introduce a sphincterotome 32 (FIG. 10) to inject contrast media 43. If an obstruction is found, such as a stone, the sphincter might be ablated and a second device, such as a basket or balloon, is introduced over the original wire guide to extract the stone from the duct. A variety of other treatment possibilities exist and thus, it should be understood that the nature and sequence of the devices used is not critical to the present invention.

Once the initial operation has been concluded, the first elongate device 10 can be removed from the duct 41. As depicted in FIG. 9d, the operator can conduct a device IDE by repositioning the distal ends of the ERCP catheter and wire guide 12,25 toward one another by advancing the catheter (as depicted), or preform a wire guide IDE by unlocking the wire guide 11 from the wire guide holder and drawing it back until the distal end 25 disengages from the catheter. Alternatively, the clinician can disengage or uncouple the device and wire guide 10,11 by moving both devices simultaneously until the wire guide exits the coupling region, typically keeping them within the work site 41 while uncoupling takes place. As discussed earlier, imagable indicia 18,26 on the distal portion 13 of the catheter 10 and the distal end 25 of the wire guide 11, respectively, are utilized to confirm under fluoroscopy that disengagement or uncoupling has occurred, as shown in FIG. 9e. The proximal indicia 21, depicted in FIGS. 4 and 8, and/or intermediate indicia 83 (FIGS. 26a-b) may also be utilized to provide confirmation that uncoupling has taken place within the work site. This optional step is shown in FIG. 12 in which the wire guide 11 is in the locked position 161 within the illustrative wire guide holder 50, which is attached about the opening 52 of the biopsy port of the scope (over the rim of the port and/or inserted therein), is subsequently disengaged and placed in the unlocked position 162 adjacent the primary access device 10 so that the proximal indicia 21 of the two devices 10,11 can be aligned. As long as the proximal mark 37 of the wire guide 11 remains distal of the alignment mark 81 of the primary access device 10, the operator knows that distal tip of the wire guide is still protruding from the distal end of the catheter within the duct (not shown). When the wire guide 11 is withdrawn (or primary device 10 advanced) such that the two marks 37,81 are in alignment, the operator knows the distal ends 12,25 of the two devices 10,11 are generally aligned within the duct. As the operator continues to draw back the wire guide 11 or advance the catheter 10, the alignment mark 37 becomes aligned with the disengagement mark 82, which in the illustrative embodiment is indicative that the distal end of the wire guide has pulled completely out of the passageway or coupling area such that the two devices are uncoupled within the duct.

Once uncoupling has taken place, either device 10,11 becomes available as a conduit for introduction of a third elongate medical device to the work site. In the illustrative method depicted, the third elongate device 44 comprises a dilation catheter 88 (FIG. 9f) that is introduced over the wire guide 11 by feeding the back end 58 of the wire guide 11 (not shown) into the distal opening 19 of the dilation catheter 88 and out of the side access port 15, then advancing the dilation catheter 88 into the accessory channel of the scope, over the wire, and on into the duct 41. Typically, the operator would choose to remove the first device 10, if no longer needed, before introducing the third device 44. This is done simply by having the operator pull the catheter out of the duct and scope channel in one continuous motion while maintaining the wire guide in position (e.g., such as locked within the wire guide holder 50 of FIG. 12). Once the first device 10 is removed and the third device 44 is advanced to the work site, the second medical operation (e.g., dilation of the stricture) can be performed. If another operation is required, a third catheter-type device (fourth elongate medical device) can be advanced over the original wire guide 11 and so on.

Figure 13:
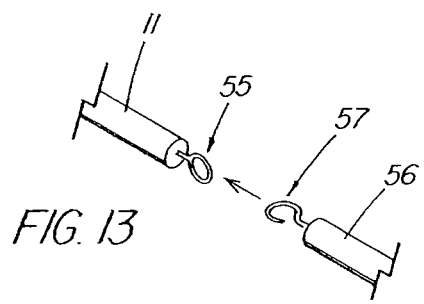
FIG. 13 depicts a side view of a wire guide having a coupling mechanism for attaching a second wire guide to the proximal end thereof.

As noted above, the present system of introducing and exchanging devices over a wire guide is adaptable such that a long wire guide can be introduced through a suitably configured medical device that has been introduced using the ultra-short wire method. In other instances, it may be desirable to convert an indwelling ultra-short wire to a longer wire for use with a non-compatible device. FIG. 13 depicts a wire guide extender 56 for use with the present system to accommodate an external exchange with either a conventional medical device (long wire') lacking the side access port for intraductal exchange, or conventional rapid exchange devices in which a somewhat longer external exchange (e.g., 30 cm) is required. In the illustrative system, the wire guide 11 includes a coupling mechanism 55, such as a thread or wire loop, on the proximal end 58 that is configured to engage with a second coupler 57, such as the illustrative hook, located on the distal end of the wire guide extender 56. This effectively extends the length of the wire guide so that a conventional over-the-wire exchange can take place in the event that a particular device not designed for ultra-short wire exchange is to be used with the present system. One skilled in the art would readily appreciate the various types of coupling mechanisms that would be suitable to accomplish the extension of the wire guide for purposes of an exchange. They include locking or screw mechanisms, sheaths, bands, etc. that permit the two portions 11,56 to be joined temporarily or permanently. Another option is to use an adhesive strip or similar device to attach the wire guide 11 and extender 56 to one another.

Figure 10:
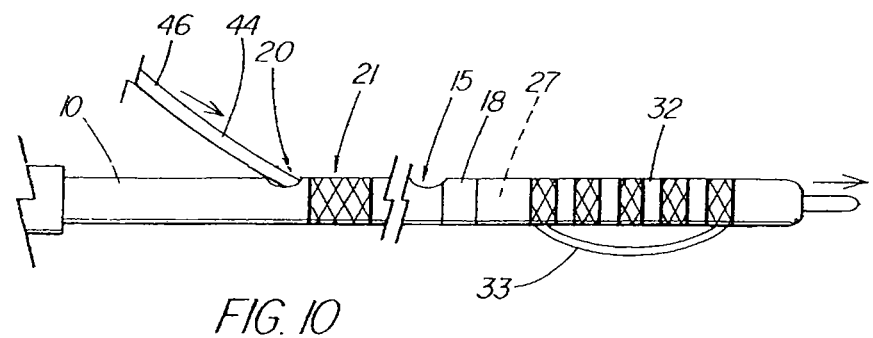
FIG. 10 depicts a side view of an embodiment of the present invention wherein the first elongate medical device comprises a balloon catheter.

The illustrative system of devices that allow for uncoupling within the work site and elimination of the external exchange over the wire can also be adapted for the introduction of second wire guide via an indwelling, uncoupled catheter into the work site, after placement of the first wire guide. FIG. 10 depicts catheter 10 that includes a proximal access port 20 (third opening) located within the proximal portion of the catheter at a point that typically lies outside of the patient during a procedure (approximately 166 cm in the illustrative biliary device example). The proximal side access port 20 may include an optional sleeve cover that slides over and closes the access port when it is not in use.

Figure 11:
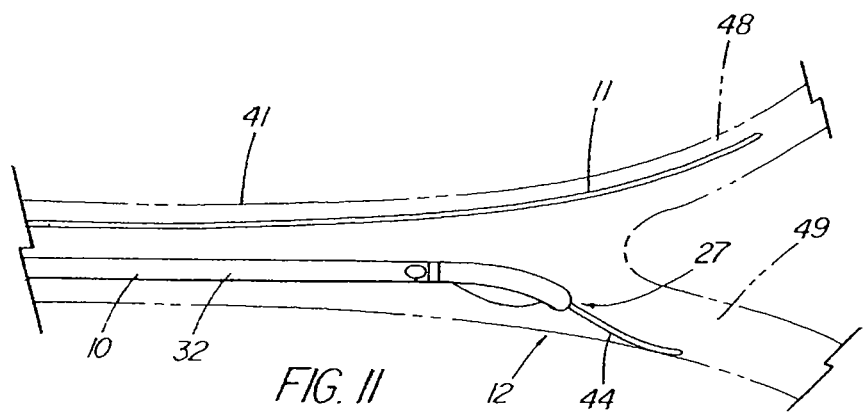
FIG. 11 depicts a view in situ of a sphincterotome of the present invention being used to introduce a second wire guide into a branch of a passageway.

To introduce a second wire 46, the illustrative sphincterotome 32, once disconnected from the first wire guide 11, is not removed from the patient as in the method depicted in FIGS. 9*a-f*. Rather, the tip of the second wire guide 46 (third elongate medical device 44) is fed into the wire guide passageway 27 via the proximal opening 20 and advanced through the scope and into the duct 41. In the example of FIG. 11, the first wire guide 11 resides in a first branch 48 of a bifurcation, such as where the common bile duct 41 branches into the two lobes of the liver. The sphincterotome 32 carrying the second wire guide can be rotated and deflected by the physician, by using the handle to pull back the cutting wire, to advantageously direct the advancing second wire guide into the opposite branch 49 such that each branch is now cannulated by the wire guide 46. A sphincterotome 32 having a handle that provides axial rotation of the catheter body is preferable for orienting the distal cutting portion 33 into or toward the opposite duct for placement of the wire. Once the second wire 46 is in its desire location, it can be locked in place (e.g., using the second series of slots 54 of the illustrative wire holder 50 of FIG. 12). After the sphincterotome or other primary access device 10 has been removed from the second wire 46, both wires 11,46 are available for subsequent placement or introduction of additional devices, such as stents to restore or improve patency of the ducts.

Removal of the original catheter device 10 from the short second wire 46 requires that either an exchange must take place, such as by adding the wire guide extender 56 of FIG. 13 to perform a long-wire exchange; or the catheter may be peeled off of the wire 46 if the portion of the wire guide lumen 27 that lies between the distal (side) and proximal side access ports 15,20 is configured to allow wire to laterally exit the passageway. This can be accomplished in a number of well-known ways including forming a weakness in the wall, such as making a score line, slit 67 or other pre-weakened area inside of the wall, such as that depicted in FIG. 15, or intermittent perforations formed partially or completely through the wall to weaken it longitudinally. Alternatively, the tubular member can comprise an intact catheter wall that is configured to fail when sufficient lateral pressure is exerted by the wire guide residing in the passageway. One method of doing this is to make the wall 68 adjacent the wire guide lumen 27 sufficiently thin (FIG. 16) and/or of a suitable polymer such that when lateral force is applied against the catheter, the wire guide 46 readily splits or tears through the thin wall 68 as the catheter is being withdrawn from the patient. A material with a suitable molecular structure to encourage splitting, such as an isotropically oriented polymer, may be used or the polymer may be treated in some manner to encourage splittability. The entire catheter wall can be configured to facilitate splittability, or the splittable portion may be limited to one specific region along the circumference thereof, such as including a longitudinal coextrusion of a second, lower durometer extending to the outside of the wire guide lumen. Rather than (or in addition to) configuring the wall to increase splittability, a tab or other element can be attached or integrated into the catheter to facilitate a manual split to remove the wire guide. A sharp tool or similar device represents yet another alternative method of accessing the guide wire lumen to separate the catheter from the wire. Another option is to extend the groove completely through the wall to form a narrow, open channel or a sealable or locking seam such that the two edges either are biased against one another or interlock by virtue of their complimentary structure. The seam is designed to split open or unlock when the lateral force supplied by pulling the wire guide thereagainst is sufficient to force it open.

Figure 23:
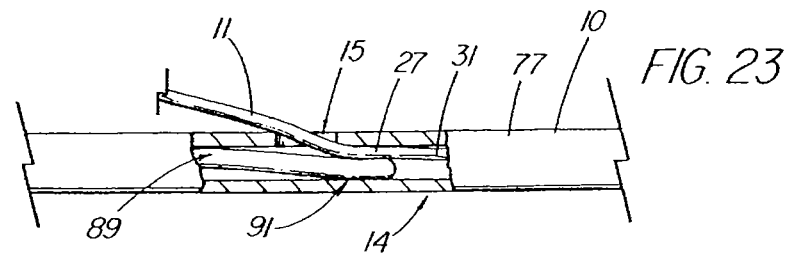
FIG. 23 depicts a partially sectioned side view of a first embodiment of an elongate engagement member (distal portion) comprising a wire stop member.
Figure 24:
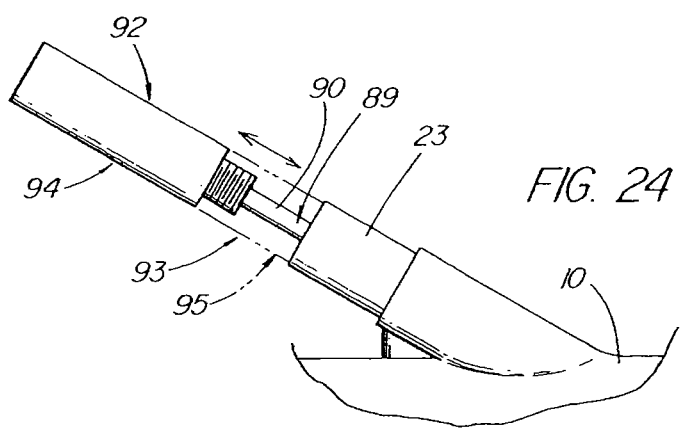
FIG. 24 depicts a side view of the proximal portion of the embodiment of FIG. 23.
Figure 25:
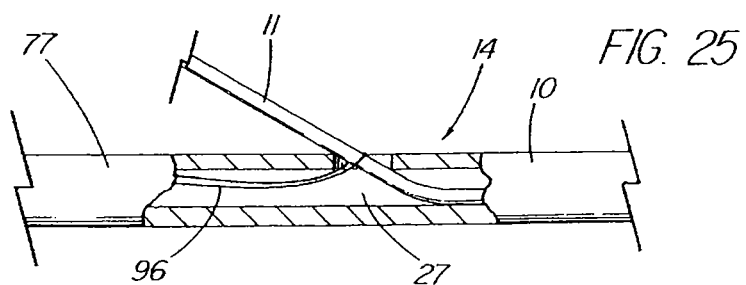
FIG. 25 depicts a partially sectioned side view of a second embodiment of the elongate engagement member comprising a thread-like member.

Returning now to the IDE method depicted in FIGS. 9*a-f*, it has been noted that the friction encountered when introducing a primary access device and a coupled wire guide through the accessory channel of an endoscope can, in some instances, cause premature disengagement of the two device before they reach the work site. FIGS. 23-25 depict different embodiments of an elongate engagement member 89 which is configured to releasably secure the wire guide 11 to the tubular member 77, such that unwanted disengagement or relative movement does not occur as the devices are being introduced or manipulated within the patient. In FIG. 23, the elongate engagement member comprises a wire stop member 90 preferably made of a flexible polymeric material with adequate column strength, such as nylon, which is similar in configuration to a standard pusher member. Preferably, the wire stop member 90 comprises a diameter (e.g., 0.035") that substantially fills the inner diameter of the passageway 27 of the tubular member 77 such that when fully advanced to a point distal to the side access port 15 where the wire guide 11 enters the coupling region 14 (passageway 31), the wire stop member contacts and wedges the wire guide 11 against the inner wall of the passageway, thereby substantially preventing longitudinal movement of the wire guide 11 relative to the tubular member 77. FIG. 23 illustrates the wire stop member 90 disposed within a single-lumen tubular member 77; however, it may be used in multi-lumen device (e.g., a sphincterotome) as well. FIG. 24 depicts the proximal hub 92 (a male luer fitting) of the wire stop member 90 in a retracted position 94 in which the wire stop member 90 is not sufficiently advanced to engage and lock or wedge the wire guide 11 within the passageway 27 a region or point 91 just distal to the side access port 15. To do so, the proximal hub 92 is advanced to a forward position 95 in which the hub 92 contacts and engages the proximal (female) fitting 93 located at the proximal access port 23 of the primary access device 10. Once the operator wishes to reposition the two devices 10,11 relative to one another, the proximal (male) hub 92 is disengaged from the female proximal hub 93 and drawn back until the wire guide 11 is released. Preferably, but not necessarily, the wire stop member 90 is removable from the passageway 27 such that agents, additional wire guides, etc., may be introduced therethrough. An elongate engagement member 89 is typically not used with a secondary access device insomuch that the wire is already indwelling within the work site and the need to secure the wire guide to the device is unnecessary.

A second embodiment of an elongate engagement member 89, depicted in FIG. 25, comprises a thread-like snare member 96 made of suture, wire, cable, or other strand of material which loops around, ensnares, or otherwise releasably engages the wire guide within the passageway 27. The snare member 96 can be attached to an actuating portion of the handle to give the operator sufficient control over its operation. When the operator wishes to disengage the wire guide 11 from the tubular member 77, tension is released on the snare member 96, or it can be cut or one end released so that it can be withdrawn from the passageway 27. Alternatively, the snare member 96 can be disposed on the outside of the tubular member 77 to releasably engage and secure the wire guide 11. The depicted embodiments represent but two possible types of devices adapted for securing the first elongate medical device 10 and wire guide 11 so that they can be co-introduced through a channel without disengaging therein.

The elongate engagement member 89 embodiments of FIGS. 31 and 32 also include the coupling region 14 of the device 10 that may be configured to be partially retractable back into the secondary passageway 115. This action creates a frictional engagement with the wire guide such that the elongate engagement member 89 further acts as a stop to prevent the wire guide 11 from sliding freely within the coupling region 14.

The present invention and method includes using devices in procedures where once the primary access device is used within the work site, a secondary access device is introduced over the guiding device (wire guide) which has been uncoupled from the primary device within the work site. In the biliary tree, a number of possible devices may be introduced to perform a variety of medical procedures, a few selected examples of which are depicted in FIGS. 9F,14,17, 19-22, 27-28, 39, 41-44, 51, and 53. The exemplary devices are certainly not representative of all secondary access devices appropriate for use in the biliary tree, nor is their use particularly limited to being a secondary device used following a primary device. The illustrative devices depict some of the general types of medical devices used endoscopically in the biliary tree, as well as other non-biliary and non-endoscopic procedures performed elsewhere in the body.

FIG. 17 depicts a system for delivering a biliary or pancreatic drainage stent 69 mounted on a delivery catheter 110 (elongate medical device 10) of the present invention. The illustrative COTTON-LEUNG® Biliary Stent (Wilson-Cook, Medical Inc.) is mounted on an OASIS® One Action Stent Delivery System (Wilson-Cook Medical, Inc.), modified for IDE, which extends through the internal lumen 72 of the stent 69, which is slidably mounted thereover (when used with a pusher member 101 (see FIGS. 29a-c). It should be noted that the illustrative stent delivery catheter 110 is configured to accept different kinds of tubular drainage stents in addition to the type shown. The coupling portion 14 of the delivery catheter 110 comprises the passageway 27 between the distal opening 19 and the side access port 15, which is located 1.5-2.0 cm from the distal tip. A proximal marking 18, such as the illustrative iridium band, is located at about 1 cm, just distal to the access port 15. The wire guide 11 exits the side access port 15 at a point distal to the distal end 71 of the stent 69 to advantageously provide a means for withdrawing the stent 69 along with the delivery catheter 110, which greatly assists in the ability to reposition the stent within the duct. When the catheter 10 and wire guide 11 are withdrawn together relative to the stent (which is held stationary by the pusher member), the distal edge 71 of the stent 69, which is slidably positioned over the catheter, lodges in a triangular wedge point 70 formed by the junction of the delivery catheter and the wire exiting therefrom. Thus, the stent 69 is pulled backward along with the delivery catheter, providing the clinician with a simple and reliable means to pull the stent partially out of the duct so that the proximal anchor flaps 73 can extend outside of the duct, if so desired. Once positioned at the desired location, the wire guide 11 and delivery catheter 110 are uncoupled and the latter is withdrawn from the lumen 72 of the stent 69. In delivery systems in which the wire guide 11 extends through the lumen 72 of the stent 69, pulling back on the delivery catheter 110 would not allow the clinician to pull the stent back with it without an additional mechanism to releasably couple the stent to the delivery catheter. It should be noted that this method can be readily adapted for other stent designs as well, particularly other non-expandable tubular stents and those having pusher members.

Figure 29B:
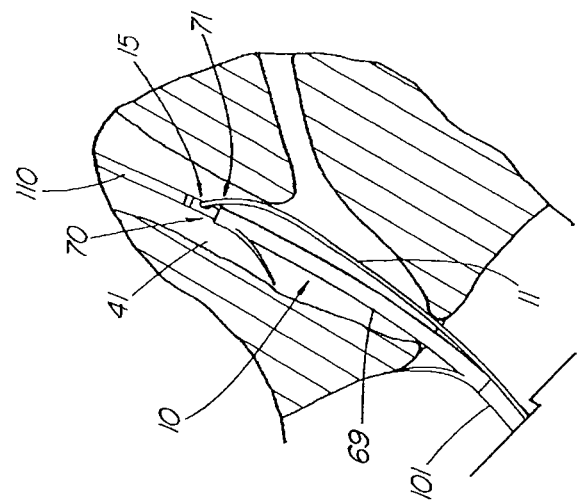
FIGS. 29a-e depict a method of delivering multiple stents within the common bile duct using the system embodied in FIG. 17.
Figure 29A:
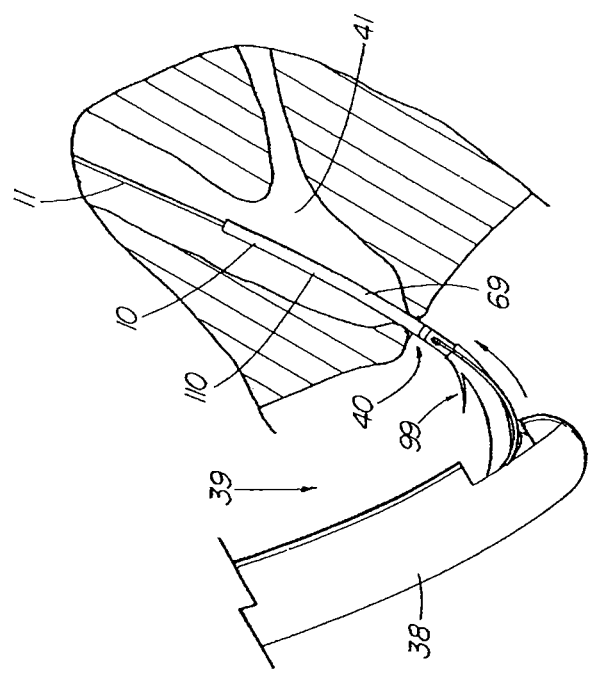
Figure 29C:
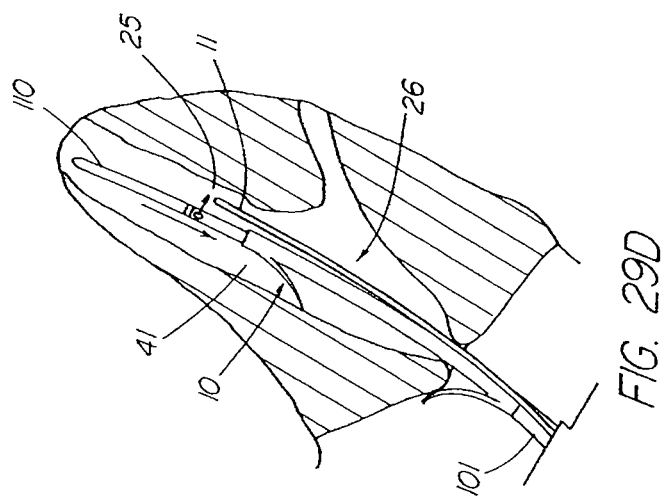
Figure 29D:
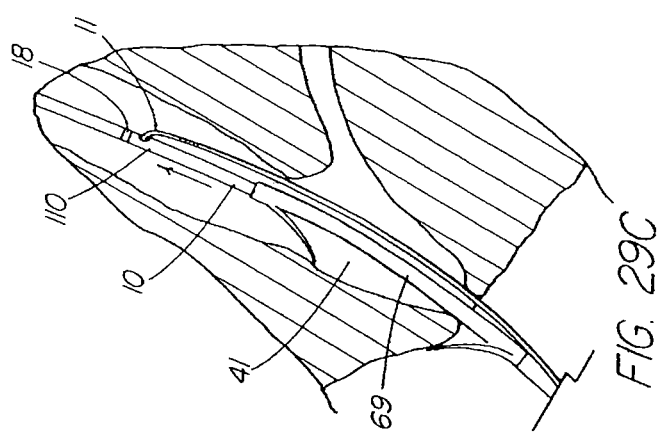
Figure 29E:
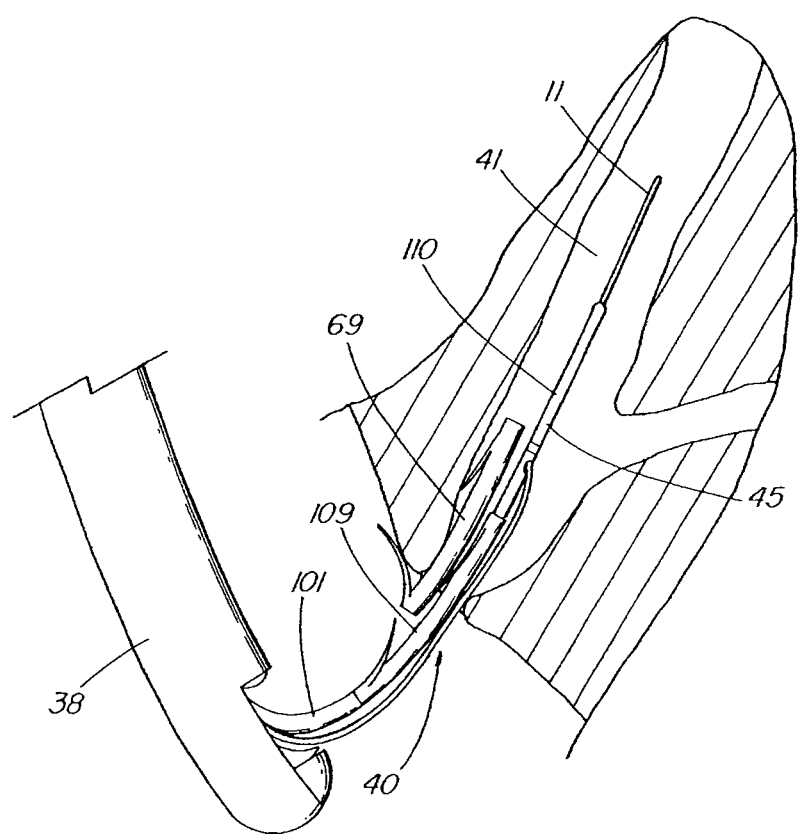

The illustrative stent delivery system of FIG. 17 is particularly well-adapted for placement of multiple stents as depicted in the method of FIGS. 29a-e, insomuch that remote uncoupling of the wire guide 11 and apparatus 10 can be performed within the duct, unlike previous biliary stent delivery systems, thereby eliminating the need for recannulating the papilla for each stent placed. As depicted in FIG. 29a, the inner delivery member 110, which is coupled to the wire guide 11, is advanced out of the endoscope 38, through the ampullary orifice 40 and into the duct 41. The wire guide 11 does not extend through the lumen of the stent 69 and pusher member, which is not yet shown. In FIG. 29b, the pusher member 101 urges the stent over the inner member 110 until the distal end 71 thereof reaches the junction 70 formed where the wire guide 11 exits the side access port (alternatively, the inner member 110 and stent 69 can be pulled back while the pusher member 101 contacts the stent and causes it to advance further up over the inner member 110). As noted above, the junction 70 can be used to contact the distal end 71 of the stent and pull back or reposition the stent 69, such as when it had been advanced too far into the duct for ideal deployment. Once the stent 69 is in the proper position for deployment, as depicted in FIG. 29c, the inner member 110 is advanced further into the duct 41 so that there is sufficient room for the uncoupling procedure to take place. The wire guide 11 is unlocked from the wire guide holder 50 (see FIG. 12) and pulled back until it exits the side access port 15, as depicted in FIG. 29d. The inner member 110 is then withdrawn through the stent 69, along with the pusher member 101, and removed from the channel of the endoscope. The wire guide 11 is then re-advanced further into the duct to serve as a conduit for the next stent delivery system, shown in FIG. 29e, such that a second stent 109 can be deployed alongside the first in the manner shown in FIGS. 29a-d. Subsequent deployments of additional stents can be also be made using the same technique over the original wire guide.

Other stent or prosthesis delivery systems configured for use with the present invention are depicted in FIGS. 22, 27, and 39. FIG. 22 depicts a delivery system 99 for a self-expanding prosthesis 98, which could include a self-expanding stent, such as the Wilson-Cook ZILVER™ Biliary Self-Expanding Stent or any nitinol, stainless steel, or other self-expanding stent; artificial valve (e.g., venous, heart, pulmonary, etc.) prosthesis, vessel occluder, filter, embolic protection device, shunt, stent graft, etc. The illustrative apparatus comprises an inner member (elongate medical device 10) on which the prosthesis 98 is mounted and an outer member 100 or sheath which constrains the self-expanding prosthesis 98 until deployment. The side access port 15 is located about 3 cm from the distal tip 12 of the inner member 10 with the coupling region 14 being completely distal to the prosthesis 98.

An alternative system for deploying a self-expanding prosthesis is depicted in FIG. 39 which includes a series of corresponding slots in the inner and outer members 10,100 to allow for relative repositioning during deployment (the sheath 100 typically being drawn back while the inner member 10 of the delivery system is maintained in position). This permits the coupling region 14 to extend through the prosthesis 98 and allow the wire guide 11 to exit the side access port 15 proximal to the prosthesis 98, which would allow the wire guide to reside inside and be deployed inside prosthesis 98, and as a result, less chance of losing access to the work site. This may be especially advantageous in deployment of stents, other prostheses, and other ancillary devices, such as dilation balloons, within the vascular system in that recannulation through the deployed stent may be problematic, possibly leading to complications such as dislodgement or catching on the deployed stent, dislodgement of plaque, etc. With regard to placement of artificial venous and other types of artificial valves, maintaining wire guide access through the valve may be particularly advantageous in that recannulation through the leaflets or valve structure to deploy additional valves or introduce a seating balloon to fully expand the valve support frame against the walls of the vessel may prove particularly difficult, possibly leading to damage of delicate leaf structure and compromise of valve function.

FIG. 27 depicts an endoscopic biliary stent 69 and pusher apparatus 101 (typically 5.0-7.0 FR) which is configured for ultra-short wire and rapid exchange use. It primarily differs from the embodiment of FIG. 17 in that it lacks the inner member. Both the stent 69 and pusher member 101 (the elongate medical device 10 in this particular embodiment) are introduced through an outer introducer member 100, where the distal end 12 of the pusher apparatus 101, which includes the coupling region 14 about its distal portion 13, urges the stent forward for deployment within the duct. The side access port 15 is located about 6 cm from the distal end 12 of the pusher member 101 (elongate medical device 10) such that the wire guide traverses the passageway of the stent 69.

Figure 41:
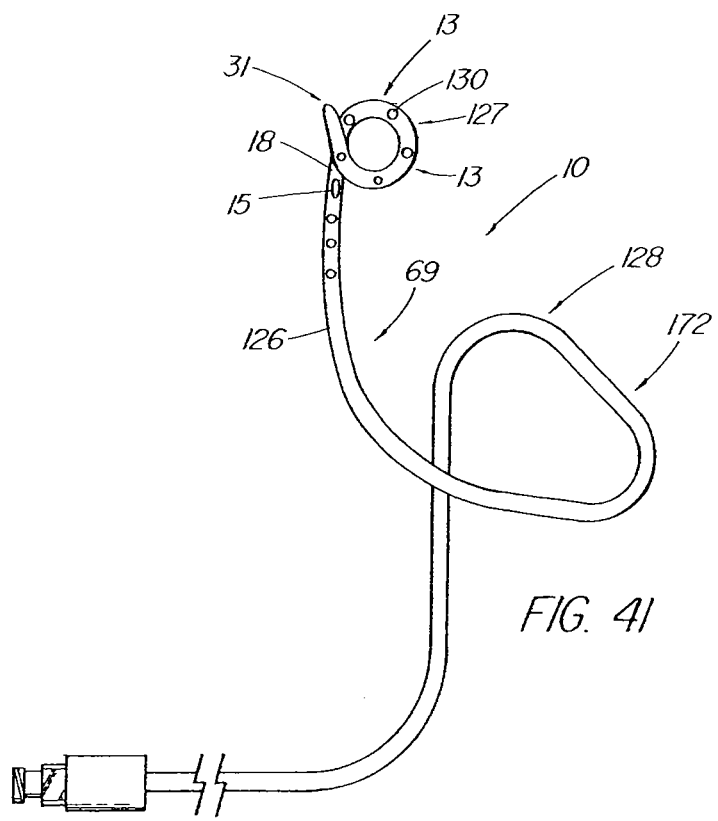
FIG. 41 depicts a side view of a pigtail drainage catheter of the present invention in its deployed configuration.
Figure 42:
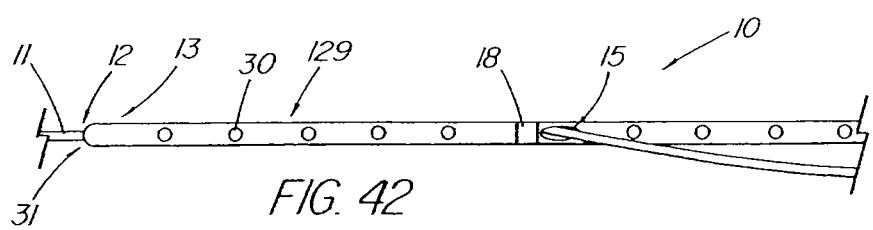
FIG. 42 depicts a partially sectioned view of the embodiment of FIG. 41 coupled to a wire guide.

FIGS. 41-42 depict another embodiment in which the stent 69 comprises a pigtail drainage stent 126, such as the illustrative naso-biliary drainage stent, that includes a curved anchor portion 127 in the deployed configuration 128 (FIG. 41) that is configured to assume a straightened configuration 129 when placed over a wire guide 11 for introduction into the bile duct, as shown in FIG. 42. Preferably, but not necessarily, the drainage holes 130 disposed along the distal portion of the stent 126 are sized such that the wire guide 11 cannot readily exit therethrough (e.g., 0.025"), whereas the side access port 15 is sized to easily accommodate the exiting wire guide (e.g., 0.035" or larger). In the illustrative naso-biliary embodiment, there are five drainage holes distributed about 6 mm apart along the distal portion 13 distal to the side access port 15 and marker band 18. In this particular embodiment, there is a series of optional drainage holes 130 proximal to the side access port 15 as well. The spacing of the drainage holes can vary according to the diameter of the curl, generally ranging from 5 mm to 1 cm or more. As the wire guide 11 is repositioned relative to the stent 126 to perform an intraductal exchange, the anchoring portion 127 recoils into its intended shape when the wire guide is no longer inside the coupling region passageway 31. The illustrative embodiment could also be adapted for use as a naso-pancreatic drainage stent, ureteral or urethral stent, or other stent having one or more curved or pigtailed end portions and various configurations of drainage holes. The illustrative embodiment of FIG. 41 further includes an intermediate curved portion that allows the stent to better conform with the anatomy of the pancreatobiliary tract and duodenum into which it is placed.

Figure 43:
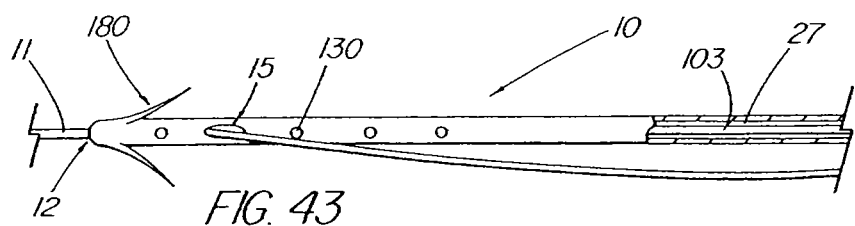
FIG. 43 depicts a side view of an alternate embodiment of a drainage catheter having anchoring flaps.

Another embodiment of naso-biliary and naso-pancreatic drains is depicted in FIG. 43 that is similar to the embodiment of FIGS. 41-42, except that it includes a pair of distal anchoring flaps 180 and lacks the pigtail anchoring portion. Furthermore, the side access port is preferably located closer to the distal end 12 of the device (e.g., about 2 cm vs. about 6 cm for the pigtail embodiment). Typically naso-biliary drains are 5-10 FR in diameter while the naso-pancreatic drains are 5-7 FR. Both the pigtail and non-pigtail drain embodiments may advantageously include a stiffening stylet (depicted in FIG. 43) that extends to about the side access port 15 and provides pushability, as well as straightening out a loop or bend, if present, located proximal to the side access port. Such a bend may allow the device to conform to the anatomy of the patient, such as to better traverse the contours of the duodenum. An example of the bend or curved portion 172 is shown in FIG. 41.

FIGS. 19-20 depict balloon 47 embodiments of the present invention that are adapted for short wire use. FIG. 19 comprises a dilation balloon 47 (a modified QUANTUM™ Biliary Balloon, Wilson-Cook Medical, Inc.), which is made of a non-compliant material (e.g., PET) such that balloon member 102 can be inflated to a predetermined diameter to dilate a stricture within the duct. FIG. 20 comprises an extraction balloon 47, such as a modified TRI-EX™ Triple Lumen Extraction Balloon (Wilson-Cook Medical, Inc.), which comprises a non-compliant material (latex, silicone, etc.) which is adapted for sweeping the duct of material, such as stones, sludge, etc. Both embodiments include a side access port 15 about 6 cm from the distal end 12 of the catheter 10 such that the coupling region 14 extends through the balloon member 102 and exits proximal thereto. The embodiment of FIG. 20 further illustrates a removable stiffening stylet 103 that is maintained within the passageway 27 of the catheter member 10 to provide rigidity, especially across the side access port 15 (and optional proximal side access port, not shown) such that kinking is less likely to occur at that point. The stylet, preferably made of metal (e.g., stainless steel) or a relatively stiff plastic or other material, would not provide any engagement function similar to the distal wire lock 90 of FIG. 23 in most applications since that would interfere with the ability to advance the device over the wire guide.

FIG. 21 depicts a biopsy device 104 for collecting cells within the biliary tree. The illustrative embodiment, which comprises a modified CytoMAX II™ Double Lumen Biliary Brush (Wilson-Cook Medical, Inc.), includes a side access port 15 about 6 cm from the distal end 12 of the tubular portion 77 of the device 10 and a brush element 105 disposed about the distal end and extending beyond such that the coupling region 14 terminates proximal of the brush element 105, the distal opening 19 for the wire guide 11 being disposed about the distal end of the tubular member 77 about the base of the brush element 105. An alternative device for delivering a biopsy device 104 or other device within a work site is depicted in FIG. 39. The illustrative tubular member 77 includes a standard coupling region 14 about the distal end except that the passageway 27 of the tubular member, rather than communicating with the passageway 31 of the coupling region 14, terminates about a ramped external opening 122 that is configured to accommodate a separate elongate medical device for introduction to the work site which is not directly coupled to the wire guide 11. The illustrative biopsy device 104 can be advanced to gather a tissue sample, then withdrawn back into the passageway 27 and either removed from the patient with the introducing member 77, or removed therefrom and a second medical device advanced into the passageway to perform a different procedure. In addition to the radiopaque marker band 18 to indicate the location of the second end of the coupling region 14, the illustrative tubular member includes an additional marker 123 located about the ramped opening which provides additional guidance to the operator. The illustrative biopsy device is but one example of a device deliverable in the manner shown in FIG. 39.

Another secondary access device is depicted in FIG. 38, which comprises a brachytherapy or radioactive seed delivery catheter 106 which includes a passageway 27 for the wire guide 11 (and which includes the coupling region 14) and second, closed-ended passageway 107 for receiving a radioactive element 108, such as a catheter, stylet, or individual radioactive seeds that are introduced thereinto. The brachytherapy device 106 is introduced over the wire guide 11 to the treatment site, where it is positioned for a period of time sufficient to deliver an effective therapeutic dose of radiation to adjacent tissue, such as a tumor within the biliary tree. Typically, the side access port 15 is located about 6 cm from the tip which is preferably made of a pliable, atraumatic polymer material. The second passageway is preferably located centrally so that radiation is dispersed evenly in all directions. As a result, the first wire guide passageway may either terminate distal thereto, about the side access port 15, or be offset therefrom, at least becoming so at a point proximal to the side access port 15 and coupling region 14.

FIGS. 44-57 depict a series of non-biliary devices configured for introduction through the patient's mouth, rather than through the accessory channel of a duodenoscope, such as the aforementioned embodiments. Placement of the embodiments of FIGS. 44-57 typically involves using an ultra-short wire guide 11 that is advanced to the treatment site by being coupled to the outside of an endoscope. The wire guide is then uncoupled from the scope and locked in place to serve as a pathway for the introduction of other devices, such as within the esophagus or elsewhere within the gastrointestinal tract. Optionally, the wire guide 11 (FIG. 57) can include a hydrophilic or otherwise lubricious coating or surface 173 (e.g., SLIP-COAT® Biopolymer, STS Biopolymers, Inc., Henrietta N.Y.) to facilitate the advancement of devices thereover after the wire guide has been placed. The coating is advantageously restricted to a portion of the wire guide 11, such as the intermediate portion 97, with the proximal portion 59 that extends out of the patient and is manipulated and locked by the operation (e.g., the proximal 10-15 cm) having a standard non-hydrophilic surface (e.g., PTFE) to make it easier to secure the wire guide in place. The distal portion 60 (e.g., 2-6 cm) of the wire guide may also be left uncoated to give the operator a better degree of control to help avoid accidental, premature uncoupling of the wire guide from the coupling region of the devices being advanced thereover. The lubricious intermediate portion 97 of the illustrative wire guide of FIG. 57 is especially advantageous when used in the small or colon to allow the device to slide more easily therewithin, while still allowing the wire to be secured at each end by the bite block and distal loop 144, respectively.

Figure 44:
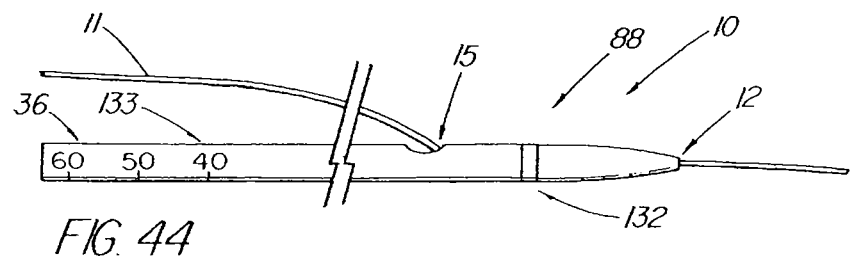
FIG. 44 depicts a side view of a dilator catheter of the present invention.
Figure 45A:
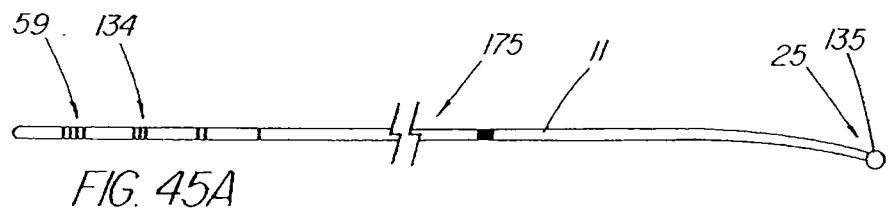
FIG. 45 depicts a side view of a wire guide of the present invention adapted for being carried by an endoscope to a work site.
Figure 45B:
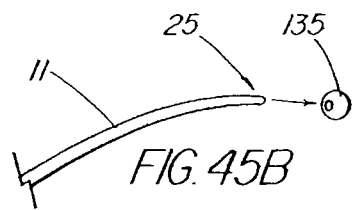

FIGS. 44 and 45 depict a dilator catheter 88 and wire guide 11 comprising a system for dilating strictures within the esophagus. The dilator 88 includes a system of scale indicia 133 located about the proximal portion of the tubular member. In the illustrative embodiment, which is about 75 cm in length, indicia are located to indicate the 40, 50, and 60 cm mark to help align the device with the indwelling wire guide 11, which includes a similar series of indicia 134, such as the illustrative bands that increase in number at each 10 cm interval to indicate the distance from a reference point. The alignment indicia 133,134 advantageously permit accurate positioning of the device at the treatment site, such as the GE (gastroesophageal) junction, a stricture, or other site that is to be dilated, irradiated, or otherwise treated, after the treatment site has been confirmed using the endoscope used to carry the wire guide thereto.

Figure 55A:
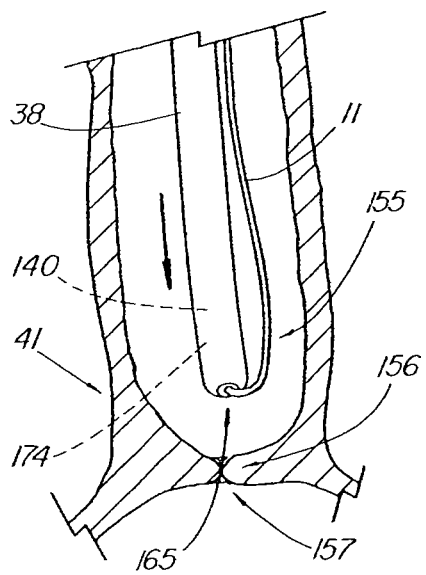

A method for introducing the wire guide 11 and dilator catheter 88 of FIGS. 44 and 45 into the esophagus to perform a series of esophageal dilations using successively larger dilator catheters is depicted in FIGS. 55a-f. The basic method can also be used for introducing other devices that are too large to be introduced through an accessory channel of an endoscope or where standard endoscopic placement techniques either are not appropriate or not possible. As shown in FIG. 55a, the wire guide 11 is carried to the work site using an endoscope 38 and a wire guide carrying mechanism 174, which in the illustrative embodiment comprises the endoscopic wire guide holder 140 depicted in FIG. 48, which resides within the accessory channel 165 of the scope and includes a mechanism to couple with the wire guide 11 via a distal loop 144 about the distal end 25 thereof. As shown, the endoscopic wire guide holder 140 comprises a catheter portion having a lateral recess 142 proximate the distal end 12 thereof and a longitudinal slidable pin member 141, disposed within a passageway 145 in the shaft 146 of wire guide holder 140, that is adapted to traverse the distal loop 144 of the wire guide. The pin member 141 is advanced to secure the loop 144 within the recess 142 to carry the wire guide 11, which is at least substantially outside of the scope accessory channel 165, down to the work site, where it is released by the operator by actuating the finger ring portion 148 of the handle 147 relative to the thumb ring 149 until the loop 144 slips off the retracting pin member 141. When the pin 141 is fully advanced into a locking channel 143 that extends distally from the lateral recess 142, the loop 144 is secured and cannot slip free. The endoscopic wire guide holder 140, which is then withdrawn from the work site along with the endoscope, can either carry the wire guide 11 while partially extending from the accessory channel, or be withdrawn into the accessory channel 165 (as shown) such that the distal end 25 of the wire guide is pulled thereinto.

Figure 47:
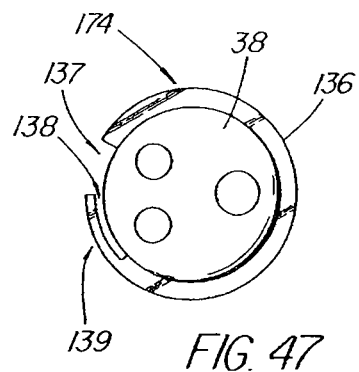
FIG. 47 depicts an end view of the embodiment of FIG. 46.
Figure 46:
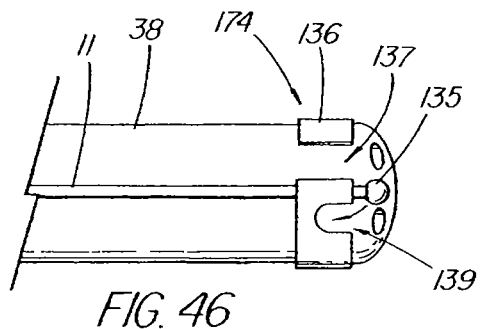
FIG. 46 depicts a side view of device attached to an endoscope which for carrying the wire guide of FIG. 45.

A second embodiment of a wire guide carrying mechanism 174 is depicted in FIGS. 46-47 comprising a ring element 136 that attaches to the outside of the endoscope 38 about the distal end thereof using a friction fit, clamping mechanism, or some other well-known means, and is configured to releasably secure the wire guide 11 being carried to the work site. The wire guide 11 includes a detachable element 135, such as the illustrative distal ball, which is crimped, glued, or otherwise fastened about the end 25 of the wire guide and designed to slide off or break apart with the application of a sufficient amount of pull force (e.g., 3 lbs.) and be safely passed through the gastrointestinal system or be absorbed thereby. The ball tip 135 is inserted into an open slot 137 in the ring 136 and then slipped laterally beneath a lip portion 138 and into a recess 139 that together, help secure the wire guide and allow it to be pulled along with the scope. With the ball 135 residing in the recess 139 formed along the distal edge of the ring, the wire guide 11 can be uncoupled from the scope 38 by pulling on the proximal portion of the wire guide while maintaining a counter force against the scope 38 to keep it in place. When the ball 135 is dislodged (FIG. 45a), the wire guide 11 can slip under the lip portion 138 (FIG. 47) and the endoscope 38 can be withdrawn from the patient, leaving the wire guide in place.

Figure 55B:
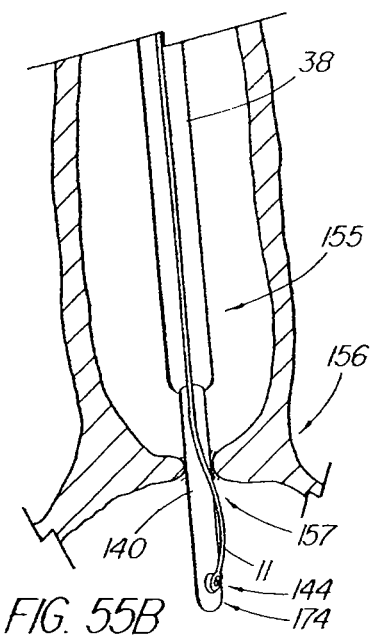

Referring again to FIG. 55a, the endoscope is typically positioned within the work site 41 just proximal to the specific site (sphincter, stricture, lesion, etc.) therein that is to be treated. In the illustrative method, the scope 38 is advanced to the GE junction 156 while depth markings located about the proximal portion of the scope exiting the patient (not shown) provide the operator with the distance from the mouth to the treatment site. At this point, the distal end 25 of the wire guide 11 is also generally positioned at the GE junction 156 since it is engaged proximate the distal end of the scope 38. The endoscope 38 and wire guide are advanced through the esophagus 155 and positioned at the GE junction 156, where that distance is noted. The operator may advance the scope 38 10 cm (or some other similar, predetermined distance), which places the distal end 25 well within the stomach 157 (about 10 cm past the GE junction 156). Or, as depicted in FIG. 55b, the operator may advance the wire guide holding device 140, which may include proximal depth indicia as well, a similar distance beyond the scope 38 and into the stomach 157. The wire guide 11 in the embodiments depicted in FIGS. 45 and 50 include a reference mark 175 located 10 cm from the distal end 25 (or whatever distance the wire guide is to be advanced past the GE junction or other anatomical reference point). The wire guide 11 of the illustrative embodiment depicted in FIG. 45 includes a series of proximal indicia 134 that can comprise varying numbers of markings at selected intervals therealong (e.g., 30, 35, 40, 45, 50, and 55 cm from the reference mark 175). In another embodiment depicted in FIG. 50, the wire guide includes five 5 cm bands 150 of different colors that span from the 30 cm mark to the 55 cm mark as measured from the reference mark 175 which is 10 cm from the tip 25. The indicia 134 may further include 1 cm reference marks 177 (e.g., hash marks) within each colored band 150. Preferably, the bands 150 of the embodiment of FIG. 50 comprise colors that contrast with the adjacent band. For example, cool and warm colors may be advantageously placed adjacent one another to create a sequence such as yellow, green, red, blue, and then orange.

Figure 52:
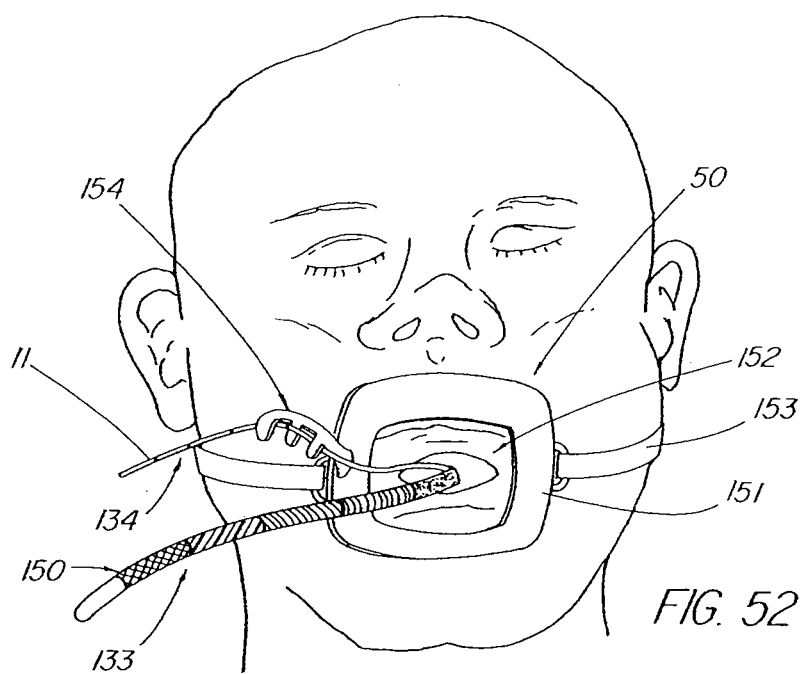
FIG. 52 depicts a plan view of a the devices of FIGS. 50 and 51 being introduced through a bite block/wire guide holder of the present invention.

Once the wire guide 11 has been advanced 10 cm past the GE junction 156, it is uncoupled from the wire guide carrying mechanism 174 and secured in place by some means such as using the illustrative bite block 151 depicted in FIG. 52 with integral wire guide securing portion 154, and which includes straps 153 that secure the bite block 151 around the patient's head. In addition to functioning as a mechanism 50 for securing the wire guide in place, it also maintains an open working area 152 through which the scope, wire guide 11, and primary or secondary devices are passed to the work site.

In instances where a narrow stricture exists that cannot accommodate the scope without risking creating a tear in the esophagus (at least without being properly dilated beforehand), the wire guide holding device 140 advantageously provides a means to safely advance through and traverse the stricture to carry the wire therebeyond and serve as a pathway for advancing the dilators, the smallest of which may be less than the scope diameter.

Figure 55C:
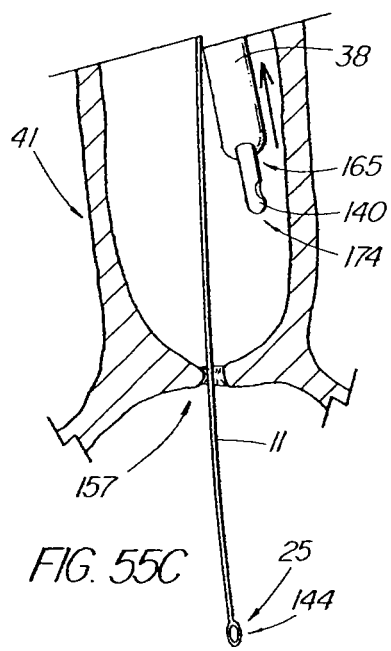
Figure 55D:
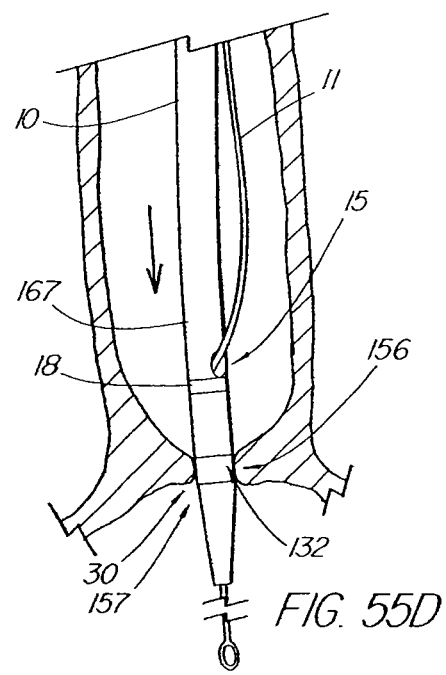

Now referring to FIG. 55c, the endoscope 38 and wire guide holding device 140 are typically withdrawn from the work site 41 such that the primary access device 10, which in the illustrative method comprises a first dilator 167, can be advanced over the wire guide 11 to perform a medical operation, as depicted in FIG. 55d. To advance the first dilator 167, the wire guide 11 is temporarily unlocked from the holding device so that the proximal end thereof can be threaded through the coupling region 14 of the dilator. Alternatively, the primary device 10 (e.g., dilator 167) can be coupled to the wire guide 11 prior to the wire guide being advanced to the work site 41. The illustrative dilator 167 includes optional radiopaque marker bands 18,132 located at the side access port 15 and distal edge of the widest portion of the device before the tapered end, respectively. While it is the GE junction that is established as the anatomical reference point to which the illustrative wire guide 11 and primary access device 10 are aligned, the region of the esophagus having the stricture to be dilated may lie anywhere proximal to the GE junction. Reference to the GE junction is preferred to provide a consistent known distance within the stomach for uncoupling.

The dilator 167 (FIG. 44) also preferably includes a series of proximal indicia 133 as well that are aligned with the wire guide indicia 134 so that the operator can determine when a particular point along the dilator (e.g., distal end of the widest portion 132, distal tip 12, side access port 15, etc.) has reached the GE junction, the tip of the wire guide, or some other reference point.

Once the first dilator 167 has been advanced past the esophageal stricture or the GE junction 156 as the first step of enlarging the opening thereof, the distal portion 13 is advanced fully into the stomach 157 of the patient so that uncoupling can occur, as depicted in FIG. 55e. Typically, this is accomplished by advancing the side access port 15 past the distal end 25 of the wire guide 11, which remains locked in place, until the distal end 25 thereof slides free of the coupling region 14. As with the biliary techniques depicted in FIGS. 9a-f and 29a-e, the uncoupled primary access device 10 is then removed from the patient and a secondary access device (third elongate medical device 44) such as second (larger) dilator 168, is introduced to the work site 41 as depicted in FIG. 55f. Esophageal dilations typically involve passage of a series of progressively larger dilators, although one or more of the smaller sizes may be skipped if resistance is not felt during the initial dilation.

An alternate embodiment of a dilator catheter 167 is shown in FIG. 56 in which the side access port 15 is located on a proximally facing surface or plane 169 formed as the distal (larger) diameter portion 170 of the dilator transitions down to the smaller, proximal portion 171. This advantageously eliminates having the wire guide 11 lying alongside the widest part of the dilator 167 during passage of both through the stricture. The illustrative stepped configuration can also be useful in other embodiments of the present invention to eliminate friction caused by a wire guide passing within a sheath or channel, such as within an endoscope.

Figure 53:
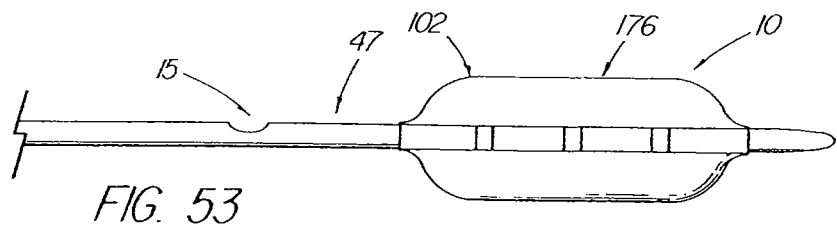
FIG. 53 depicts a side view of an achalasia balloon of the present balloon.
Figure 54:
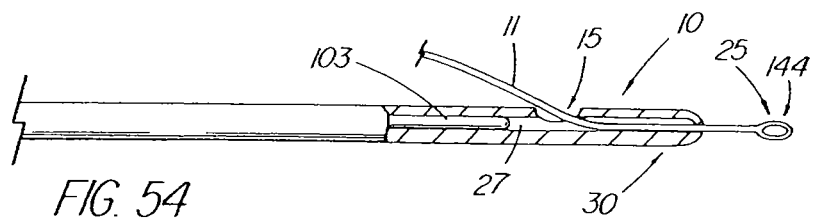
FIG. 54 depicts a partially sectioned view of a naso-enteric tube of the present invention including a stiffening stylet.

The general method of FIGS. 55a-f can also be adapted for placement of other devices outside of the endoscope, such as a photodynamic therapy (PDT) balloon 47, depicted in FIG. 51, or an achalasia balloon 53, depicted in FIG. 53. Both devices depicted are commercially available from Wilson-Cook Medical, Inc. and shown herein as modified for ultra short wire delivery. Positioning of the PDT balloon 47 is performed by using the endoscope to locate the GE junction and place the wire guide 11 at a suitable, known distance therebeyond, such as 10 cm, that distance corresponding to the reference (or 'zero') mark 175 of the wire guide. In the illustrative embodiment of FIGS. 50-52, the wire guide includes colored bands 150 that correspond to those comprising the proximal indicia 133 of the PDT balloon catheter 47 such that when the colors are aligned (FIG. 52), the reference point 176 of the device 10, which in the case of the PDT balloon, is the distal edge of the light-emitting portion 178 of the balloon member 102, is located at the GE junction. This places the light-emitting portion 178 at the optimal location to treat the disease (e.g., Barrett's esophagus). It should be noted that the colored bands 150 or other indicia 133,134 of the illustrative embodiments are configured for aligning the treatment device 10 with the wire guide 11 and thus, the site selected for treatment and may or may not have other functions such as to aid in the alignment of the tips 12,25 of the device with one another or with the side access port 15 to indicate that uncoupling is imminent. Separate indicia may be used for alignment relating to coupling and uncoupling. While the colored bands 150 of the wire guide 11 are configured to refer back to the reference mark 175 that corresponds (in this embodiment) to the GE junction, the colored bands 150 of the primary access device 10 are configured such that alignment with those of the wire guide places the device in the correct position for treating the disease. Thus, they are not necessarily (and usually are not) of the same reference scale.

FIG. 53 depicts an embodiment in which the primary access device 10 comprises an achalasia balloon. With the treatment of achalasia differing in that the balloon is placed across the GE junction rather than proximal thereto, the reference point 176 that corresponds to the proximal reference indicia (not shown) and permits the device to be aligned with the GE junction, is located at the center of the balloon member 102 rather than the distal edge as in the PDT balloon.

The technique of dragging the wire guide outside of the scope to the work site, uncoupling it, and advancing a device thereover, is also applicable to a number a larger diameter catheters (FIG. 54), such as feeding tubes (e.g., nasojejunal, nasoenteric, etc.) which are advanced via the mouth into the stomach or small intestines for placement. These catheters may advantageously include a stiffening stylet 103 in the passageway 27 to prevent the scope from dragging the catheter device 10 with it as it is being backed out of the work site, which in turn, could cause the wire guide 11, which is typically locked in place, to pull out of the coupling region 14. The stiffening stylet 103 is removed prior to or after the devices are uncoupled using radiographic, endoscopic, and/or proximally visible indicia located on the two devices 10,11.

While the gastrointestinal tract may at present provide the most obvious anatomical sites for practicing the methods and techniques of the present invention, further changes in interventional medicine may bring about increasing opportunities where remote uncoupling and ultra-short wire techniques may offer a viable alternative to traditional rapid exchange or other current techniques. For example, many common urological procedures were preformed using wire guide exchange until the introduction of videoendoscopes ideal for urological use. This resulted in direct visualization becoming the standard methodology for manipulating and placing devices in the urological tract. Future developments and improvement in external visualization methodology may result in a return to wire guided procedures where remote uncoupling offers a true advantage to the urologist. Similar advancements in other specialties, especially in vascular and coronary medicine, may create situations where the potential benefits of remotely uncoupling may be realized.

Another alternative system and method for remotely uncoupling an exchange wire guide from a first elongate medical device without utilizing a long wire or standard short wire exchange procedure is depicted in FIGS. 57-70. In particular, the various embodiments shown in these figures generally disclose a system and method for uncoupling an exchange wire guide from a first elongate member through the use of a separating member to force or pull the exchange wire guide laterally out through the wall of the first elongate member.

Figures 58A, 58B:
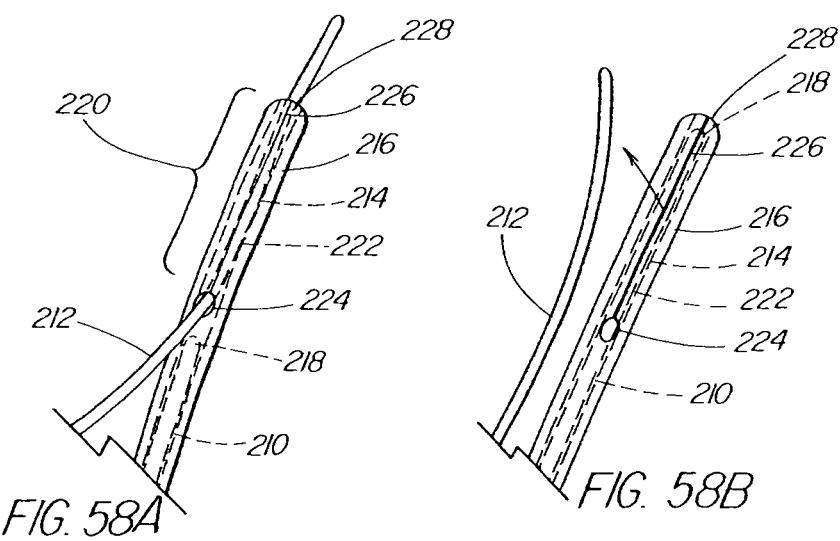
FIGS. 58a-b depict a side view of an alternative method of separating a wire guide from a catheter utilizing an internal separating member.

In the exemplary embodiment of the system shown in FIGS. 58a-b, a separating member 210 is utilized to force the exchange wire guide 212 out of the lumen 214 of the first elongate member 216. As best seen in FIG. 58a, the separating member 210 comprises an internal elongate member that is configured to pass through the lumen 214 of the first elongate member 216. In the embodiment depicted, the separating member 210 comprises a separating wire or wire guide having a diameter, length and column strength that is sufficient to pass through the lumen 214 of the first elongate member 216 so as to engage and expel the portion of the exchange wire guide 212 that is disposed within the lumen 214 of the first elongate member 216.

In an exemplary method of utilizing the internal separating member 210 to uncouple the exchange wire guide 212 from the first elongate member 216, the separating member 210 is inserted through a port (not shown) near the proximal end of the first elongate member 216 and into the lumen 214 of the first elongate member 216. The separating member 210 is then advanced in a distal direction until the distal end 218 of the separating member 210 engages the exchange wire guide 212. As shown in FIG. 58a, contact between the distal end 218 of the separating member 210 and the exchange wire guide 212 typically occurs near the side port 224 that defines the proximal end of the coupling region 220. As shown in FIG. 58b, further advancement of the separating member 210 forces the exchange wire guide 212 out of the lumen 214 by pushing the exchange wire guide 212 through the wall 222 of the first elongate member 216. This is because the cross-sectional area (or inside diameter) of the lumen 214 is not large enough to accommodate both the exchange wire guide 212 and the separating member 210 in a side-by-side arrangement. In other words, as the separating member 210 is advanced into the coupling region 220, the cross-sectional area of the separating member 210 sufficiently fills the cross-sectional area of lumen 214 so as to displace the exchange wire guide 212 from the lumen 214.

The separating member 210 may include an indicator or system of indicia (not shown) that allows a user to determine the position of the distal end 218 of the separating member 210 relative to the coupling region 220 of the first elongate member 216. For example, the separating member 210 may include visual or radiopaque markers similar to the types of indicia used on the exchange wire guides described above and shown in FIGS. 5, 7, 8, 26a-b and 40. Of course, it should be appreciated that any resistance generated by the act of forcing the exchange wire guide 212 out of the lumen 214 and through the wall 222 of the first elongate member 216 will likely be transmitted along the separating member 210 and felt by the user as a tactile sensation.

In the embodiment shown in FIGS. 58a-b, the wall 222 of the first elongate member 216 comprises a longitudinal split 226 extending between the side port 224 and the distal port 228 in the distal end of the first elongate member 216. The longitudinal split 226 facilitates the displacement of the exchange wire guide 212 from the lumen 214 by providing a means for allowing the exchange wire guide 212 to pass through the wall 222 as it is pushed outwardly by separating member 210. The longitudinal split 226 may comprise any number of configurations or structures. For example, the longitudinal split 226 could be formed by a cutting device such as a blade attached to the separating member 210. In addition, the longitudinal split 226 may comprise a series of perforations or a slit that extends partially into or completely through the thickness of the wall 222. A partial slit has the advantage of maintaining a fully enclosed lumen 214 along the coupling region 220 while still providing a substantially weakened section along the wall that can be readily split by the lateral displacement of the exchange wire guide 212. Longitudinal split 226 may alternatively comprise a section of the wall 222 that is relatively thin, has been manufactured from a different material, or otherwise altered during the manufacturing process so as to provide an area along the wall 222 through which the exchange wire guide 212 can readily pass. Longitudinal split 226 may also comprise an open channel having a gap defined by opposing spaced apart edges of the shaft wall. In such an embodiment, the gap preferably has a width that is less than the diameter of the exchange wire guide 212 and/or the diameter of the separating member 210 so as to prevent the exchange wire guide 212 or the separating member 210 from inadvertently or unintentionally passing out through the wall 222 of the first elongate member 216. However, it should be understood that the wall 222 of the first elongate member 216 has sufficient flexibility to allow the opposing spaced apart edges of the wall to flex or spread apart so as to permit the exchange wire guide 212 to be pulled through the gap.

Longitudinal split 226 also provides an additional means for inserting the exchange wire guide 212 into the lumen 214 of the first elongate member 216. More specifically, the exchange wire guide 212 can be pushed laterally through longitudinal split 226 and into lumen 214, thus avoiding the need to pass an end of the exchange wire guide 212 through one of the ports (e.g., side port 224 or distal port 228) of the first elongate member 216. This method of lateral insertion is advantageous for coupling the first elongate member 216 to an intermediate portion of the exchange wire guide 212 because it is a much faster method of coupling.

Longitudinal split 226 can extend along any portion of the first elongate member 216, including the portion extending proximally of side port 224. For example, longitudinal split 226 may extend along the entire length of the first elongate member 216. Such a configuration would permit an exchange wire guide 212 disposed through the entire length of the first elongate member 216 (i.e., when in an over-the-wire configuration) to be uncoupled with a separating member 210. Similarly, the first elongate member 216 could comprise a plurality of side ports disposed through the wall 222 at various locations along the length thereof, with the longitudinal split 226 extending between any two or more of the side ports. The longitudinal split 226 may also comprise different configurations along different portions of the first elongate member 216. For example, a first portion of the longitudinal split 226 extending between a pair on intermediate side ports could comprise an open channel and a second portion of the longitudinal split 226 extending between the distal most intermediate side port and the distal end of the first elongate member 216 could comprise a partial slit forming a weakened wall.

Figures 59A, 59B:
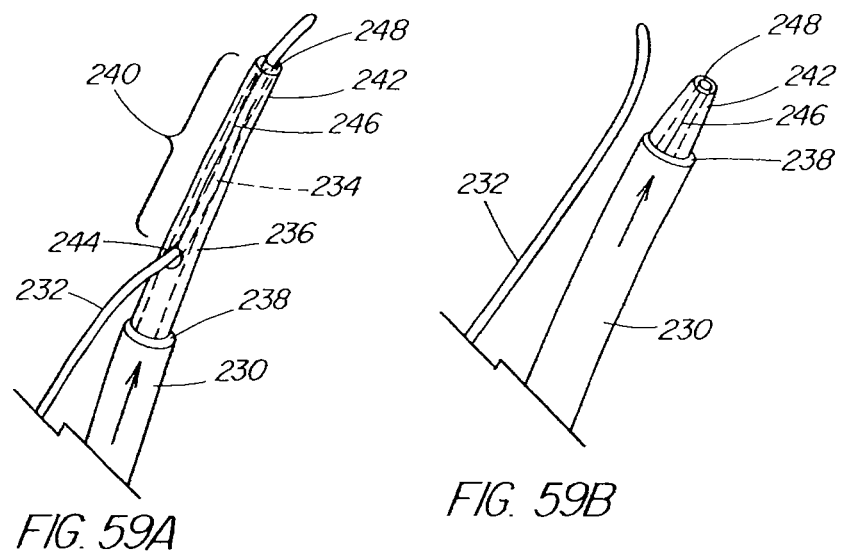
FIGS. 59a-b depict a side view of an alternative method of separating a wire guide from a catheter utilizing an external separating member.

FIGS. 59a-b depict another embodiment of the system and method for uncoupling an exchange wire guide from a first elongate member through the use of a separating member to force or pull the exchange wire guide laterally out through the wall of the first elongate member. In this particular embodiment, separating member 230 comprises an external elongate member that is configured to pass over the exterior of the first elongate member 236 so as to engage and expel the portion of the exchange wire guide 232 that is disposed within the lumen 234 of the first elongate member 236. In the embodiment depicted, the separating member 230 comprises an elongate catheter having a lumen extending though the length thereof, the lumen having a diameter that is sufficient to pass over the exterior of the first elongate member 236. The separating member 230 has a length and column strength that is sufficient to engage the portion of the exchange wire guide 232 that exits from side port 244 and expel the portion of the exchange wire guide 232 that is disposed within the lumen 234 of the first elongate member 236. In the embodiment shown in FIG. 59a, the separating member 230 has a length equal or greater than the length of the first elongate member 236.

In an exemplary method of utilizing the external separating member 230 to uncouple the exchange wire guide 232 from the first elongate member 236, the separating member 230 is passed over the proximal end of the first elongate member 236. The separating member 230 is then advanced in a distal direction until the distal end 238 of the separating member 230 engages the exchange wire guide 232. As can be understood from FIG. 59a, contact between the distal end 238 of the separating member 230 and the exchange wire guide 232 typically occurs near the side port 244 that defines the proximal end of the coupling region 240. In other words, the distal end 238 of the separating member 230 will engage the portion of the exchange wire guide 232 exiting out through side port 244. As shown in FIG. 59b, further advancement of the separating member 230 forces the exchange wire guide 232 out of the lumen 234 by pulling the exchange wire guide 232 laterally out through a longitudinal split 246 in the wall 242 of the first elongate member 236. In other words, as the separating member 230 is advanced into the coupling region 240 and towards distal port 248, the distal end 238 of the separating member exerts a lateral outwardly directed force against the side of the exchange wire guide 232 that causes the exchange wire guide 232 to be pulled out of and separated from the first elongated member 236.

FIGS. 60-62 depict additional embodiments of the system and method for uncoupling an exchange wire guide from a first elongate member through the use of a separating member to force or pull the exchange wire guide laterally out through the wall of the first elongate member. Each of these embodiments is similar to the embodiment depicted in FIGS. 59a-b in that each comprises an external separating member that is configured to pass over the exterior of the first elongate member 236 so as to engage and expel the portion of the exchange wire guide 232 that is disposed within the lumen 234 of the first elongate member 236.

In the embodiment depicted in FIG. 60, the separating member 250 comprises a tubular sleeve having a lumen extending through the center thereof, the lumen having a diameter that is sufficient to pass over the exterior of the first elongate member 236. The separating member 250 is significantly shorter in length then the first elongate member 236. This relatively short length allows the user to grasp and maintain control of the first elongate member 236 as the separating member 250 is advanced along the length thereof. The relatively short length also reduces the friction or resistance to sliding the separating member 250 along the first elongate member 236. The separating member 250 includes a proximally extending pushing member 252 connected thereto that is utilized to advance the separating member 250 along the first elongate member 236. The pushing member 252 has a length sufficient to extend out of the patient and/or endoscope so as to be grasped and manipulated by the user. The method of using the separating member 250 to uncouple the exchange wire guide 232 from the first elongate member 236 is similar to the method describe above in connection with the embodiment depicted in FIGS. 59a-b.

In the embodiment depicted in FIG. 61, the separating member 260 comprises a tubular sleeve having a lumen extending through the center thereof, the lumen having a diameter that is sufficient to pass over the exterior of the first elongate member 236. The separating member 260 also has a split, slot or gap 264 that extends along the wall thereof. The split 264 allows the separating member 260 to be flexed open so as to allow the separating member to be connected or laterally clipped directly onto the first elongate member 236. This avoids the need to pass the separating member 260 over an end of the first elongate member 236, which may be difficult if the end has fittings or connectors that are larger than the outside diameter of the first elongate member 236. Similar to the embodiment depicted in FIG. 60, the separating member 260 is significantly shorter in length then the first elongate member 236. This relatively short length allows the user to grasp and maintain control of the first elongate member 236 as the separating member 260 is advanced along the length thereof. The relatively short length also reduces the friction or resistance to sliding the separating member 260 along the first elongate member 236. The separating member 260 includes a proximally extending pushing member 262 connected thereto that is utilized to advance the separating member 260 along the first elongate member 236. The pushing member 262 has a length sufficient to extend out of the patient and/or endoscope so as to be grasped and manipulated by the user. The method of using the separating member 260 to uncouple the exchange wire guide 232 from the first elongate member 236 is similar to the method describe above in connection with the embodiment depicted in FIGS. 59*a-b*.

In the embodiment depicted in FIG. 62, the separating member 270 comprises a circular ring having an opening in the center thereof, the opening having a diameter that is sufficient to pass over the exterior of the first elongate member 236. The relatively small size of the separating member 270 allows the user to grasp and maintain control of the first elongate member 236 as the separating member 270 is advanced along the length thereof. The relatively small size also reduces the friction or resistance to sliding the separating member 270 along the first elongate member 236. The separating member 270 can comprise any number of suitable materials. For example, the separating member 270 can be rigid, flexible or elastic. An elastic material may be easier to slide along the first elongate member 236. However, the elastic material must still have enough stiffness to force the exchange wire guide 232 out of the lumen 234 of the first elongate member 236 The separating member 270 includes a proximally extending pushing member 272 connected thereto that is utilized to advance the separating member 270 along the first elongate member 236. The pushing member 272 has a length sufficient to extend out of the patient and/or endoscope so as to be grasped and manipulated by the user. The method of using the separating member 270 to uncouple the exchange wire guide 232 from the first elongate member 236 is similar to the method describe above in connection with the embodiment depicted in FIGS. 59*a-b*.

Figure 67:
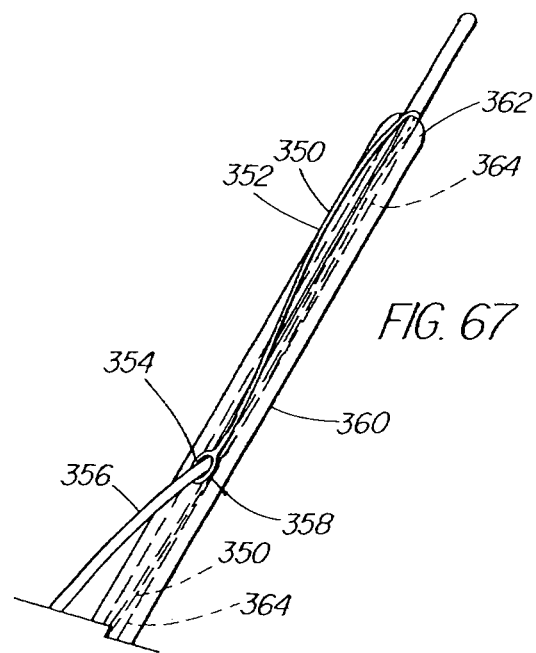
FIG. 67 depicts a side view of an alternative method of separating a wire guide from a catheter utilizing a tether separating member.

FIG. 67 depicts another alternative embodiment of the system and method for uncoupling an exchange wire guide from a first elongate member through the use of a separating member to force or pull the exchange wire guide laterally out through the wall of the first elongate member, wherein the separating member comprises a tether separating member. The tether separating member 350 comprises a length of string 352 with a loop 354 on one end thereof. The loop 354 is disposed over the exchange wire guide 356 at the location where the exchange wire guide 356 exits the proximal port 358 of the first elongate member 360. The portion of the string 352 attached to the loop 354 extends distally along the exterior of the first elongate member 360 until it passes over the distal end 362 thereof and into the lumen 364 of the first elongate member 360. The string 352 passes proximally through the lumen 364 until it exits through a port (not shown) in the proximal end of the first elongate member 360. The exchange wire guide 356 is uncoupled from the first elongate member 360 by pulling the string 352 of the tether separating member 350 in a proximal direction through the lumen 364 so as to pull the loop 354 in a distal direction towards the distal end 362 of the first elongate member 360. The distal movement of the loop 354 pulls the exchange wire guide 356 laterally out of the lumen 364 so as to uncouple it from the first elongate member 360.

FIGS. 63-65 depict additional embodiments of the system and method for uncoupling an exchange wire guide from a first elongate member through the use of a separating member to force or pull the exchange wire guide laterally out through the wall of the first elongate member, wherein the first elongate member comprises an inflatable balloon catheter. More specifically, the first elongate member 280 comprises an inflatable balloon 282 that is configured to perform a medical procedure such as dilating strictures, sweeping obstructions, or temporarily blocking a bodily lumen to during the injection of medications or contrast media. The balloon 282 can comprise various shapes and materials. As best seen in FIGS. 65*a-b*, the balloon 282 comprises at least one groove 284 along the side thereof. The groove 284 is aligned with a split 286 in the shaft wall of the first elongate member 280. As will be explained in greater detail below, the groove 284 and the split 286 cooperate to provide a means through which the exchange wire guide 290 can be removed laterally from the lumen 288 of the first elongate member 280. FIG. 65*a* depicts a balloon having a single groove 284, whereas FIG. 65*b* depicts a balloon having a pair of grooves 284. It should be appreciated that the balloon depicted in FIG. 65*b* comprises two separate balloon halves.

In the embodiment depicted in FIG. 63, the separating member 292 is similar to the internal separating member 210 shown in FIGS. 58*a-b* and discussed in detail above. In other words, the separating member 292 comprises an internal elongate member that is configured to pass through the lumen 288 of the first elongate member 280 so as to engage and expel the portion of the exchange wire guide 290 that is disposed within the lumen 288 of the first elongate member 280. As the exchange wire guide 290 is expelled from the lumen 288, it passes through the split 286 in the shaft wall of the first elongate member 280 and the groove 284 in the balloon 282. Other aspects of the method of using the separating member 292 to uncouple the exchange wire guide 290 from the first elongate member 280 is similar to the method describe above in connection with the embodiment depicted in FIGS. 58*a-b*.

In the embodiment depicted in FIG. 64, the separating member 294 is similar to the external separating member 230 shown in FIGS. 59*a-b* and discussed in detail above. In other words, the separating member 294 comprises an external elongate member that is configured to pass over the exterior of the first elongate first elongate member 280 so as to engage and expel the portion of the exchange wire guide 290 that is disposed within the lumen 288 of the first elongate member 280. As the exchange wire guide 290 is expelled from the lumen 288, it passes through the split 286 in the shaft wall of the first elongate member 280 and the groove 284 in the balloon 282. Other aspects of the method of using the separating member 294 to uncouple the exchange wire guide 290 from the first elongate member 280 is similar to the method describe above in connection with the embodiment depicted in FIGS. 59*a-b*.

Figure 68:
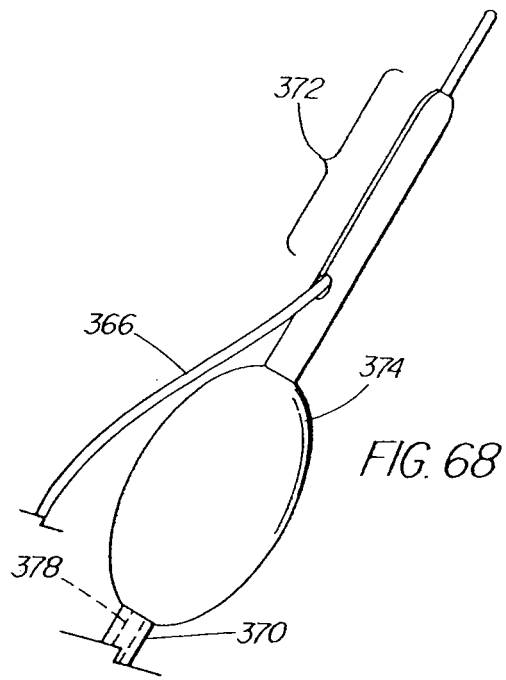
FIG. 68 depicts a side view of another alternative method of separating a wire guide from a balloon catheter utilizing an internal separating member.

FIG. 68 depicts a variation of the inflatable balloon catheter embodiments depicted in FIGS. 63-65. In this particular embodiment, first elongate member 370 comprises a coupling region 372 that is located distally of the balloon 374. As a result, it is not necessary for the exchange wire guide 376 to pass laterally through the balloon 374 when being uncoupled from the first elongate member 370. It is therefore unnecessary for the balloon 374 to include a groove (see FIG. 65a) or comprise separate balloon halves (see FIG. 65b). Other aspects of this embodiment, including the configuration and use of separating member 378, are similar to the embodiment shown in FIG. 63.

FIGS. 66a-b depict an additional embodiment of the system and method for uncoupling an exchange wire guide from a first elongate member through the use of a separating member to force or pull the exchange wire guide laterally out through the wall of the first elongate member, wherein the first elongate member comprises a stent delivery device. As best seen in FIG. 66a, the stent delivery device 300 comprises a self-expanding prosthesis 302 that is supported by an inner member 304 and enclosed by a sheath 306. The inner member 304 comprises a distal tip 308, a proximal cap 310, and a stent support section 312 connected there between. The stent support section 312 has diameter that is less than that of the distal tip 308 and the proximal cap 310 so as to provide a recess for the stent 302 between the inner member 304 and the inside surface of the sheath 306.

The inner member 304 is movably supported by the sheath 306 in a manner that permits stent support section 312 of the inner member 304 to be moved beyond the distal end 318 of the sheath 306. However, the inner member 304 is prevented from becoming completely detached from the sheath 306 by one or more keys 314 projecting outwardly from the proximal cap 310. The keys 314 engage grooves 316 on the inside surface of the sheath 306. The grooves 316 terminate a short distance from the distal end 318 of the sheath 306 and limit the distance the inner member 304 may move relative to the sheath 306. More specifically, the combination of the keys 314 and the grooves 316 prevent the inner member 304 from rotating or moving completely beyond the distal end of the sheath 306. As will be explained in more detail below, the stent 302 is deployed by moving the sheath 306 in proximal direction relative to the inner member 304 so as to allow the stent 302 to expand against the lumen wall 340 of the patient (see FIG. 66b).

The inner member 304 of the stent delivery device 300 further comprises a wire guide lumen 320 extending longitudinally through the interior thereof. As best seen in FIG. 66a, the wire guide lumen 320 extends between a distal port 324 in the distal tip 308 and a proximal opening 326 in the proximal cap 310. The wire guide lumen 320 is configured to allow an exchange wire guide 322 to pass there through. As explained above, the exchange wire guide 322 is used to direct the stent delivery device 300 to the work site within the patient. The sheath 306 comprises a side port 328 through the wall thereof. When the inner member 304 is positioned completely within the sheath 306 (see FIG. 66a), the side port 328 is located near the proximal opening 326 in the proximal cap 310.

The stent delivery device 300 further comprises a separating member 330 that is movably disposed within the sheath 306. The separating member 330 comprises an elongate pushing member 332 having a tapered engagement section 334. The pushing member 332 is configured to slidably move within the sheath 306 and preferably provides stiffness and lateral support thereto. The engagement section 334 is sized to fit within the wire guide lumen 320 of the inner member 304. As will be explained in greater detail below, the engagement section 334 is configured to engage and expel the exchange wire guide 322 laterally out of the wire guide lumen 320 so as to uncouple the exchange wire guide 322 from the stent delivery device 330.

In an exemplary method of delivering a stent 302 with the stent delivery device 300, and utilizing the separating member 330 to uncouple the exchange wire guide 322 from the stent delivery device 330, the stent delivery device 300 is first positioned at the work site within the lumen 340 of the patient. As shown in FIG. 66a, the separating member 330 is then advanced through the sheath 306 until the engagement section 334 engages the exchange wire guide 322. The separating member 330 is then further advanced so as to push the engagement section 334 into the wire guide lumen 320 of the inner member 304. The advancement of the engagement section pushes the exchange wire guide 322 in a lateral direction out of the wire guide lumen 322 and into or through a longitudinal split or channel 336 in the wall of the inner member 304. The separating member 330 is advanced until the engagement section 334 has been completely inserted into the inner member 304 and the pushing member 332 engages the proximal cap 310 of the inner member 304. While maintaining the separating member 330 and the inner member 304 in a stationary position, the sheath 306 is then retracted in a proximal direction. A slot 338 in the sheath 306 allows the sheath 306 to move relative to the exchange wire guide 322. The proximal movement of the sheath 306 exposes the stent support section 312 of the inner member 304 so as to deploy the stent 302. The exchange wire guide 322 becomes fully uncoupled from the stent delivery device 300 once the stent 302 is fully deployed. The stent delivery device 300 can then be removed from the patient. The exchange wire guide 322 can likewise be removed from the patient, or may be maintained with the lumen 340 of the patient and utilized for the introduction of a second stent delivery device or other types of elongate medical devices. For example, the exchange wire guide 322 can be utilized to introduce a balloon catheter device, which may be used to "set" the stent 302 against the lumen 340.

It should be noted that variations of the above-described method are contemplated. For example, the step of retracting the sheath 306 and deploying the stent 302 can be performed prior to advancing the engagement section 334 into the wire guide lumen 320 of the inner member 304.

Figure 69A:
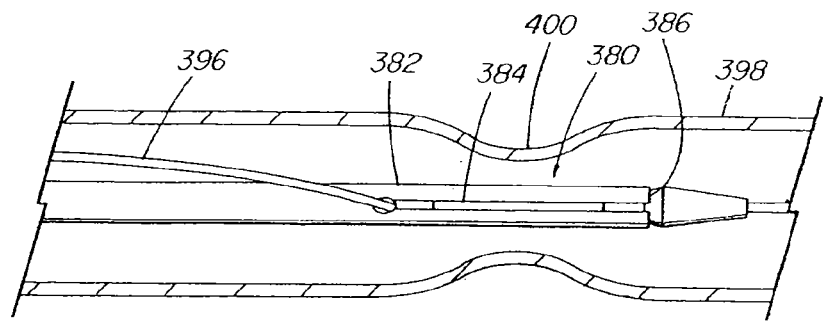
FIGS. 69a-e depict another alternative stent delivery device utilizing the outer sheath to separate the wire guide from the delivery catheter.
Figure 69B:
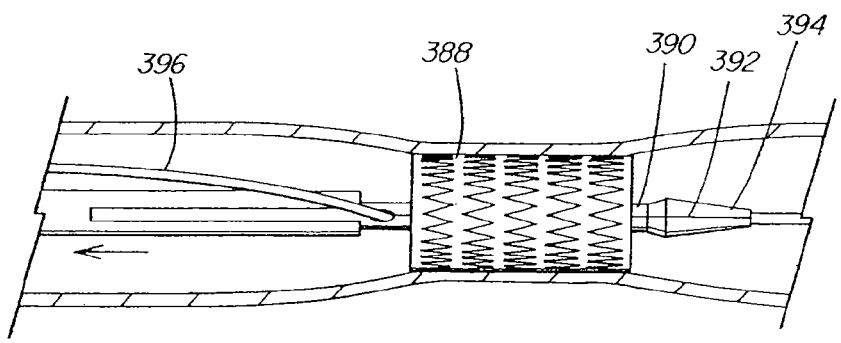

FIGS. 69a-e depict another embodiment of a delivery system for a self-expanding prosthesis, such as a stent, in which the outer sheath, that functions to restrain the prosthesis in an unexpanded delivery configuration, also functions as the separating member. In other words, and as will be explained in detail below, the sheath is utilized as a external separating member to force the exchange wire guide out of the inner member passageway so that uncoupling can occur. As shown in FIG. 69a, the delivery system 380 comprises an outer sheath 382 having a longitudinal split 384 extending along the distal portion thereof, and which generally extends proximally from the distal end 386 of the outer sheath 382 for a distance sufficient to permit the outer sheath 382 to be withdrawn (or the inner member advanced) to deploy the prosthesis 388 (see FIG. 69b). As best seen in FIG. 69b, the inner member 390 likewise includes a longitudinal split 392 extending proximally from the distal end 394 thereof to a side access port 396, which is located proximal of the proximal end of the prosthesis 388. The longitudinal splits 384, 392 of the inner member 390 and outer sheath 382, respectively, are aligned with each other at their proximal ends so that the exchange wire guide 396 can traverse both as it exits the delivery apparatus 380 (see FIG. 69a).

Figure 69C:
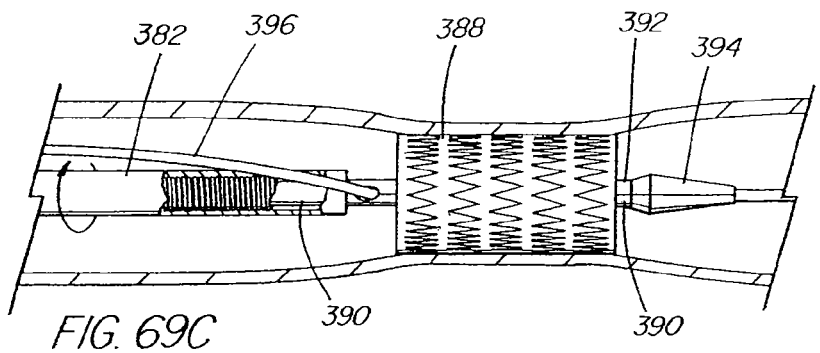

With reference to FIG. 69a, the delivery system 380 is positioned within the bodily lumen 398 of the patient. This is typically accomplished by advancing the delivery system 380 over the exchange wire guide 396 until the prosthesis 388 is positioned so as to traverse, for example, a stricture 400. As shown in FIG. 69b, the outer sheath 382 is then withdrawn or moved in a proximal direction relative to the inner member 390 so as to deploy the prosthesis 388. As the outer sheath 382 is withdrawn, the exchange wire guide 396 traverses the longitudinal split 384 until it passes the distal end 386 and separates completely from the outer sheath 382. As shown in FIG. 69c, the outer sheath 382 is subsequently rotated relative to the inner member 390 such that the longitudinal split 384 of the outer sheath 382 is no longer aligned with the portion of the exchange wire 396 exiting from the longitudinal split 392 in the inner member 390.

Preferably, both the outer sheath 382 and the inner member 390 comprise a material having sufficient torsional rigidity to facilitate the rotation of the distal end 386, 394 via rotation of the proximal end. This especially advantageous in long delivery systems such as those used to deploy carotid artery stents, biliary stents, venous or other artificial valves, etc. For example, the outer sheath 382 may comprise a sheath with superior torqueability characteristics, such as the Cook FLEXOR® Sheath (Cook Incorporated, Bloomington, Ind.), while the inner member 390 may include a torqueable portion such as a coiled wire with a polyamide sheath attached thereto, as depicted in the broken out section in FIG. 69c. In the embodiment illustrated, the inner member 390 comprises different portions having different properties, wherein the distal portion comprises a typical catheter material, such as PEEK, that is not particularly torqueable, while the proximal section comprises a torqueable portion, such as the illustrative coiled sheath.

Figure 69D:
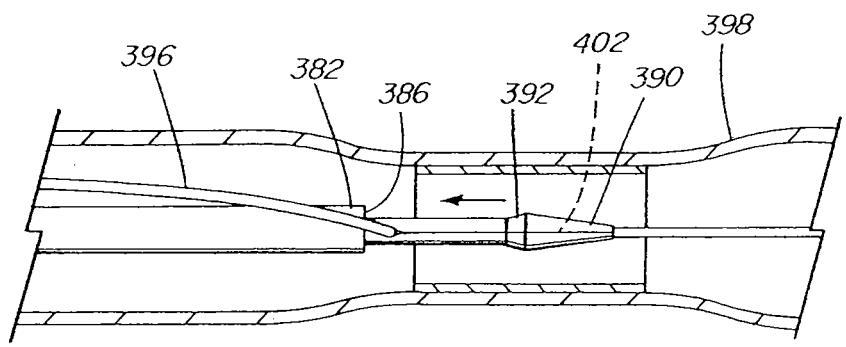
Figure 69E:
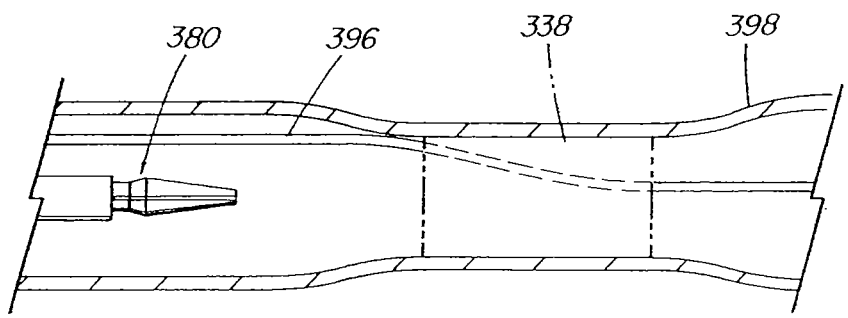

As depicted in FIG. 69d, the distal end 386 of the outer sheath 382 may now function as a separating member to pull or strip the exchange wire guide 396 from the passageway or lumen 402 of the inner member 390 by forcing the exchange wire guide 396 laterally out through the longitudinal split 392 thereof. More specifically, the outer sheath 382 is held stationary while inner member 390 is pulled or moved in a proximal direction relative thereto such that the distal end 386 engages the portion of the exchange wire guide 396 that exits out from the longitudinal split 392 of the inner member 390. Once the exchange wire guide 396 has been uncoupled from the inner member 390, the delivery system 380 can be removed back through the deployed prosthesis 388 (FIG. 69e), leaving the exchange wire guide 396 in position through the prosthesis 388 and available for advancing a second delivery system, seating balloon, or other device thereover.

Figure 70:
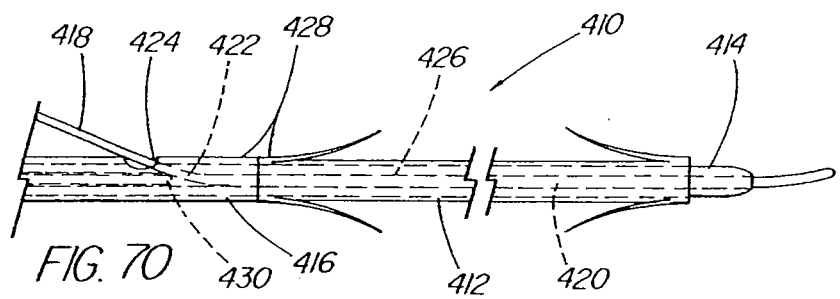
FIG. 70 depicts another alternative stent delivery device utilizing a separating member to uncouple the wire guide from the delivery catheter while simultaneously deploying the stent.

FIG. 70 depicts an embodiment of a delivery system for a non-expanding prosthesis, such as a biliary stent, in which a separating member is used to uncouple the exchange wire guide from the delivery catheter while simultaneously deploying the stent. The delivery system 410 is similar to delivery system depicted in FIG. 27 in that a non-expanding stent 412 is slidably disposed over an elongate inner member 414 and abuts against an elongate outer pusher member 416. An exchange wire guide 418 is coupled to delivery system 410 by extending through a lumen 420 of the inner member 414, the exchange wire guide 418 exiting the inner member 414 through a proximal opening 422 located proximal to the stent 412. The outer pusher member 416 comprises a port 424 aligned and in communication with the proximal opening 422. Alternatively, proximal opening 422 can be disposed between the proximal end of stent 412 and the distal end of the outer pusher member 416, thereby not passing through the outer pusher member 416. In the embodiment illustrated, the inner member 414 and the outer pusher member 416 each have longitudinal splits 426 and 428, respectfully, extending distally from the proximal opening 422 and the port 424. As will be explained below, longitudinal splits 426 and 428 allow the exchange wire guide 418 to be removed from the lumen 420 of the inner member 414 by passing laterally through the walls of the inner member 414 and the outer pusher member 416. In the alternative, the walls of the inner member 414 and the outer pusher member 416 could be configured in some other manner, as described in connection with other embodiments discussed above, to allow lateral removal of the exchange wire guide 418.

The delivery system 410 further comprises a separating member 430 that is configured to extend through the lumen 420 of the inner member 414. In the embodiment illustrated, the separating member 430 comprises an elongate member that extends through the lumen 420 of the inner member 414 so as to engage the portion of the exchange wire guide 418 disposed within the lumen 420. Once the delivery system 410 has been properly positioned at the work site within the bodily lumen of the patient, the separating member 430 is pushed in a proximal direction (or the delivery system 410 is retracted in the distal direction) so as to begin pushing the exchange wire guide 418 out of the lumen 420. As exchange wire guide 418 is pushed laterally out through the walls of the inner member 414 and the outer pusher member 416, it comes into contact with the proximal end of the stent 412. Further movement of the separating member 430 causes the stent 412, via its contact with the exchange wire guide 418, to be pushed proximally off the distal end of the inner member 414. Deployment of the stent 412 and separation of the exchange wire guide 418 from the delivery system 410 are simultaneously completed once the distal end of the separating member 430 reaches the distal end of the inner member 414.

It should be appreciated that the separating member described in the various embodiments above could be adapted so as to be advanced along the exchange wire guide instead of the elongate medical device. For example, the external separating member described in connection with FIGS. 59-62 could be slidably disposed about the exchange wire guide and advanced there along until it engages the elongate medical device, wherein further advancement of the separating member causes the exchange wire guide to separate and uncouple from the elongate medical device.

Any other undisclosed or incidental details of the construction or composition of the various elements of the disclosed embodiment of the present invention or methods of their use are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs and methods described herein are intended to be exemplary only. The novel characteristics of the invention may be incorporated in other structural forms without departing from the spirit and scope of the invention. The invention encompasses embodiments both comprising and consisting of the elements and steps described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27th edition.

What is claimed is:

1. An elongate medical device for introducing multiple members into a work site within a bodily lumen of a patient comprising:
   an elongate flexible shaft extending between a distal end and a proximal end, a lumen extending through at least a portion of the shaft, the lumen comprising a coupling region defined between a distal opening and a proximal opening each disposed through a side wall of the shaft, the distal opening being disposed proximate to or upon the distal end of the shaft, the proximal opening being disposed a substantial distance from the proximal end of the shaft and a relatively shorter distance from the distal end of the shaft, wherein each of the distal and proximal openings are configured to pass an elongate wire guide therethrough;
   an elongate separating member disposed coaxially with the shaft and slidably mounted about an outer surface of the shaft,
   wherein a portion of the wire guide may be disposed within the lumen with opposite ends of the portion of the wire guide extending through the respective distal and proximal openings when in a coupled configuration, and may be transferred to an uncoupled configuration where the wireguide is withdrawn from the lumen and through the coupling region while maintaining the distal end of the shaft and a distal end of the wire guide within the bodily lumen of the patient,
   wherein the separating member is configured to engage and move the wire guide laterally from the coupled configuration to the uncoupled configuration while maintaining the distal end of the shaft and the distal end of the wire guide within the bodily lumen of the patient and without substantially changing the longitudinal position of the wire guide relative to the shaft; and
   wherein the separating member is configured to engage and move the wire guide laterally from the coupled configuration to the uncoupled configuration without extending into the lumen of the shaft wherein the shaft comprises a prosthesis delivery system, further wherein distal movement of the separating member relative to the prosthesis delivery system results in deployment of a prosthesis mounted on the prosthesis delivery system.

2. The device of claim 1, wherein deployment of the prosthesis occurs substantially simultaneously with lateral movement of the wire guide from the coupled configuration to the uncoupled configuration.

3. A method for introducing multiple medical devices into a work site within a bodily lumen of a patient comprising the steps of:
   a) providing an elongate medical device comprising a shaft extending between a distal end and a proximal end, a lumen extending through at least a portion of the shaft between a distal opening in the distal end of the shaft and a proximal port near the proximal end of the shaft, the lumen comprising a coupling region defined between the distal opening and a proximal opening each disposed through a side wall of the shaft, the proximal opening being disposed closer to the distal opening than the proximal port;
   b) providing a wire guide having a distal end and a proximal end;
   c) providing an elongate separating member slidably mounted about an outer surface of the shaft;
   d) extending the wire guide through the proximal opening, the coupling region, and the distal opening of the shaft;
   e) positioning the distal end of the wire guide and the distal end of the shaft within the work site of the patient;
   f) advancing the separating member along the shaft so as to engage a portion of the wire guide extending from the lumen through the proximal opening; and
   g) advancing the separating member in a distal direction relative to the shaft so as to laterally remove the wire guide from the coupling region while maintaining the distal end of the wire guide and the distal end of the shaft within the work site of the patient and without substantially changing the longitudinal position of the wire guide relative to the shaft.

4. The method of claim 3, wherein the separating member does not extend through the side wall of the shaft and into the lumen when engaging the wire guide.

5. A system for introducing multiple medical devices into a work site within a bodily lumen of a patient comprising:
   an elongate medical device comprising a shaft extending between a distal end and a proximal end, a lumen extending through at least a portion of the shaft, the lumen comprising a coupling region defined between a distal opening and a proximal opening each disposed through a side wall of the shaft, the distal opening being disposed proximate to or upon the distal end of the shaft, the proximal opening being disposed a substantial distance from the proximal end of the shaft and a relatively shorter distance from the distal end of the shaft;
   a wire guide having a distal end and a proximal end; and
   an elongate separating member disposed coaxially with the shaft and slidably mounted about an outer surface of the shaft,
   wherein a portion of the wire guide may be disposed within the lumen with opposite ends of the portion of the wire guide extending through the respective distal and proximal openings when in a coupled configuration, and may be transferred to an uncoupled configuration where the wireguide is withdrawn from the lumen and through the coupling region while maintaining the distal end of the shaft and the distal end of the wire guide within the bodily lumen of the patient,
   wherein the separating member is configured to engage and move the wire guide laterally from the coupled configuration to the uncoupled configuration while maintaining the distal end of the shaft and the distal end of the wire guide within the bodily lumen of the patient and without substantially changing the longitudinal position of the wire guide relative to the shaft; and
   wherein the separating member is configured to engage and move the wire guide laterally from the coupled configuration to the uncoupled configuration without extending into the lumen of the shaft,
   wherein the elongate medical device comprises a prosthesis delivery system, wherein distal movement of the separating member relative to the prosthesis delivery system results in deployment of a prosthesis mounted on the prosthesis delivery system.

6. The system of claim 5, wherein deployment of the prosthesis occurs substantially simultaneously with lateral movement of the wire guide from the coupled configuration to the uncoupled configuration.

7. The system of claim 5, wherein the prosthesis delivery system comprises an inner stent support member, and the separating member comprises an outer sheath member slidably disposed over the inner stent support member, the outer sheath member configured to enclose and maintain a self-expanding stent in a contracted delivery configuration until deployed by the prosthesis delivery system.

* * * * *